(12) United States Patent
Pierschbacher et al.

(10) Patent No.: US 6,521,594 B1
(45) Date of Patent: Feb. 18, 2003

(54) METHOD AND COMPOSITION FOR TREATING THROMBOSIS

(75) Inventors: Michael D. Pierschbacher, San Diego, CA (US); Soan Cheng, San Diego, CA (US); William S. Craig, San Diego, CA (US); Juerg F. Tschopp, San Diego, CA (US)

(73) Assignee: La Jolla Cancer Research Foundation, La Jolla, CA (US)

( * ) Notice: Subject to any disclaimer, the term of this patent is extended or adjusted under 35 U.S.C. 154(b) by 0 days.

(21) Appl. No.: 08/445,638

(22) Filed: May 22, 1995

Related U.S. Application Data

(63) Continuation of application No. 08/171,068, filed on Dec. 20, 1993, now abandoned, which is a continuation-in-part of application No. 08/079,441, filed on Jun. 18, 1993, now abandoned, which is a continuation-in-part of application No. 08/050,736, filed on Apr. 14, 1993, now abandoned, which is a continuation-in-part of application No. 07/681,119, filed on Apr. 5, 1991, now abandoned, which is a continuation-in-part of application No. 07/506,444, filed on Apr. 6, 1990, now abandoned.

(51) Int. Cl.$^7$ .......................... A61K 38/12; A61K 38/08
(52) U.S. Cl. ...................... 514/11; 514/9; 514/15; 530/317
(58) Field of Search ................... 514/11, 9, 15; 530/317

(56) References Cited

U.S. PATENT DOCUMENTS

| | | | |
|---|---|---|---|
| 4,517,666 A | 5/1985 | Hideo | |
| 4,547,489 A | 10/1985 | Goldstein | |
| 4,578,079 A | 3/1986 | Ruoslahti et al. | |
| 4,589,881 A | 5/1986 | Pierschbacher et al. | |
| 4,605,512 A | 8/1986 | Schaller et al. | |
| 4,614,517 A | 9/1986 | Ruoslahti | |
| 4,661,111 A | 4/1987 | Ruoslahti et al. | |
| 4,661,471 A | 4/1987 | Hawiger et al. | 514/13 |
| 4,666,884 A | 5/1987 | Hawiger et al. | 514/13 |
| 4,683,291 A | 7/1987 | Zimmerman et al. | |
| 4,789,734 A | 12/1988 | Ruoslahti et al. | |
| 4,792,525 A | 12/1988 | Ruoslahti | |
| 4,857,508 A | 8/1989 | Adams et al. | |
| 4,879,313 A | 11/1989 | Tjoeng et al. | |
| 4,929,601 A | 5/1990 | Brunetti et al. | |
| 4,943,562 A | 7/1990 | Jolles et al. | |
| 5,023,233 A | * 6/1991 | Nutt et al. | 514/11 |
| 5,037,808 A | 8/1991 | Adams | |
| 5,041,380 A | 8/1991 | Ruoslahti | |
| 5,057,604 A | 10/1991 | Brown | 530/387 |
| 5,066,592 A | 11/1991 | Huang et al. | |
| 5,493,007 A | * 2/1996 | Burnier et al. | |
| 5,612,311 A | * 3/1997 | Pierschbacher et al. | |
| 5,643,872 A | 7/1997 | Ali et al. | |
| 5,672,585 A | * 9/1997 | Pierschbacher et al. | |
| 5,827,821 A | * 10/1998 | Piersbacher et al. | |

FOREIGN PATENT DOCUMENTS

| | | | |
|---|---|---|---|
| CA | 2000048 | 4/1990 | |
| DE | 3831714 | 3/1990 | ........... C07K/13/00 |
| DE | 3841763 A1 | 6/1990 | |
| EP | 317053 | 5/1988 | |
| EP | 0275748 | 7/1988 | |
| EP | 314576 | 5/1989 | ........... C07K/5/10 |
| EP | 332523 | 9/1989 | ........... C12N/15/00 |
| EP | 338634 | 10/1989 | |
| EP | 0341915 | 11/1989 | |
| EP | 347931 | 12/1989 | ........... C07K/7/04 |
| EP | 368486 | 5/1990 | |
| EP | 382451 | 8/1990 | ........... C07K/7/10 |
| EP | 410537 | 1/1991 | ........... C07K/7/64 |
| EP | 410539 | 1/1991 | ........... C07K/7/06 |
| EP | 410540 | 1/1991 | ........... C07K/7/06 |
| EP | 410541 | 1/1991 | ........... C07K/7/06 |
| EP | 437367 | 7/1991 | |
| EP | 445796 | 9/1991 | |
| EP | 482649 | 4/1992 | |
| EP | 496327 | 7/1992 | |
| EP | 474273 | 11/1992 | |
| EP | 512829 | 11/1992 | |
| EP | 513810 | 11/1992 | |
| EP | 540334 | 5/1993 | |
| FR | 2617170 | 12/1988 | ........... C07K/7/06 |
| GB | 2207922 | 2/1989 | |
| JP | 1006217 | 1/1989 | ........... A61K/35/14 |
| JP | 3246299 | 11/1991 | |
| JP | 4134096 | 5/1992 | |
| JP | 4164095 | 6/1992 | |

(List continued on next page.)

OTHER PUBLICATIONS

Kopple et al., "Conformations of Aro–Guy–Asp. Containing Herrodetic Cyclid Peptides." J. Am. Chem. Sol. (1992) v. 114, pp. 9615–9623, 1992.*
Drickamer et al., J. Biol. Chem. 261:6878–6887 (1986).
Rauvala et al., J. Cell. Biol. 107:2293–2305 (1988).
Maes et al., Fed. Europ. Biochem. Soc. 241:41–45 (1988).
Moos et al., Nature 334:701–703 (1988).
Neurath et al., Mol. Immun. 27:539–549 (1990).
Kirchofer et al., J. Biol. Chem. 265:18525–18530 (1990).

(List continued on next page.)

*Primary Examiner*—Michael Borin
(74) *Attorney, Agent, or Firm*—Campbell & Flores LLP

(57) ABSTRACT

The invention provides cyclic peptides which inhibit platelet aggregation without causing prolonged bleeding time. The invention provides RGD or KGD containing peptides which are cyclized and contain hydrophobic amino acids adjacent to the carboxy terminus of the RGD sequence. Peptides of this nature are also provided which contain in addition to the hydrophobic amino acid an adjacent positively charged amino acid. Such peptides have a high affinity for the receptor IIb/IIIa and a low affinity for the fibronectin and vitronectin receptors. Such peptides can be administered in a suitable physiologically acceptable carrier to therapeutically treat thrombosis.

17 Claims, 26 Drawing Sheets

FOREIGN PATENT DOCUMENTS

| | | | |
|---|---|---|---|
| JP | 4213311 | 8/1992 | |
| JP | 4221396 | 8/1992 | |
| JP | 4221397 | 8/1992 | |
| JP | 4221400 | 8/1992 | |
| JP | 4235922 | 8/1992 | |
| JP | 4305597 | 10/1992 | |
| JP | 4327600 | 11/1992 | |
| WO | WO 88/03151 | 5/1988 | ............ C07K/7/00 |
| WO | WO 89/00200 | 1/1989 | |
| WO | WO 89/04837 | 6/1989 | |
| WO | WO 89/05155 | 6/1989 | ......... A61K/39/395 |
| WO | WO 89/05150 | 7/1989 | |
| WO | WO 89/07609 | 8/1989 | |
| WO | WO 90/00178 | 1/1990 | |
| WO | WO 90/02751 | 3/1990 | |
| WO | WO 90/06943 | 6/1990 | |
| WO | WO 90/14103 | 11/1990 | ......... A61K/39/395 |
| WO | WO 90/15620 | 12/1990 | |
| WO | WO 91/01331 | 2/1991 | |
| WO | WO 91/04031 | 4/1991 | .......... A61K/31/62 |
| WO | WO 91/05562 | 5/1991 | |
| WO | WO 91/07976 | 6/1991 | |
| WO | WO 91/11458 | 8/1991 | |
| WO | WO 91/15515 | * 10/1991 | ................ 530/321 |
| WO | WO 91/15516 | 10/1991 | |
| WO | WO92/00995 | 1/1992 | |
| WO | WO 92/07568 | 5/1992 | |
| WO | WO 92/07870 | 5/1992 | |
| WO | WO 92/08476 | 5/1992 | |
| WO | WO 92/08804 | 5/1992 | |
| WO | WO 92/10520 | 6/1992 | |
| WO | WO 92/13552 | 8/1992 | |
| WO | WO 92/17196 | 10/1992 | |
| WO | WO 92/17492 | * 10/1992 | ................ 530/317 |
| WO | WO 92/19595 | 11/1992 | |
| WO | WO 93/00095 | 1/1993 | |
| WO | WO 93/00108 | 1/1993 | |
| WO | WO 93/06232 | 4/1993 | |
| WO | WO 93/07169 | 4/1993 | |
| WO | WO 93/07867 | 4/1993 | |
| WO | WO 93/09133 | 5/1993 | |
| WO | WO 93/09795 | 5/1993 | |
| WO | WO 93/11229 | 6/1993 | |

OTHER PUBLICATIONS

Ratner et al., Nature 313:277–284 (1985).
Bond et al., Biochemistry 28:6110–6113 (1989).
Ohlstein et al., Thromb. Res. 46:576–585 (1987).
Harvey, J. Toxicol. —Toxin Reviews 3:91–137 (1984).
Dufton, CRC Crit. Rev. in Biochem. 14:113–171 (1983).
Olson, Nature 228:438–442 (1970).
Pelton, J. Med. Chem. 29:2370–2375 (1986).
Lebl, Collection Czechosloval Chem. Commun. 49:2680–2688 (1984).
Stanfield, J. Org. Chem. 51:5153–5156 (1986).
Barker, Protein Society 2nd Symposium (1987).
Gehlsen et al., J. Cell. Biol. 106:925–930 (1988).
Gehlsen et al., J. Cell. Biol. 105:3097–3104 (1987).
Siebers et al., Eur. J. Biochem. 178:131–140 (1988).
Ruoslahti et al., Cell 44:517–518 (1986).
Ruoslahti et al., Falk Symposium 43:239–244 (1987).
Bodanszky, Principles of Peptide Synthesis 217–222 (1984).
Marx, Science 248:1491–1493 (1990).
Creighton, Proteins 9 (1984).
Dayhoff, Atlas of Protein Sequences and Structure 5:89–99 (1972).
Joubert et al., Biochim. Biophys. Acta. 579:228–233 (1979).
Gan et al., J. Biol. Chem. 263(36):19827–19832 (1988).
Huang et al., J. Biol. Chem. 262(33):16157–16163 (1987).
Pelton et al., Proc. Natl. Acad. Sci. USA 82:236–239 (1985).
Plow et al., Blood 70:110–115 (1987).
Ruoslahti et al., J. Clin. Invest. 87:1–5 (1991).
Ali et al., Peptides Proc. 11th Amer. Peptide Symposium, La Jolla, CA, Marshall & Rivier, eds. (Jul. 9–14, 1989).
Garsky et al., Proc. Natl. Acad. Sci. USA 86:4022–4026 (1989).
Dennis et al., Proc. Natl. Acad. Sci. USA 87:2471–2475 (1989).
Chao et al., Proc. Natl. Acad. Sci. USA 86:8050–8054 (1989).
Shebuski et al., J. Biol. Chem. 264:21550–21556 (1989).
Huang et al., Biochemistry 28:661–666 (1989).
Spatola and Krzysztof, Tetrahedron 44(3):821–833 (1988).
Garo and Spatola, Biochem. Biophys. Res. Commun. 120(3):840–845 (1984).
Edwards and Spatola, Biochem. Biophys. Res. Commun. 136(2):730–736 (1986).
Spatola and Edwards, Biopolymers 25:S229–S244 (1986).
Davies et al., Biochem. Soc. Trans. 18:11326–11328 (1990).
Pierschbacher et al., Proc. Natl. Acad. Sci. USA 81:5985–5988 (1984).
Kloczewisk et al., Biochemistry 23:1767–1774 (1984).
Gartner and Bennett, J. Biol. Chem. 260:11891–11894 (1985).
Kleffer and Phillips, Annu. Rev. Cell Biol. 36:329–357 (1990).
Plow et al., Proc. Natl. Acad. Sci. USA 82:8057–8061 (1985).
Pytela et al., Proc. Natl. Acad. Sci. USA 82:5766–5770 (1985).
Pytela et al., Cell 40:191–198 (1985).
Pytela et al., Science 231:1559–1562 (1985).
Gardner et al, Cell 42:439–448 (1985).
Pierschbacher et al., Nature 309:30–33 (1984).
D'Souza et al., J. Biol. Chem. 263:3943–3951 (1988).
Parise et al., J. Biol. Chem. 262:12597–12602 (1987).
Haskei et al., Thromb. Res. 56:687–695 (1988).
Sakakibara et al., BBA 303:198–202 (1973).
Kaiser and Kezcy, Science 223:249–255 (1984).
Ohsaku et al., Int. J. Biol. Macromol. 6:234–240 (1984).
Cheresh, Chem. Abstract 104, abstract No. 183980c (1986).
Yamada, Chem. Abstract 107, abstract No. 5066p (1987).
Poole, Chem. Abstract 105, abstract No. 169400c (1986).
Toda et al., J. Cell. Biol. 105:3097–3104 (1987).
Singer et al., J. Cell. Biol. 104:573–584 (1987).
Lash et al., Dev. Biol. 123:411–420 (1987).
Pierschbacher and Ruoslahti, J. Biol. Chem. 262:17294–17298 (1987).
Haverstick et al., Blood 66:946–952 (1985).
Ruggeri et al., Proc. Natl. Acad. Sci. USA 83:5708–5712 (1986).
Ginsberg et al., J. Biol. Chem. 260:3931–3936 (1985).
Drickamer et al., J. Biol. Chem. 261:6878–6887 (1986).
Rauvala et al., J. Cell. Biol. 107:2293–2305 (1988).
Maes et al., Fed. Europ. Biochem. Soc. 241:41–45 (1988).
Moos et al., Nature 334:701–703 (1988).
Neurath et al., Mol. Immun. 27:539–549 (1990).
Kirchofer et al., J. Biol. Chem. 265:18525–18530 (1990).
Ratner et al., Nature 313:277–284 (1985).
Bond et al., Biochemistry 28:6110–6113 (1989).

Ohlstein et al., Thromb. Res. 46:576–585 (1987).
Harvey, J. Toxicol.—Toxin Reviews 3:91–137 (1984).
Dufton, CRC Crit. Rev. in Biochem. 14:113–171 (1983).
Olson, Nature 228:438–442 (1970).
Pelton, J. Med. Chem. 29:2370–2375 (1986).
Lebl, Collection Czechosloval Chem. Commun. 49:2680–2688 (1984).
Stanfield, J. Org. Chem. 51:5153–5156 (1986).
Barker, Protein Society 2nd Symposium (1987).
Gehlsen et al., J. Cell. Biol. 106:925–930 (1988).
Gehlsen et al., J. Cell. Biol. 105:3097–3104 (1987).
Siebers et al., Eur. J. Biochem. 178:131–140 (1988).
Ruoslahti et al., Cell 44:517–518 (1986).
Ruoslahti et al., Falk Symposium 43:239–244 (1987).
Bodanszky, Principles of Peptide Synthesis 217–222 (1984).
Marx, Science 248:1491–1493 (1990).
Creighton, Proteins 9 (1984).
Dayhoff, Atlas of Protein Sequences and Structure 5:89–99 (1972).
Joubert et al., Biochim. Biophys. Acta. 579:228–233 (1979).
Gan et al., J. Biol. Chem. 263(36):19827–19832 (1988).
Huang et al., J. Biol. Chem. 262(33):16157–16163 (1987).
Lam et al., J. Biol. Chem. 262:947–950 (1987).
Cadroy et al., J. Clin. Invest. 84:939–944 (1989).
Pelton et al., Proc. Natl. Acad. Sci. USA 82:236–239 (1985).
Plow et al., Blood 70:110–115 (1987).
Ruoslahti et al., J. Clin. Invest. 87:1–5 (1981).
Ali et al., Peptides Proc. 11th Amer. Peptide Symposium, La Jolla, CA, Marshall & Rivier, eds. (Jul. 9–14, 1989).
Garsky et al., Proc. Natl. Acad. Sci USA 86:4022–4026 (1989).
Dennis et al., Proc. Natl. Acad. Sci. USA 87:2471–2475 (1989).
Chao et al., Proc. Natl. Acad. Sci. USA 86:8050–8054 (1989).
Shebuski et al., J. Biol. Chem. 264:21550–21556 (1989).
Huang et al., Biochemistry 28:661–666 (1989).
Spatola and Krzysztof, Tetrahedron 44(3):821–833 (1988).
Garo and Spatola, Biochem. Biophys. Res. Commun. 120(3):840–845 (1984).
Edwards and Spatola, Biochem. Biophys. Res. Commun. 136(2):730–736 (1986).
Spatola and Edwards, Biopolymers 25:S229–S244 (1986).
Davies et al., Biochem. Soc. Trans. 18:11326–11328 (1990).
Pierschbacher et al., Proc. Natl. Acad. Sci. USA 81:5985–5988 (1984).
Kloczewisk et al., Biochemistry 23:1767–1774 (1984).
Gartner and Bennett, J. Biol. Chem. 260:11891–11894 (1985).
Kleffer and Phillips, Annu. Rev. Cell Biol. 36:329–357 (1990).
Plow et al., Proc. Natl. Acad. Sci USA 82:8057–8061 (1985).
Pytela et al., Proc. Natl. Acad. Sci. USA 82:5766–5770 (1985).
Pytela et al., Cell 40:191–198 (1985).
Pytela et al., Science 231:1559–1562 (1985).
Gardner et al, Cell 42:439–448 (1985).
Pierschbacher et al., Nature 309:30–33 (1984).

D'Souza et al., J. Biol. Chem. 263:3943–3951 (1988).
Parise et al., J. Biol. Chem. 262:12597–12602 (1987).
Haskei et al., Thromb. Res. 56:687–695 (1988).
Sakakibara et al., BBA 303:198–202 (1973).
Kaiser and Kezcy, Science 223:249–255 (1984).
Ohsaku et al., Int. J. Biol. Macromol. 6:234–240 (1984).
Cheresh, Chem. Abstract 104, abstract No. 183980c (1986).
Yamada, Chem. Abstract 107, abstract No. 5066p (1987).
Poole, Chem. Abstract 105, abstract No. 169400c (1986).
Toda, et al., J. Cell. Biol. 105:3097–3104 (1987).
Singer et al., J. Cell. Biol. 104:573–584 (1987).
Lash et al., Dev. Biol. 123:411–420 (1987).
Pierschbacher and Ruoslahti, J. Biol. Chem. 262:17294–17298 (1987).
Haverstick et al., Blood 66:946–952 (1985).
Ruggeri et al., Proc. Natl. Acad. Sci. USA 83:5708–5712 (1986).
Ginsberg et al., J. Biol. Chem. 260:3931–3936 (1985).
Schiller et al., "Synthesis of side–chain to side–chain cyclized peptide analogs on solid supports" *Int. J. Peptide Protein Res.* 25:171–177 (1985).
Felix et al., "Applications of BOP reagent in solid phase synthesis" *Int. J. Peptide Protein Res.* 31:231–238 (1988).
Felix et al., "Synthesis, biological activity and conformational analysis of cyclic GRF analogs" *Int. J. Peptide Protein Res.* 32:441–454 (1988).
Al–Obeidi et al., "Potent and prolonged acting cyclic lactamanalogues of α–melanotropin: design based on molecular dynamics" *J. Med. Chem.* 32:2555–2561 (1989).
Pytela et al., "Arginine–Glycine–Aspartic acid adhesion receptors" *Methods Enzymol.* 144:475–489 (1987).
Lipinska et al., "Fibrinogen heterogeneity in human plasma. Electrophoretic demonstration and characterization of two major fibrinogen components" *J. Lab. Clin. Med.* 84(4).509–516 (1974).
Yatohgo et al., "Novel purification of vitronectin from human plasma by heparin affinity chromatography" *Cell Structure and Function* 13:281–292 (1988).
Newman et al., "Quantitation of membrane glycoprotein IIIa on intact human platelets using the monoclonal antibody, AP–3" *Blood* 65(1):227–232 (1985).
Fitzgerald et al., "A method for purifying the platelet membrane glycoprotein IIb–IIIa complex" *Anal. Biochem.* 151:169–177 (1985).
Ledford et al., "A comparative study of three methods for the visualization of von Willebrand Factor (vWF) multimers" *Thrombosis and Hemostasis* 64(4):569–575 (1990).
Born, G.V.R., "Aggregation of blood platelets by adenosine diphosphate and its reversal" *Nature* 194:927–929 (1962).
Yim and Huffman, "A facile synthesis of β–(S–benzylmercapto)–β,β–cyclopentamethylene–propionic acid" *Int. J. Peptide Protein Res.* 21:568–570 (1983).
Solar and Schumaker, *J. Org. Chem.* 31:1996 (1966).
Engvall and Ruoslahti, "Binding of soluble form of fibroblast surface protein, fibronectin, to collagen" *Int. J. Cancer* 20:1–5 (1977).

* cited by examiner

FIG. 1
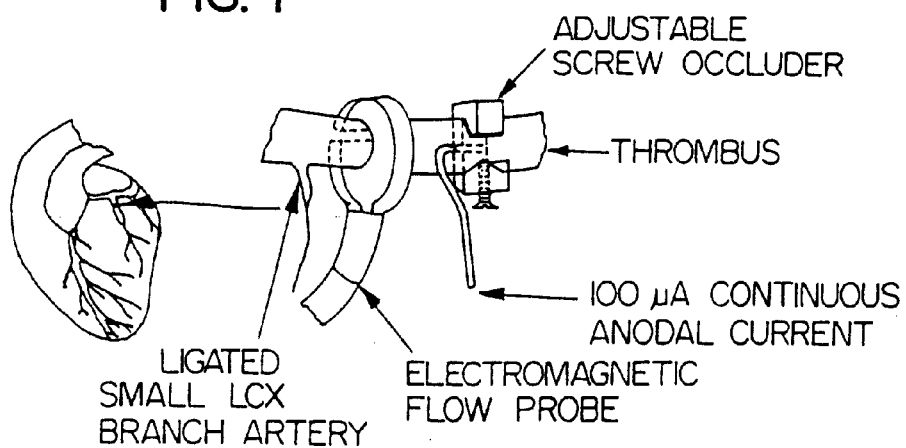
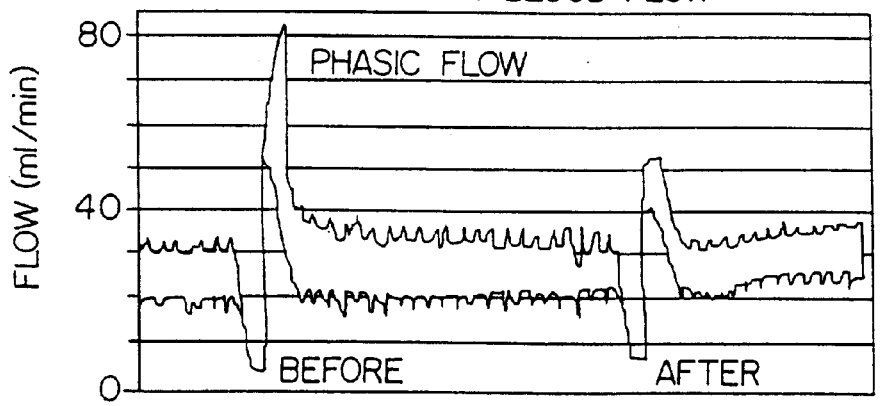

PEPTIDE PREVENTION OF CORONARY THROMBOSIS

| TREATMENT | TIME TO FULL OCCLUSION (min)[a] |
|---|---|
| Control | 136 ± 15 (13) |
| Analogue 10 mg/kg | 127 ± 41 (3) |
| Analogue 4Q | |
| 5 mg/kg | 165 ± 10 (2)[b] |
| 5 mg/kg (Low platelet count) | >300 (2) |
| 10 mg/kg | >300 (1)[c] |
| Analogue 4R | |
| 3 mg/kg | 95 (1) |
| 10 mg/kg | >300 (1)[c] |

[a] values are mean ± SEM for the number of determinations that appears in parentheses.

Statistical significance vs. control denoted as follows:

Effects of RGD Peptides on Hemodynamic Parameters

| Treatment | Mean Arterial Pressure (mm Hg) | Heart Rate (Beats/Min) | Platelet Count ($10^3$/ml) | Bleeding Time (Min) |
|---|---|---|---|---|
| ANALOGUE 2G | | | | |
| (10 mg/kg) (N=3) | | | | |
| Baseline | 104±5 | 160±10 | 480±12 | 2.9±0.6 |
| 1 hr. | 96±7 | 172±8 | 409±19 | 2.8±0.3 |
| 3 hr. | ND | ND | 395±36 | 2.6±0.1 |
| 5 hr. | ND | ND | 556±16 | 2.6±0.1 |
| ANALOGUE 4Q | | | | |
| (5 mg/kg) (N=2) | | | | |
| Baseline | 103±3 | 158±9 | 316±52 | 2.8±0.3 |
| 1 hr. | 107±6 | 160±10 | 406±185 | 2.8±0.3 |
| 3 hr. | 110±10 | 168±7 | 375±25 | 3.6±0.1 |
| 5 hr. | ND | ND | 355±47 | 3.0±0.5 |
| (10 mg/kg) (N=1) | | | | |
| Baseline | 100 | 162 | 307 | 4.0 |
| 1 hr. | 104 | 170 | 420 | 7.5 |
| 3 hr. | 105 | 160 | 379 | 5.5 |
| 5 hr. | 107 | 165 | 290 | 5.5 |
| ANALOGUE 4R | | | | |
| (3 mg/kg) (N=1) | | | | |
| Baseline | 103 | 170 | 393 | 4.0 |
| 1 hr. | 110 | 165 | 367 | 4.0 |
| 3 hr. | ND | ND | 420 | 4.0 |
| 5 hr. | ND | ND | 575 | 5.0 |
| (10 mg/kg) (N=1) | | | | |
| Baseline | 100 | 162 | 512 | 4.0 |
| 1 hr. | 95 | 168 | 513 | 5.0 |
| 3 hr. | 102 | 172 | 491 | 5.0 |
| 5 hr. | 107 | 170 | 460 | 5.0 |

FIG. 5

PEPTIDE EFFECTS ON ANIMAL HEMATOLOGY & BLEEDING TIMES
(Experiment 1)

| HEMATOLOGY PARAMETERS | SHUNT 1 | | | SHUNT 2 | | |
|---|---|---|---|---|---|---|
| | 0 Hr. | 2 Hr. | 0 Hr. | 1 Hr. | 2 Hr. |
| Red Blood Cells (M/UL) | 4.78 | 4.00 | 4.49 | 4.70 | 4.11 |
| White Blood Cells (K/UL) | 9.3 | 4.0 | 12.0 | 11.4 | 8.8 |
| Platelets (K/UL) | 332 | 250 | 269 | 276 | 231 |
| Hematocrit (%) | 42 | 35 | 39 | 41 | 36 |
| Hemoglobin (G/UL) | 12.5 | 10.7 | 12.0 | 12.4 | 10.6 |
| Bleeding Time* (Min) | 4:48 | 4:55 | ND | 5:02 | 3:05 |
| Clotting Time (Sec) | 120 | 130 | ND | ND | 124 |

*Represents average of two simultaneous determinations.

ND = not determined.

FIG. 8

PEPTIDE EFFECTS ON ANIMAL HEMATOLOGY & BLEEDING TIMES
(Experiment 2)

| HEMATOLOGY PARAMETERS | SHUNT 1 | | | SHUNT 2 | | |
|---|---|---|---|---|---|---|
| | 0 Hr. | 2 Hr. | 0 Hr. | 1 Hr. | 2 Hr. |
| Red Blood Cells (M/UL) | 4.78 | 5.12 | 5.06 | 4.65 | 4.81 |
| White Blood Cells (K/UL) | 6.6 | 12.9 | 10.7 | 10.0 | 10.7 |
| Platelets (K/UL) | 274 | 281 | 281 | 264 | 286 |
| Hematocrit (%) | 39 | 41 | 41 | 37 | 38 |
| Hemoglobin (G/UL) | 12.3 | 13.2 | 12.9 | 12.0 | 12.4 |
| Bleeding Time* (Min) | 4:15 | 4:27 | ND | 4:46 | 4:05 |
| Clotting Time (Sec) | 131 | 125 | ND | ND | 132 |

*Represents average of two simultaneous determinations.
ND = not determined.

FIG. 11

IN VIVO AND EX VIVO EVALUATION OF PEPTIDES IN A RABBIT MODEL

| CODE | Rabbit BT CBT Ratio | Rabbit Ex Vivo Plt Aggn % Inh | Rabbit PBF | Dose B01 + Inf | N | Sequence |
|---|---|---|---|---|---|---|
| Control | 1.1 | 11 | Normal | (Saline) | 2 | |
| 8X | 0.7 | 94 | Normal | 1.5+0.036 | 1 | Ac-CNPRGD(Y-OMe)RC-NH2 |
| 8X | 2.1 | 98 | Normal | 4.5+0.108 | 1 | |
| 11J | 0.93 (dose too low) | 17 | Normal | 1.5+0.036 | 1 | Ac-CNPRGD(Y-OMe)EC-NH2 |
| 11K | 0.69 (dose too low) | 29 | Normal | 1.5+0.036 | 1 | Ac-CNPRGD(Y-OMe)AC-NH2 |
| 11L | 1.09 (dose too low) | 12 | Normal | 1.5+0.036 | 1 | Ac-CNPRGD(Y-OMe)(dR)C-NH2 |
| 11P | 1.42 (dose too low) | 10 | Normal | 1.5+0.036 | 1 | Ac-CNPRGD(Y-OMe)OC-NH2 |
| 11Q | 0.70 (dose too low) | 63 | Normal | 1.5+0.036 | 1 | Ac-CNPRGD(Y-OMe)RC-NH2 |
| 11R | 1.40 (dose too low) | 19 | Normal | 1.5+0.036 | 1 | Ac-CNPRGD(Y-OMe)KC-NH2 |
| 11S | 1.00 (dose too low) | 10 | Normal | 1.5+0.036 | 1 | Ac-CNPRGD(Y-OMe)(Cit)C-NH2 |
| 11V | 1.17 (dose too low) | 0 | Normal | 1.5 + 0.036 | 1 | Ac-CNPRGD(Y-OMe)(Nle)C-NH2 |
| 4Q | 1.4 | 97 | Decreased | 3.75+0.090 | 2 | RPenGHRGDWRCR |
| 4Q | 1.4 | 99 | Decreased | 11.4+0.270 | 1 | |
| 5O | 1.3 | 27 | ND | 0.27+0.007 | 1 | RPmcGHRGD(Y-OMc)RCR |
| 5O | 0.75 | 93 | Decreased | 1.5+0.036 | 1 | |
| 7B | 1.2 | 32 | ND | 0.59+0.014 | 1 | RPmcGHRGD(p-1-F)RCR |
| 7B | 1.0 | 96 | Decreased | 3.0+0.072 | 2 | |
| 7T | 1.1 | 94 | Decreased | 1.5+0.036 | 2 | RPmcGHRGD(p-NO2-F)RCR |

Dose of [mg/kg] bolus + [mg/kg/min x 60 min] infusion

FIG. 12

|     | Sequence | Platelet Aggr. Citrate (μM) | Platelet Aggr. Heparin (μM) |
| --- | --- | --- | --- |
| 8X  | Ac-CNPRGD (O-Me-Y) RC-NH$_2$ | 0.22 | 3.40 |
| 17I | GRGD (O-Me-Y) RE-NH$_2$ | 0.69 | 16.7 |
| 21I | RGD (O-Me-Y) RE-NH$_2$ | 0.08 | 0.82 |

FIG. 14

Potencies of cyclic (lactam) RGD peptide analogues
Against Platelet Aggregation and Receptor Binding

| | Sequence | ADP-Stimulated Platelet Aggregation (IC$_{50}$ in μM, Citrated Blood) | ADP-Stimulated Platelet Aggregation (IC$_{50}$ in μM, Heparinized Blood) | FNR Binding (μM) | VNR Binding (μM) | IIb/IIIa Binding (μM) |
|---|---|---|---|---|---|---|
| 18G | (β-Ala) RGD (O-Me-Y) RD-NH$_2$ | 0.22 | 2.8 | 1.64 | 9.85 | 0.01 |
| 17I | GRGD (O-Me-Y) RE-NH$_2$ | 0.69 | 16.7 | 10.0 | 7.53 | 0.032 |
| 18J | (β-Ala) NPRGD (O-Me-Y) RD-NH$_2$ | 2.99 | 5.09 | 10.0 | 10.0 | 0.23 |
| 17J | GNPRGD (O-Me-Y) RE-NH$_2$ | 0.46 | 8.45 | 10.0 | 4.83 | 0.024 |
| 20M | GRGD (O-n-butyl-Y) RE-NH$_2$ | 1.50 | 35.00 | | | |
| 20Q | GNPRGD (O-Me-Y) RD-NH$_2$ | 0.16 | 2.10 | | | |
| 21I | RGD (O-Me-Y) RE-NH$_2$ | 0.08 | 0.82 | | | |
| 23E | GNPRGD (O-n-butyl-Y) RE-NH$_2$ | 1.47 | 13.6 | | | |

FIG.15

Potencies of cyclic RGD peptide analogues against platelet aggregation and receptor binding

| | Sequence | ADP-Stimulated Platelet Aggregation (IC50 in µM Citrated Blood) | ADP-Stimulated Platelet Aggregation (IC50 in µM Heparinized Blood) | FNR Binding (µM) | VNR Binding (µM) | IIb/IIIa Binding (µM) |
|---|---|---|---|---|---|---|
| 13Q | AcCRGD (O-Me-Y) RC-OH | 0.27 | 3.60 | 5.20 | 1.70 | 0.0094 |
| 14T | AcCRGD (O-Me-Y) R (Pen)-NH2 | 0.46 | 3.20 | 1.70 | 0.35 | 0.05 |
| 14U | Ac (dPen) RGD (O-Me-Y) RC-NH2 | 1.70 | 13.00 | 9.30 | 7.30 | 0.63 |
| 14V | AcCKGD (O-Me-Y) RC-NH2 | 0.61 | 13.00 | 10.00 | 10.00 | 0.074 |
| 14S | AcCRGD (O-Me-Y) P (Pen)-R-NH2 | 1.30 | 2.60 | 0.057 | 0.024 | 0.0030 |
| 14Z | AcCRGD (O-Me-Y) R (dPen)-NH2 | 1.60 | 34.00 | 0.35 | 3.00 | 0.098 |
| 15V | AcCRGD (O-Me-Y) RC-NH2 | 0.34 | 3.90 | 4.90 | 7.04 | 0.016 |
| 15W | AcCRGD (O-Me-Y) RC-R-NH2 | 0.29 | 3.20 | 3.20 | 6.24 | 0.014 |
| 16A | (Mpr) RGD (O-Me-Y) RC-NH2 | 0.12 | 2.00 | 3.50 | 4.30 | 0.016 |
| 17Z | (Mpr) RGD (O-n-butyl-Y) RC-NH2 | 1.10 | 17.00 | 1.74 | 1.28 | 0.87 |
| 17Y | (Mpr) KGD (O-Me-Y) RC-NH2 | 1.10 | 14.1 | 10.00 | 10.00 | 0.14 |
| 17O | (Pmp) RGD (O-Me-Y) RC-NH2 | 0.20 | 2.40 | 7.70 | 10.00 | 0.038 |
| 17Q | AcCRGD (O-n-butyl-Y) RC-NH2 | 1.40 | 24.00 | 1.70 | 0.73 | 0.23 |
| 17V | AcCRGD (Hpa) RC-NH2 | 1.40 | 21.00 | 0.54 | 5.00 | 0.84 |
| 18F | Ac-RGD (O-n-butyl-Y) R-NH2 | 34.00 | 200.0 | 5.40 | 9.30 | 5.40 |
| 22I | Ac-C(N-Me-R) GD (Pen)-R-NH2 | 0.068 | 0.5 | | | |
| 13G | Ac (dPen) HRGD (O-Me-Y) RC-NH2 | 0.17 | 7.30 | 8.50 | 2.60 | 0.13 |

FIG.16

Modifications of G(Pen)GHRGDLRCA

| No. | Peptide[a,b] | Platelet Aggregation human PRP/ADP IC$_{50}$ (μM) | $\alpha_{IIb}\beta_3$ ELISA IC$_{50}$ (μM) | $\alpha_5\beta_1$ ELISA IC$_{50}$ (μM) | $\alpha_v\beta_5$ ELISA IC$_{50}$ (μM) |
|---|---|---|---|---|---|
| 1 | G(Pen)GHRGDLRCA | 13.7 | 3.44 | 3.44 | 8.26 |
| 2 | G(D-Pen)GHRGDLRCA | 7.1 | 0.15 | 1.38 | 5.27 |
| 3 | R(Pen)GHRGDLRCR | 9.6 | 0.04 | nt[b] | 4.93 |
| 4 | R(D-Pen)GHRGDLRCR | 4.1 | 0.15 | 0.10 | 10.00 |
| 5 | R(Pmc)GHRGDLRCR | 3.0 | 0.40 | 5.19 | 1.58 |
| 6 | (Pmp)GHRGDLRCA | 5.9 | 0.02 | 0.83 | 10.00 |
| 7 | R(Tmc)GHRGDLRCR | 4.1 | 0.03 | 1.20 | 0.34 |

FIG. 17

Modifications of R(Pmc)GHRGDLRCR

| No. | Peptide[a,b] | Platelet Aggregation human PRP/ADP IC$_{50}$ ($\mu M$) | $\alpha_{IIb}\beta_3$ ELISA IC$_{50}$ ($\mu M$) | $\alpha_5\beta_1$ ELISA IC$_{50}$ ($\mu M$) | $\alpha_v\beta_5$ ELISA IC$_{50}$ ($\mu M$) |
|---|---|---|---|---|---|
| 5 | R(Pmc)GHRGDLRCR | 3.00 | 0.40 | 5.19 | 1.58 |
| 8 | R(Pmc)GHRGDVRCR | 0.69 | 0.15 | 2.30 | 2.00 |
| 9 | R(Pmc)GHRGDFRCR | 0.62 | 0.04 | 8.70 | 10.00 |
| 10 | R(Pmc)GHRGDYRCR | 0.97 | 0.15 | 10.00 | 7.85 |
| 11 | R(Pmc)GHRGD(Y-OMe)RCR | 0.56 | 0.02 | 0.98 | 1.05 |
| 12 | R(Pmc)GHRGD(p-I-F)RCR | 0.70 | 0.01 | 4.19 | 4.03 |
| 13 | R(Pmc)GHRGD(p-Cl-F)RCR | 0.73 | 0.02 | 0.87 | 15.30 |
| 14 | R(Pmc)GHRGD(Y-O-n-butyl)RCR | 0.35 | 0.03 | 6.60 | 2.20 |
| 15 | R(Pmc)GHRGD(Phg)RCR | 0.68 | 0.02 | 1.23 | 0.79 |
| 16 | R(Pmc)GHRGD(Hpa)RCR | 0.60 | 0.02 | 1.81 | 4.25 |
| 17 | R(Pmc)GHRGD(2-Nal)RCR | 0.44 | 0.07 | 7.72 | 10.00 |

FIG. 18

Modifications of R(Pmc)GHRGD(Y-OMe)RCR

| No. | Peptide[a,b] | Platelet Aggregation human PRP/ADP IC$_{50}$ ($\mu$M) | $\alpha_{IIb}\beta_3$ ELISA IC$_{50}$ ($\mu$M) | $\alpha_5\beta_1$ ELISA IC$_{50}$ ($\mu$M) | $\alpha_v\beta_5$ ELISA IC$_{50}$ ($\mu$M) |
|---|---|---|---|---|---|
| 11 | R(Pmc)GHRGD(Y-OMe)RCR | 0.56 | 0.02 | 0.98 | 1.05 |
| 18 | R(Pmc)DHRGD(Y-OMe)RCR | 2.75 | 0.21 | 9.20 | 7.20 |
| 19 | R(Pmc)SHRGD(Y-OMe)RCR | 0.95 | 0.12 | >10.00 | 6.60 |
| 20 | R(Pmc)IHRGD(Y-OMe)RCR | 0.83 | 0.06 | 6.40 | 9.90 |
| 21 | R(Pmc)NHRGD(Y-OMe)RCR | 0.99 | 0.09 | 4.70 | 6.90 |
| 22 | R(Pmc)RHRGD(Y-OMe)RCR | 0.44 | 0.07 | 7.72 | 6.20 |

FIG.19

Modifications of R(Pmc)GHRGD(Y-OMe)RCR

| No. | Peptide[a,b] | Platelet Aggregation human PRP/ADP IC$_{50}$ (μM) | $α_{IIb}β_3$ ELISA IC$_{50}$ (μM) | $α_5β_1$ ELISA IC$_{50}$ (μM) | $α_vβ_5$ ELISA IC$_{50}$ (μM) |
|---|---|---|---|---|---|
| 11 | R(Pmc)GHRGD(Y-OMe)RCR | 0.56 | 0.02 | 0.98 | 1.05 |
| 23 | R(Pmc)G(dH)RGD(Y-OMe)RCR | 0.40 | 0.01 | 6.8 | nt[c] |
| 24 | R(Pmc)GYRGD(Y-OMe)RCR | 0.85 | 0.03 | 8.5 | 8.80 |
| 25 | R(Pmc)G(dY)RGD(Y-OMe)RCR | 0.52 | 0.01 | 10.0 | 10.00 |
| 26 | R(Pmc)GPRGD(Y-OMe)RCR | 0.54 | 0.01 | 7.2 | 1.70 |

FIG. 20

Modifications of Ac-CIPRGD(Y-OMe)RC-NH$_2$

| No. | Peptide[a] | Platelet Aggregation human PRP/ADP IC$_{50}$ ($\mu$M) | $\alpha_{IIb}\beta_3$ ELISA IC$_{50}$ ($\mu$M) | $\alpha_5\beta_1$ ELISA IC$_{50}$ ($\mu$M) | $\alpha_v\beta_5$ ELISA IC$_{50}$ ($\mu$M) |
|---|---|---|---|---|---|
| 27 | Ac-CIPRGD(Y-OMe)RC-NH$_2$ | 0.17 | 0.003 | 4.30 | 5.80 |
| 28 | Ac-CIPRGDYRC-NH$_2$ | 0.33 | 0.003 | 4.50 | >10.00 |
| 29 | Ac-CIPRGDFRC-NH$_2$ | 0.45 | 0.014 | 2.10 | 10.00 |
| 30 | Ac-CIPRGD(Y-O-n-butyl)RC-NH$_2$ | 0.48 | 0.016 | 6.00 | >10.00 |
| 31 | Ac-CIPRGD(p-NO$_2$-F)RC-NH$_2$ | 0.21 | 0.430 | 1.20 | 4.30 |
| 32 | Ac-CNPRGD(Y-OMe)RC-NH$_2$ | 0.22 | 0.029 | 8.20 | 4.70 |
| 33 | Ac-CNPRGD(Y-OEt)RC-NH$_2$ | 0.22 | 0.004 | 10.00 | 8.40 |
| 34 | Ac-CNPRGD(Y-O-n-butyl)RC-NH$_2$ | 0.10 | 0.006 | 1.50 | 10.00 |
| 35 | Ac-CNPRGD(p-NO$_2$-F)RC-NH$_2$ | 0.84 | 0.017 | 4.79 | 4.80 |

Modifications of Ac-CNPRGD(Y-OMe)RC-NH$_2$

| No. | Peptide[a] | Platelet Aggregation human PRP/ADP IC$_{50}$ ($\mu$M) | $\alpha_{IIb}\beta_3$ ELISA IC$_{50}$ ($\mu$M) | $\alpha_5\beta_1$ ELISA IC$_{50}$ ($\mu$M) | $\alpha_v\beta_5$ ELISA IC$_{50}$ ($\mu$M) |
|---|---|---|---|---|---|
| 32 | Ac-CNPRGD(Y-OMe)RC-NH$_2$ | 0.22 | 0.029 | 8.20 | 4.70 |
| 36 | Ac-(D-Pen)NPRGD(Y-OMe)RC-NH$_2$ | 0.17 | 0.001 | 6.80 | 6.70 |
| 37 | Ac-(Pmc)NPRGD(Y-OMe)RC-NH$_2$ | 0.15 | 0.016 | >10.00 | 2.34 |
| 38 | (Pmp)NPRGD(Y-OMe)RC-NH$_2$ | 0.17 | 0.031 | 5.10 | 4.90 |
| 39 | (Mpr)NPRGD(Y-OMe)RC-NH$_2$ | 0.17 | 0.015 | 6.00 | 3.00 |
| 27 | Ac-CIPRGD(Y-OMe)RC-NH$_2$ | 0.17 | 0.003 | 4.30 | 5.80 |
| 40 | Ac-(D-Pen)IPRGD(Y-OMe)RC-NH$_2$ | 0.28 | 0.002 | 4.30 | 4.30 |

FIG. 23

Modification of Ac-CNPRGD(Y-OMe)RC-NH₂

| No. | Peptide[a] | Platelet Aggregation human PRP/ADP IC$_{50}$ (μM) | $\alpha_{IIb}\beta_3$ ELISA IC$_{50}$ (μM) | $\alpha_5\beta_1$ ELISA IC$_{50}$ (μM) | $\alpha_v\beta_5$ ELISA IC$_{50}$ (μM) |
|---|---|---|---|---|---|
| 32 | Ac-CNPRGD(Y-OMe)RC-NH₂ | 0.22 | 0.029 | 8.20 | 4.70 |
| 41 | Ac-CNPRGD(Y-OMe)KC-NH₂ | 1.0 | 0.038 | 1.56 | 5.82 |
| 42 | Ac-CNPRGD(Y-OMe)EC-NH₂ | 3.4 | 0.020 | 6.24 | 9.47 |
| 43 | Ac-CNPRGD(Y-OMe)AC-NH₂ | 4.5 | 0.050 | 0.84 | 8.85 |
| 44 | Ac-CNPRGD(Y-OMe)(D-R)C-NH₂ | 7.3 | 0.220 | >10.00 | >10.00 |
| 45 | Ac-CNPRGD(Y-OMe)OC-NH₂ | 4.9 | 0.050 | 0.44 | 7.7 |
| 46 | Ac-CNPRGD(Y-OMe)(Cit)C-NH₂ | 7.5 | 0.352 | 0.44 | 3.46 |
| 47 | Ac-CNPRGD(Y-OMe)LC-NH₂ | 7.6 | 0.248 | >10.00 | 7.14 |

Peptide Effect on Template Bleeding Time

| No. | Peptide | Bleeding Times[a,b] (Minutes) |
|---|---|---|
| 32 | Ac-CNPRGD(Y-OMe)RC-NH$_2$ | 3.0 (5.5)[b] |
| 42 | Ac-CNPRGD(Y-OMe)EC-NH$_2$ | >30 |
| 43 | Ac-CNPRGD(Y-OMe)AC-NH$_2$ | >30 |
| 47 | Ac-CNPRGD(Y-OMe)LC-NH$_2$ | 21 |
| 48 | Ac-CNPKGD(Y-OMe)RC-NH$_2$ | 3.5 |

METHOD AND COMPOSITION FOR TREATING THROMBOSIS

This application is a continuation of application Ser. No. 08/171,068, filed Dec. 20, 1993, (now abandoned) which is a continuation-in-part of application Ser. No. 08/079,441, filed Jun. 18, 1993, (now abandoned) which is a continuation-in-part of application Ser. No. 08/050,736, filed Apr. 14, 1993, (now abandoned) which is a continuation-in-part of application Ser. No. 07/681,119, filed Apr. 5, 1991, (now abandoned) which is a continuation-in-part of application Ser. No. 07/506,444, filed April 6, 1990 (now abandoned).

BACKGROUND OF THE INVENTION

The invention relates generally to methods of treating thrombosis, and, more particularly, to such methods using peptides.

The formation of a blood clot within a blood vessel, a process termed thrombosis, is a serious condition which can cause tissue damage and, if untreated, eventually lead to death. Thrombotic formation is dependent upon platelet aggregation. The interaction of blood platelets with the endothelial surface of injured blood vessels and with other platelets is a major factor in the course of development of clots or thrombi.

Various products to prevent formation of such clots are now available, such as asparin, dipyridamole and heparin. These products generally kill or remove platelets, which can eliminate the clot but has the potential serious side effect of causing prolonged bleeding. Moreover, the effect of such products can only be reversed by new platelets being formed or provided.

Platelet aggregation is dependent upon the binding of fibrinogen and other serum proteins to the glycoprotein receptor IIb/IIIa complex on the platelet plasma membrane. GP IIb/IIIa is a member of a large family of cell adhesion receptors known as integrins, many of which are known to recognize an Arg-Gly-Asp (RGD) tripeptide recognition sequence. One hypothesis for the specificity of interactions between the various receptors and the RGD-containing peptides is that individual receptor specificity is determined by the conformation that the RGD sequence adopts in each individual ligand. Alternatively, the nature of residues flanking the RGD sequence could influence receptor affinity, receptor selectivity and other biological properties.

Inhibition of GP IIb/IIIa receptor binding, and therefore of platelet aggregation, without inhibition of other cell adhesion receptors would be necessary for the prevention of coronary thrombosis. There thus exists a need for a composition able to specifically inhibit the platelet aggregation receptor GP IIb/IIIa and to dissolve blood clots without removing or killing platelets and without causing detrimental side effects such as prolonged bleeding. The present invention satisfies this need and provides related advantages as well.

SUMMARY OF THE INVENTION

The invention provides cyclic RGD or KGD containing peptides which inhibit platelet aggregation without causing prolonged bleeding time. Typically these peptides contain hydrophobic amino acids adjacent to the carboxy terminus of the RGD or KGD sequence. Peptides of this nature are also provided which contain in addition to the hydrophobic amino acid an adjacent positively charged amino acid. Such peptides have a high affinity for the IIb/IIIa receptor and a low affinity for the fibronectin and vitronectin receptors. Such peptides can be administered in a suitable physiologically acceptable carrier to therapeutically treat thrombosis.

Additionally, the invention provides RGD or KGD containing cyclic peptides which do not have a hydrophobic amino acid adjacent to the carboxy terminus.

BRIEF DESCRIPTION OF THE DRAWINGS

FIG. 1 illustrates the insertion of electromagnetic flow probe, intra-coronary electrode and screw occluder into the left circumflex coronary artery (upper) and shows coronary blood flow before and after adjustment of the critical stenosis (lower).

FIG. 4 shows the effects of the peptides injected in Example VII on coronary blood flow and thrombosis.

FIG. 5 shows the effects of the peptides injected in Example VII on hemodynamic responses.

FIG. 8 shows the hematology parameters in animal 1 for control treatment (shunt 1) and for treatments with the peptide of Example VIII (shunt 2).

FIG. 11 shows the hematology parameters in animal 2 for control treatment (shunt 1) and for treatments with the peptide of Example VIII (shunt 2).

FIG. 12 shows the in vivo and ex vivo efficacy of various hydrophobically enhanced peptides in a rabbit model.

FIG. 14 shows the platelet aggregation $IC_{50}$ values of 21I, 17I and 8× peptides in citrated and heparinized blood.

FIG. 15 shows the potencies of cyclic (lactam) RGD peptide analogues against platelet aggregation and receptor binding as described in Example XI.

FIG. 16 shows the potencies of linear and cyclic RGD peptide analogues against platelet aggregation and receptor binding as described in Example XI.

FIG. 17 is a Table showing the effect of modifications of Pen residue at position −3 (as defined, infra) on potency and selectivity. Symbols and standard abbreviations are as recommended by the IUPAC-IUB Joint Commission on Biochemical Nomenclature (JCBN) (*Biochem. J.* (1984) 219:345 and *Europ. J. Biochem.* (1984) 138:9, each incorporated herein by reference. Additional abbreviations are as follows: AAA, amino acid analysis Boc, tert-butoxycarbonyl; Cit, Citrulline; DCM, dichloromethane; ELISA, enzyme-linked immunosorbent assay; FABMS, fast atom bombardment mass spectrum; HOBT, N-Hydroxybenzoltriazole; Hpa, homophenylalanine; Mpr, β-mercaptopropionic acid; 2-Nal, β-(2-naphthyl)-alanine;

Figure 2A:
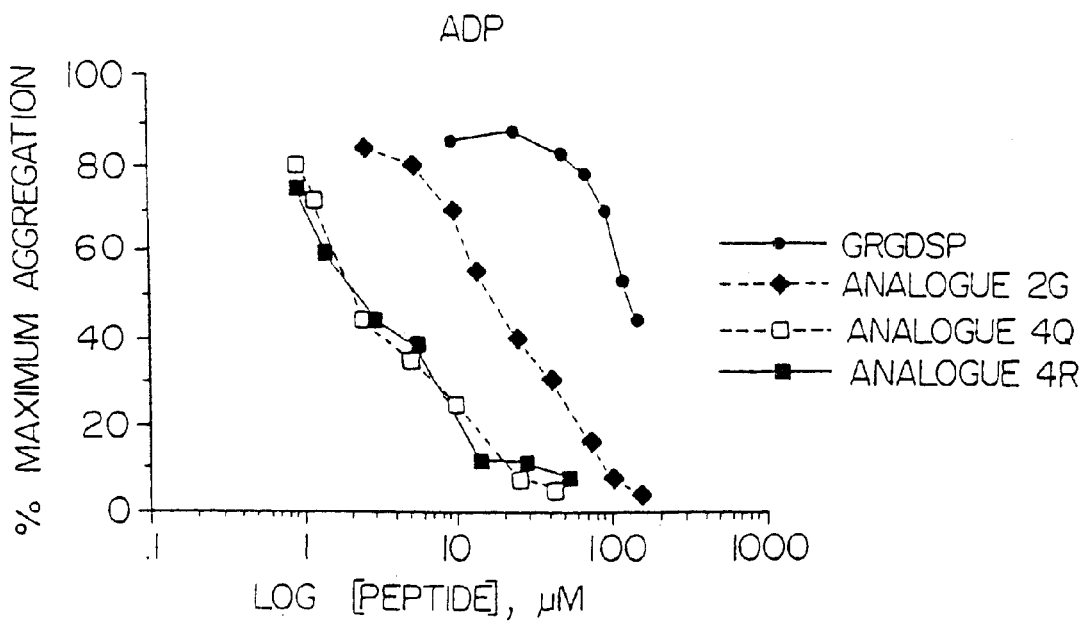
FIG. 2 is a dose-response analysis of the relative anti-aggregation potencies of the peptides injected in Example VII.

Pen, penicillamine; Pgl, phenylglycine; Pmc, β,β-pentamethylenecysteine; Pmp, β,β-pentamethylene-β-mercaptopropionicacid; TLC, thin-layer chromatography; Tmc, β,β-tetramethylenecysteine; p-I-F, p-iodo-phenylalanine; p-Cl-F, p-chloro-phenylalanine; p-NO$_2$-F, p-nitro-phenylalanine, Y-OMe, O-methyltyrosine; Y-O-n-butyl, O-n-butyl-tyrosine. b=not tested.

FIG. 18 (SEQ ID NOS. 145, 65–67, 1, 133, 146, 63, 69, 61 and 62, respectively) is a Table summarizing the result of substitution at position 3 (as defined, infra) of peptide R(Pmc)GHRGDLRCR. Symbols and standard abbreviations for amino acids are as recommended by the IUPAC-IUB Joint Commission on Biochemical Nomenclature (JCBN) (*Biochem. J.* (1984) 219:345 and *Europ. J. Biochem.* (1984) 138:9, each incorporated herein by reference. Additional abbreviations are as follows: AAA, amino acid analysis Boc, tert-butoxy-carbonyl; Cit, Citrulline; DCM, dichloromethane; ELISA, enzyme-linked immunosorbent assay; FABMS, fast atom bombardment mass spectrum; HOBT, N-Hydroxy-benzoltriazole; Hpa, homophenylalanine; Mpr, β-mercaptopropionic acid; 2-Nal, β-(2-naphthyl)-alanine; Pen, penicillamine; Pgl, phenylglycine; Pmc, β,β-pentamethylenecysteine; Pmp, β,β-pentamethylene-β-mercaptopropionicacid; TLC, thin-layer chromatography; Tmc, β,β-tetramethylenecysteine; p-I-F, p-iodo-phenylalanine; p-Cl-F, p-chloro-phenylalanine; p-NO$_2$-Ff p-nitro-phenylalanine, Y-OMe, O-methyltyrosine; Y-O-n-butyl, O-n-butyl-tyrosine. Peptide 5 and peptides 8–17 were prepared by employing Boc-D,L-Pmc(4-MeBzl).

FIG. 19 (SEQ ID NOS. 1, 147–149, 76 and 68, respectively) is a Table summarizing the effect of substitutions in position −2 (as defined, infra) of peptide R(Pmc)GHRGD(Y-OMe)RCR (SEQ ID NO. 1). Symbols and standard abbreviations for amino acids are as recommended by the IUPAC-IUB Joint Commission on Biochemical Nomenclature (JCBN) (*Biochem. J.* (1984) 219:345 and *Europ. J. Biochem.* (1984) 138:9, each incorporated herein by reference. Additional abbreviations are as follows: AAA, amino acid analysis Boc, tert-butoxy-carbonyl; Cit, Citrulline; DCM, dichloromethane; ELISA, enzyme-linked immunosorbent assay; FABMS, fast atom bombardment mass spectrum; HOBT, N-Hydroxy-benzoltriazole; Hpa, homophenylalanine; Mpr, β-mercaptopropionic acid; 2-Nal, β-(2-naphthyl)-alanine; Pen, penicillamine; Pgl, phenylglycine; Pmc, β,β-pentamethylenecysteine; Pmp, β,β-pentamethylene-β-mercaptopropionicacid; TLC, thin-layer chromatography; Tmc, β,β-tetramethylenecysteine; p-I-F, p-iodo-phenylalanine; p-Cl-F, p-chloro-phenylalanine; p-NO$_2$-F, p-nitro-phenylalanine, Y-OMe, O-methyltyrosine; Y-O-n-butyl, O-n-butyl-tyrosine. Peptides 18 to 22 as shown in this Table were prepared by employing Boc-D,L-Pmc(4-MeBzl).

FIG. 20 (SEQ ID NOS. 1 and 150–153, respectively) is a Table summarizing the effect of modifications at position −1 (as defined, infra) in peptide R(Pmc)GHRGD(Y-OMe)RCR. Symbols and standard abbreviations for amino acid are as recommended by the IUPAC-IUB Joint Commission on Biochemical Nomenclature (JCBN) (*Biochem. J.* (1984) 219:345 and *Europ. J. Biochem.* (1984) 138:9, each incorporated herein by reference. Additional abbreviations are as follows: AAA, amino acid analysis Boc, tert-butoxy-carbonyl; Cit, Citrulline; DCM, dichloromethane; ELISA, enzyme-linked immunosorbent assay; FABMS, fast atom bombardment mass spectrum; HOBT, N-Hydroxy-benzoltriazole; Hpa, homophenylalanine; Mpr, β-mercaptopropionic acid; 2-Nal, β-(2-naphthyl)-alanine; Pen, penicillamine; Pgl, phenylglycine; Pmc, β,β-pentamethylenecysteine; Pmp, β,β-pentamethylene-β-mercaptopropionicacid; TLC, thin-layer chromatography; Tmc, β,β-tetramethylenecysteine; p-I-F, p-iodo-phenylalanine; p-Cl-F, p-chloro-phenylalanine; p-NO$_2$-F, p-nitro-phenylalanine, Y-OMe, O-methyltyrosine; Y-O-n-butyl, O-n-butyl-tyrosine. Peptides 23 through 26 were prepared by employing Boc-D,L-Pmc(4-MeBzl). Nt means not tested.

FIG. 21 (SEQ ID NOS. 2, 154–157, 3, 158, 16 and 159, respectively) is a Table showing the effect of modifications of hydrophobic amino acid at position 3 (as defined, infra) in peptides Ac-CIPRGD(Y-OMe)RC-NH$_2$ (SEQ ID NO.3) and Ac-CNPRGD(Y-OMe)RC-NH$_2$ (SEQ ID NO. 3)(no. 32). Symbols and standard abbreviations for amino acid are as recommended by the IUPAC-IUB Joint Commission on Biochemical Nomenclature (JCBN) (*Biochem. J.* (1984) 219:345 and *Europ. J. Biochem.* (1984) 138:9, each incorporated herein by reference. Additional abbreviations are as follows: AAA, amino acid analysis Boc, tert-butoxy-carbonyl; Cit, Citrulline; DCM, dichloromethane; ELISA, enzyme-linked immunosorbent assay; FABMS, fast atom bombardment mass spectrum; HOBT, N-Hydroxy-benzoltriazole; Hpa, homophenylalanine; Mpr, β-mercaptopropionic acid; 2-Nal, β-(2-naphthyl)-alanine; Pen, penicillamine; Pgl, phenylglycine; Pmc, β,β-pentamethylenecysteine; Pmp, β,β-pentamethylene-βmercaptopropionicacid; TLC, thin-layer chromatography; Tmc, β,β-tetramethylenecysteine; p-I-F, p-iodo-phenylalanine; p-Cl-F, p-chloro-phenylalanine; p-NO$_2$-F, p-nitro-phenylalanine, Y-OMe, 0-methyltyrosine; Y-O-n-butyl, O-n-butyl-tyrosine.

FIG. 22 (SEQ ID NOS. 3, 160–163, 2 and 164, respectively) is a Table showing the effect of modifying Ac-CNPRGD(Y—Me)RC-NH$_2$ at position −3 (as defined, infra). Symbols and standard abbreviations for amino acid are as recommended by the IUPAC-IUB Joint Commission on Biochemical Nomenclature (JCBN) (*Biochem. J.* (1984) 219:345 and *Europ. J. Biochem.* (1984) 138:9, each incorporated herein by reference. Additional abbreviations are as follows: AAA, amino acid analysis Boc, tert-butoxy-carbonyl; Cit, Citrulline; DCM, dichloromethane; ELISA, enzyme-linked immunosorbent assay; FABMS, fast atom bombardment mass spectrum; HOBT, N-Hydroxy-benzoltriazole; Hpa, homophenylalanine; Mpr, β-mercaptopropionic acid; 2-Nal, β-(2-naphthyl)-alanine; Pen, penicillamine; Pgl, phenylglycine; Pmc, β,β-pentamethylenecysteine; Pmp, β,β-pentamethylene-β-mercaptopropionicacid; TLC, thin-layer chromatography; Tmc, β,β-tetramethylenecysteine; p-I-F, p-iodo-phenylalanine; p-Cl-F, p-chloro-phenylalanine; p-NO$_2$-F, p-nitro-phenylalanine, Y-OMe, O-methyltyrosine; Y-O-n-butyl, O-n-butyl-tyrosine.

FIG. 23 (SEQ ID NOS. 3, 129, 125–128, 130 and 165 respectively) is a Table showing the effect of substitutions of Arginine at position 4 (as defined, infra) on Ac-CNPRGD (Y-OMe)RC-NH$_2$. Symbols and standard abbreviations for amino acids are as recommended by the IUPAC-IUB Joint Commission on Biochemical Nomenclature (JCBN) (*Biochem. J.* (1984) 219:345 and *Europ. J. Biochem.* (1984) 138:9, each incorporated herein by reference. Additional abbreviations are as follows: AAA, amino acid analysis Boc, tert-butoxy-carbonyl; Cit, Citrulline; DCM, dichloromethane; ELISA, enzyme-linked immunosorbent assay; FABMS, fast atom bombardment mass spectrum; HOBT, N-Hydroxy-benzoltriazole; Hpa, homophenylalanine; Mpr, β-mercaptopropionic acid; 2-Nal, β-(2-naphthyl)-alanine; Pen, penicillamine; Pgl, phenylglycine; Pmc, β,β- pentamethylenecysteine; Pmp, β,β-pentamethylene-β-mercaptopropionicacid; TLC, thin-layer chromatography; Tmc, β,β-tetramethylenecysteine; p-I-F, p-iodo-phenylalanine; p-Cl-F, p-chloro-phenylalanine; p-NO$_2$-F, p-nitro-phenylalanine, Y-OMe, O-methyltyrosine; Y-O-n-butyl, O-n-butyl-tyrosine.

FIG. 24 (SEQ ID NOS. 3, 125–126, 165 and 15, respectively) shows the peptide effect on template bleeding time.

DETAILED DESCRIPTION OF THE INVENTION

The invention provides cyclic peptides which inhibit platelet aggregation without causing prolonged bleeding time. In one embodiment, peptides are provided which are cyclic and contain the sequence:

$X_1X_2X_3X_4$G D $X_5X_6X_7X_8$(SEQ ID NO. 4)

wherein $X_1$ and $X_8$ are 0 to 20 amino acids;

$X_2$ and $X_7$ are 0 or an amino acid capable of forming a bridge;

$X_3$ is 0 to 10 amino acids;

$X_4$ is a positive amino acid;

$X_5$ is a hydrophobic amino acid; and $X_6$ is a positively charged amino acid.

These peptides are effective in inhibiting platelet aggregation and can therefore advantageously be used to dissolve blood clots as well as prevent inappropriate growth of vascular smooth muscle cells and arterial graft occlusion. Unexpectedly, such treatment does not cause the concomitant significant prolonged bleeding which has limited the usefulness of other anti-thrombotic agents. The use of such peptides is therefore a significant improvement over conventional therapy, including therapy utilizing other RGD-containing peptides.

As used herein, references to "Arg-Gly-Asp containing peptides" or "RGD peptides" are intended to refer to peptides having one or more Arg-Gly-Asp containing sequences which may function as binding sites for a receptor of the "Arg-Gly-Asp family of receptors", i.e., those recognizing and binding to the Arg-Gly-Asp sequence. It is understood that functional equivalents of Arg-Gly-Asp such as Lys-Gly-Asp (KGD) or chemical structures other than amino acids which functionally mimic the Arg-Gly-Asp tri-peptide sequence are also included within this definition. While the Arg-Gly-Asp sequence and its functional equivalents have been found necessary to retain the binding activity, the composition of the remaining peptide as well as any other chemical moiety present in conjunction with the peptide may vary without necessarily affecting the activity of the binding site. Where specific chemical structures or sequences beyond the Arg-Gly-Asp sequence are presented, it is intended that various modifications which do not destroy the function of the binding site are to be encompassed without departing from the definition of the peptide.

As used herein, the term "bridge" refers to a chemical bond between two amino acids, amino acid derivatives or other chemical moieties in a peptide other than the amide bond by which the backbone of the peptide is formed unless the amide bond cyclizes the peptide to form a lactam. Such lactam is included within the term "bridge."

As used herein, the term "peptide bond" or "peptide linkage" refers to an amide linkage between a carboxyl group of one amino acid and the α-amino group of another amino acid.

As used herein, the term "peptide" is intended to include molecules containing amino acids linearly coupled through peptide bonds. Such peptides may additionally contain amino acid derivatives or non-amino acid moieties. The amino acids can be in the L or D form so long as the binding function of the peptide is maintained. Such peptides can be of variable length, preferably between about 4 and 200 amino acids, more preferably between about 7 and 35 amino acids, and most preferably between about 6 to 9 amino acids. The term amino acid refers both to the naturally occurring amino acids and their derivatives, such as TyrMe and PheCl, as well as other moieties characterized by the presence of both an available carboxyl group and amine group. Non-amino acid moieties which can be contained in such peptides include, for example, amino acid mimicking structures. Mimicking structures are those structures which exhibit substantially the same spatial arrangement of functional groups as amino acids but do not necessarily have both the α-amino and α-carboxyl groups characteristic of amino acids.

As used herein, the term "cyclic peptide" refers to a peptide having an intramolecular bond between two non-adjacent amino acids within a peptide. The intramolecular bond includes, but is not limited to, backbone to backbone, side-chain to backbone and side-chain to side-chain bonds. Various amino acid derivatives and chemical moieties can participate in such bonds, including, for example, Pen, Pmp and Pmp analogues and Pmc and Pmc analogues. Pmc is also known as amino-Pmp (am-pmp).

As used herein, the terms "not prolonging bleeding time" or "not substantially prolonging bleeding time" or "without prolonging bleeding time" (or their grammatical equivalents) refer to maintaining a bleeding time which is substantially the same as that obtained from an untreated animal. Thus peptides which do not prolong bleeding time are those which when administered to an animal do not extend the bleeding time by more than about a factor of two or three as measured by assays such as that provided in Example VII 6., infra.

The one-letter and three-letter abbreviations for amino acids and other moieties used herein are given as follows:

| | | |
|---|---|---|
| A | Ala | Alanine |
| | α-ABA | α-Amino isobutyric acid |
| R | Arg | Arginine |
| N | Asn | Asparagine |
| D | Asp | Aspartic acid |
| | Cha | Cyclohexyl-alanine |
| | Cit | Citrulline |
| C | Cys | Cysteine |
| Q | Gln | Glutamine |
| E | Glu | Glutamic acid |
| G | Gly | Glycine |
| H | His | Histidine |
| | Hpa | Homophenylalanine |
| I | Ile | Isoleucine |
| L | Leu | Leucine |
| K | Lys | Lysine |
| M | Met | Methionine |
| | Mpr | β-Mercaptopropionic acid |
| | 2-Nal | 3-(2-naphthyl)alanine |
| | N—Me—R | N-methyl-arginine |
| | O—Me—Y | O-methyl-tyrosine |
| | O—Et-Tyr | O-ethyl-tyrosine (Y—OEt) |
| | O-n-butyl-Tyr | O-n-butyl-tyrosine (Y—O-n-butyl) |
| | O-n-hexyl-Tyr | O-n-hexyl-tyrosine |
| | Orn | Ornithine |
| | p-amino-Phe | para-amino-phenylalanine |

-continued

| | Pas | 6,6-Cyclopentamethylene-2-Aminosuberic acid analogues |
| --- | --- | --- |
| | Pen | Penicillamine |
| F | Phe | Phenylalanine |
| | PheCl | para-chloro-phenylalanine (P—Cl—F) |
| | Phg | Phenylglycine |
| | p-iodo-Phe | para-iodo-phenylalanine |
| | Pmc | β,β-pentamethylenecysteine |
| | Pmp | β,β-pentamethylene-β-mercaptopropionic acid |
| | p-nitro-Phe | para-nitro-phenylalanine (p-NO$_2$—F) |
| P | Pro | Proline |
| S | Ser | Serine |
| | SuccAla | Succinyl-alanine |
| T | Thr | Theonine |
| | Tmc | β,β-tetra-methylenecysteine |
| W | Trp | Tryptophan |
| Y | Tyr | Tyrosine |
| | TyrMe | O-methyl-Tyrosine |
| V | Val | Valine |
| | 2-Nal | (2-naphthyl) alanine |
| | 3,5-diiodo-Tyr | 3,5-diiodo-tyrosine |

As used herein, the term "hydrophobic" is intended to include those amino acids, amino acid derivatives, amino acid mimics and chemical moieties which are non-polar. Hydrophobic amino acids include Phe, Val, Trp, Ile and Leu. Other hydrophobic amino acids useful in the invention are TyrMe, PheCl and Cha, O-Et-Tyr, O-n-hexyl-Tyr, 3,5-diiodo-Tyr, Hpa, 2-Nal, O-n-butyl-Tyr, p-nitro-Phe, Phg, p-iodo-Phe, p-amino-Phe and Cit.

As used herein, the term "positively charged amino acid" refers to those amino acids, amino acid derivatives, amino acid mimics and chemical moieties which are positively charged. Positively charged amino acids include, for example, Lys, Arg and His and Orn homo-Arg. Such positively charged amino acids are preferably found in positions designated $X_4$ or $X_7$ or designated "+4 position" in the examples that follow.

Although the invention will be described with reference to RGD receptor binding peptides, it is understood that functional equivalents known to those skilled in the art can be substituted for the RGD sequence without departing from the spirit of the invention. One skilled in the art will be able to use such functional equivalents to practice the invention described herein.

It is now well-established that the amino acid sequence RGD is the cell binding site in a number of proteins, including for example, fibronectin, vitronectin and type IV collagen. The RGD binding site is recognized by a family of cell surface receptors, termed integrins. Platelets contain a large repertoire of RGD-cell surface receptors, each of which recognizes one or more RGD containing ligands to perform various physiological functions. GP IIb/IIIa is one such integrin receptor found in platelets. The ligands recognized by this receptor include fibrinogen and other serum proteins. GP IIb/IIIa is primarily responsible, through interaction with other platelets to form aggregates and through interactions with the endothelial surface of injured blood vessels, for the development of coronary artery thrombosis. When provided in soluble form, RGD peptides can inhibit cell attachment or platelet aggregation through competition with other RGD containing ligands. See for example U.S. Pat. Nos. 4,578,079, 4,517,686, 4,792,525, 4,683,291, and 5,041,380, which are incorporated herein by reference.

Because prolongation of bleeding time can be an undesirable side effect of thrombolytic therapy the present peptides which do not have this side effect are extremely useful. The effect of a peptide on bleeding time can be easily determined by one skilled in the art using for example, a protocol as described in Example VII., 6. Hemodynamic Responses.

Unexpectedly, the presence of a positively-charged amino acid in the "+4 position" of the RGD binding site, i.e., the position adjacent to the residue in the X position of the sequence RGDX, confers the characteristic of not prolonging bleeding time to platelet aggregation inhibiting peptides. The position assignments are as follows:

| $X_1$ | $X_2$ | $X_3$ | $X_4$ | G | D | $X_5$ | $X_6$ | $X_7$ | $X_8$ |
| --- | --- | --- | --- | --- | --- | --- | --- | --- | --- |
| −3 | −2 | −1 | 0 | +1 | +2 | +3 | +4 | +5 | +6 |

Illustrative of such a peptide is Ac-CNPRGD(O-Me-Y)RCNH$_2$ ("8×"). Such a positive charge can, for example, result from the presence of a positively charged amino acid, such as Arg, Lys, homo-Arg or ornithine, in the +4 position. Alternatively, an amino acid derivative or amino acid mimic having a positive charge in the +4 position can produce the desired effect. In addition, a positively charged chemical amino acid which is spatially arrayed so as to occupy substantially such a position can also confer the characteristic. Such an amino acid need not be linearly arrayed in the +4 position so long as its positive charge occupies substantially the same spatial site as that occupied by the guanidino functional group in the +4 arginine of 8×, supra.

The peptides of the present invention can be synthesized by any of the suitable methods well known in the art including methods of chemical synthesis. Preferably, the linear sequence is synthesized using commercially available automated peptide synthesizers such as those manufactured by Applied Biosystems, Inc., Foster City, Calif. The material so synthesized can be precipitated and further purified, for example by high performance liquid chromatography (HPLC). Although a purity of greater than 95 percent for the synthesized peptide is preferred, lower purity may be acceptable.

To obtain one of the enhanced peptides of the present invention which has a high potency for inhibiting platelet aggregation and which does not cause prolonged bleeding when administered to an animal, the synthesized peptide is cyclized using methods well known in the art. Where the peptides contain two sulphur-containing amino acids or other moieties, cyclization can be achieved through a disulfide bond. Examples of useful sulphur-containing moieties are Cys, Pen, Pmp, and Pmc. Alternatively, cyclization can be accomplished through the formation of an amide (peptide) bond or alkyl bridge structure (for example, a dicarba bridge), using, for example, Pas. Where the residues contain sulfhydryls, a disulfide bridge can be formed by oxidizing a dilute aqueous solution of the peptides with K$_3$[F$_e$(CN)$_6$] or by air oxidation. Other residues, such as the chemical moieties Pmp and Pmc, can create a bridging structure through a disulfide bond between Pmp (or Pmc) and Cys (or similar structures). A dicarba bridge, in which the disulfide bridge is replaced with two methylene groups, can be formed using Pas. Other means of cyclizing, which are known in the art, can also be utilized.

The cyclized peptides of the present invention can also be prepared by forming an amide peptide bond (lactam) between non-adjacent amino acid residues. A procedure for forming such an amide bond is provided in Schiller et al., Int. J. Peptide Protein Res. 25:171 (1985), which is incorporated herein by reference. Briefly, side-chain to side-chain cyclizations can be performed by the above procedure using $N^a$-Boc-amino acids together with OFm/Fmoc side-chain protection for Asp and Lys residues as described by Felix et al., Int. J. Peptide Protein Res. 31:231 (1988), which is incorporated herein by reference. Alternatively, side-chain to backbone cyclizations can be performed using this procedure.

Peptides included in the present invention can contain a hydrophobic amino acid adjacent the carboxy terminus of the RGD sequence. The hydrophobic amino acids can have a range of structural types and hydrophobicities. Appropriate hydrophobic amino acids include for example Phe, Trp, Val, Ile, Leu, PheCl, TyrMe, and Cha, O-n-hexyl-Tyr, 3,5-diiodo-Tyr, Hpa, 2-Nal, O-n-butyl-Tyr and the like. Such peptides can be represented as $X_1X_2X_3X_4GDX_5X_6X_7X_8$ wherein $X_5$ is a hydrophobic amino acid. $X_2$ and $X_7$ are amino acids capable of forming a bridge, such as a disulfide bridge, alkyl bridge or a peptide bond. Representative of these amino acids are Cys, Pen, Pmp, Pmc and Pas. $X_6$ is a positively charged amino acid. $X_1$ and $X_8$ are 0 to 20 amino acids. When the number of residues of $X_1$ is one, $X_1$ is preferably a Gly; when the number of residues is greater than one, the carboxy terminal residue is preferably a Gly. $X_3$ is 0 to 10 amino acids, preferably with His or Pro as the carboxy terminal residue. $X_4$ is a positively charged amino acid, such as Arg or Lys. Specific peptides of this nature include GPenGHRGDLRCA (SEQ ID NO. 5), RPenGHRGD-WRCR (SEQ ID NO. 6), RPenGHRGD(Cha)RCR (SEQ ID NO. 7), PmpGHRGDLRCA (SEQ ID NO. 8), G(dPen) GHRGDLRCA (SEQ ID NO. 9), R(am-Pmp) GHRGDWRCR (SEQ ID NO. 10), R(am-Pmp)GHRGD (TyrMe)RCR (SEQ ID NO. 11), R(am-Pmp)GHRGD (PheCl)RCR (SEQ ID NO. 12), R(am-Pmp)GHRGDLRCR (SEQ ID NO. 13), R(am-Pmp)GHRGDLRCR, R(t-but-am-Pmp)GHRGDLRCR (SEQ ID NO. 14), Ac-CNPRGD(O-Me-Y)RCNH$_2$, Ac-CNPKGD(Y-OMe)RC-NH$_2$(SEQ ID NO. 15), Ac-CNPRGD(O-N-Butyl-Y)RC-NH$_2$(SEQ ID NO. 16).

Peptides having sequences other than those specifically identified herein are also included in the invention provided they exhibit the requisite functional criteria. Peptides which have high anti-thrombotic activity and which do not prolong bleeding time can be synthesized and tested using the teachings described herein. Such peptides once synthesized can be tested for anti-thrombotic activity using, for example, the platelet aggregation assays described in Example V.

Peptides of the present invention that reduce platelet aggregation without prolonging bleeding time have a characteristic ratio of $IC_{50}$ values determined in the platelet aggregation assay conducted both in low calcium and high calcium. An $IC_{50}$ (high calcium): $IC_{50}$ (low calcium) ratio of at least about 5–20 is indicative of a peptide having both desired characteristics. An example of low calcium conditions is an assay conducted in citrate which provides a calcium concentration of ~40 $\mu$M. An example of high calcium conditions is an assay conducted in heparin, which provides a physiological calcium concentration of ~1.2–1.6 mM. The platelet aggregation assay can be conducted using whole blood or platelets.

The relative affinity of the peptide for the various integrin receptors can be tested using, for example, the liposome binding assay of Example IV or the ELISA assays of Examples III and XI. Peptides exhibiting high potency for inhibiting platelet aggregation and also showing high affinity for GP IIb/IIIa and low affinity for the fibronectin and vitronectin receptors should be selected to determine their effect on bleeding time. Animal models such as the baboon models or rabbit models described in Examples VIII and IX can be used to assess bleeding time. After the peptides are administered, the effect can be monitored by cutting the animal and allowing it to bleed onto an absorbent towel or tissue. The length of time until the bleeding stops should be compared to the animal's bleeding time without peptide administration. Peptides which fall within the teachings described herein will not increase the bleeding greater than about two to three-fold over that of an untreated control. Thus, one skilled in the art can use the teachings of the invention to make and test a variety of peptides having the generic structures described herein.

In another aspect of the invention, peptides are provided that possess relatively high affinity for the receptor IIb/IIIa and low affinity for the fibronectin and vitronectin receptors. Such IIb/IIIa affinity can be determined, as for example, by a liposome attachment assay, as described in Examples IV and VI or in a platelet aggregation assay as described in Examples V and XI. Peptides characterized by high affinity for IIb/IIIa will have an $IC_{50}$ as measured under the assay conditions provided in Examples IV and VI of less than about 10 $\mu$M, preferably less than about 1 $\mu$M, more preferably about 0.1 $\mu$M. Alternatively, affinity for IIb/IIIa as characterized in Example V will have an $IC_{50}$ of less than about 10 $\mu$M, preferably less than about 1 $\mu$M, more preferably about 0.1 $\mu$m. Fibronectin receptor affinity and vitronectin receptor affinity can be determined, for example, by the methods detailed in Examples III and VI, and IV and VI respectively, and Example IX. Using these assays, under the conditions described, peptides having low affinity for the fibronectin receptor will have an $IC_{50}$ of greater than about 0.1 $\mu$M, preferably greater than about 1 $\mu$M, more preferably greater than about 10 $\mu$M; low affinity for the vitronectin receptor is greater than about 1 $\mu$M, preferably greater than about 10 $\mu$M, more preferably greater than about 100 $\mu$M. It is thus possible to screen various peptides in order to determine their inhibitory concentrations, and therefore binding affinities, and to select those having high affinity for the IIb/IIIa and low affinity for the fibronectin and vitronectin receptors.

The invention also provides peptides which differentially inhibit the binding of various ligands to GP IIb/IIIa, and do not result in a prolongation of bleeding time. For example, the peptide designated herein as 8x inhibits the binding of fibrinogen to GP IIb/IIIa more than it inhibits the binding of fibronectin and vitronectin to the same integrin.

The peptides of the present invention can be utilized to effectively eliminate thrombotic conditions by administering to a mammal exhibiting thrombosis a therapeutically effective amount of the peptide in a suitable physiologically acceptable carrier. Effective amounts will be 1 to 50 mg/kg/hr body weight, preferably about 1 to 5 mg/kg body weight. Appropriate effective amounts can be easily determined by those skilled in the art. The peptide can be administered in a variety of ways, as for example, by infusion or injection. Length of treatment can be determined by monitoring effect.

The claimed subject matter further includes a series of cyclic disulfide and lactam peptides which are highly potent and selective GP IIb/IIIa antagonists. These disulfide or lactam-containing peptides are more conformationally restricted than their linear counterparts due to their cyclic nature; reduction of the ring size constrains the structure further.

A series of small cyclic disulfide heptapeptides containing the sequence $X_4GDX_5X_6$ (SEQ ID NO. 166) ($X_4$ is a positively charged amino acid, $X_5$ is a hydrophobic amino acid and $X_6$ is a positively charged amino acid), and fewer amino acids than in the previously described peptides, were synthesized. The above-noted pharmacophore sequence is responsible for the peptides' high GPIIb/IIIa binding affinities, high selectivities, and their distinct biological properties. The remaining amino acids in the ring serve primarily a structural role to favor the bioactive conformations in which the critical residues are spatially situated for optimal interaction with the receptor. For example, peptide 16A (Mpr)RGD(O-Me-Y)RC-NH$_2$ (SEQ ID NO. 17) inhibited platelet aggregation with an IC$_{50}$ of 0.12 μM, which indicates about two-fold more reactivity than 8× (Ac-CNPRGD(O-Me-Y)RC-NH$_2$). The asparagine and proline residues were deleted from 8× without loss of activity and selectivity. Peptide 16A and the other smaller ring analogues are more compact than the previously mentioned peptides and are thus more conformationally rigid. Examples of the smaller ring analogue peptides include the following:

13Q AcCRGD(O-Me-Y)RC-OH (SEQ ID NO. 18)
14T AcCRGD(O-Me-Y)R(Pen)-NH$_2$ (SEQ ID NO. 19)
14U Ac(dPen)RGD(O-Me-Y)RC-NH$_2$ (SEQ ID NO. 20)
14V Ac-CKGD(O-Me-Y)RC-NH$_2$ (SEQ ID NO. 21)
14Z Ac-CRGD(O-Me-Y)R(dPen)-NH$_2$ (SEQ ID NO. 22)
15V Ac-CRGD(O-Me-Y)RC-NH$_2$ (SEQ ID NO. 23)
15W Ac-CRGD(O-Me-Y)RC-R-NH$_2$ (SEQ ID NO. 24)
16A (Mpr)RGD(O-Me-Y)RC-NH$_2$
17Z (Mpr)RGD(O-n-butyl-Y)RC-NH$_2$ (SEQ ID NO. 25)
17Y (Mpr)KGD(O-Me-Y)RC-NH$_2$ (SEQ ID NO. 26)
17O (Pmp)RGD(O-Me-Y)RC-NH$_2$ (SEQ ID NO. 27)
17Q Ac-CRGD(O-n-butyl-Y)RC-NH$_2$ (SEQ ID NO. 28)
17V Ac-CRGD(Hpa)RC-NH$_2$ (SEQ ID NO. 29)
13G Ac(dPen)HRGD(O-Me-Y)RC-NH$_2$ (SEQ ID NO. 30)

Such peptides can be represented as $X_1X_2X_3X_4GDX_5X_6X_7X_8$ wherein $X_4$ is a positively charged amino acid, preferably Arg, Lys, or homoArg or mimics thereof; $X_5$ is a hydrophobic amino acid; $X_6$ is a positively charged amino acid; $X_3$ is 0 to 10 amino acids, preferably 0–2; $X_1$ and $X_8$ are 0 to 20 amino acids; and $X_2$ and $X_7$ are 0 or an amino acid capable of forming a bridge, such as a disulfide bridge or a dicarba bridge, in which the disulfide bridge is replaced with two methylene groups, or a lactam (amide) bond. Representative of these amino acids are Cys, Pen, Pmp, Pmc, Mpr and Pas.

In order to further enhance the chemical and metabolic stability of these smaller cyclic disulfide peptides, corresponding lactam analogues were designed and synthesized. Cyclic lactams which use the side chain groups on amino acid residues to form covalent attachments to other side chain groups on the peptide are known (Felix, et al., *Int. J. Peptide Protein Res.* 31:231 (1988); Felix et al., *Int. J. Peptide Protein Res.* 32:441 (1988); AL-Obeidi et al., *J. Med. Chem.* 32:2555 (1989)) each of which is incorporated herein by reference. Within the present framework, cyclic lactam peptides were synthesized utilizing the acid side-chain groups of Asp or Glu to form covalent attachments (lactam bridges) to the N-terminal (—NH$_2$ of β-Ala, Gly, or Arg). Examples of the lactam bridged analogues include the following:

23E GNPRGD(O-n-butyl-Y)RE-NH$_2$ (SEQ ID NO. 31)
21I RGD(O-Me-Y)RE-NH$_2$ (SEQ ID NO. 32)
17I GRGD(O-Me-Y)RE-NH$_2$ (SEQ ID NO. 33)
17J GNPRGD(O-Me-Y)RE-NH$_2$ (SEQ ID NO. 34)
20Q GNPRGD(O-Me-Y)RD-NH$_2$ (SEQ ID NO. 35)
18G (β-Ala)RGD(O-Me-Y)RD-NH$_2$ (SEQ ID NO. 36)
18J (β-Ala)NPRGD(O-Me-Y)RD-NH$_2$ (SEQ ID NO. 37)
20M GRGD(O-n-butyl-Y)RE-NH$_2$ (SEQ ID NO. 38)

Such peptides can be represented as $X_1X_2X_3X_4GDX_5X_6X_7X_8$ wherein $X_4$ is a positively charged amino acid, preferably Arg, Lys, or homoArg or mimics thereof; $X_5$ is a hydrophobic amino acid; $X_6$ is a positively charged amino acid; $X_3$ is 0 to 10 amino acids, preferably 0 to 2; $X_1$ and $X_8$ are 0 to 20 amino acids; $X_2$ is 0 to 1 amino acid, preferably Gly, Arg or β-alanine when $X_2$ is 1; and $X_7$ is an amino acid capable of forming a lactam bridge, such as aspartic acid, glutamic acid or higher homologue of glutamic acid, lysine, ornithine or α, β-diaminopropionic acid, and where $X_1$, $X_2$ and $V_3$ are 0, the lactam bridge is formed through the side chain of $X_4$, as in 21I. These peptides are characterized as having intramolecular lactam bridges. These cyclic lactam peptides were synthesized utilizing the acid side-chain groups, of Asp or Glu for example, to form covalent attachments (lactam bridges) to the N-terminal amines (—NH$_2$ of β-Ala, Gly or Arg, for example).

Ring-size has an effect on the potencies of cyclic lactam analogues. The 23-membered cyclic lactam analogue 17I GRGD(O-Me-Y)RE-NH$_2$, and the 20-membered cyclic lactam analogue 21I RGD(O-Me-Y)RE-NH$_2$ were prepared and evaluated. Members of the ring refers to the number of bonds in the primary ring structure. These novel cyclic lactam peptides were synthesized using the acid side-chain group of Glu to form covalent attachment (lactam bridge) to the N-terminal amine (—NH$_2$ of Gly or Arg). The formation of the cyclic lactam bridge was accomplished on the solid-phase support as outlined in FIG. 13 for 18G and all the cyclic lactam peptides. Testing indicated that the smaller analogue, 21I having six residues, or 20 members, possessed one of the highest potencies among the cyclic RGD peptides synthesized; it inhibited platelet aggregation with an IC$_{50}$ of 0.08 μM, which is about three-fold more reactive than 8× Ac-CNPRGD(O-Me-Y)RC-NH$_2$, which has nine amino acid residues, or 29 members. Similarly, the 28-membered cyclic lactam analogue 20Q is about three times more potent than the 29-membered cyclic lactam analogue 17J, and about 20 times more potent than the 29-membered cyclic lactam analogue 18J.

The following illustrate the structural characterisics of some of the claimed RGD cyclic analogues:

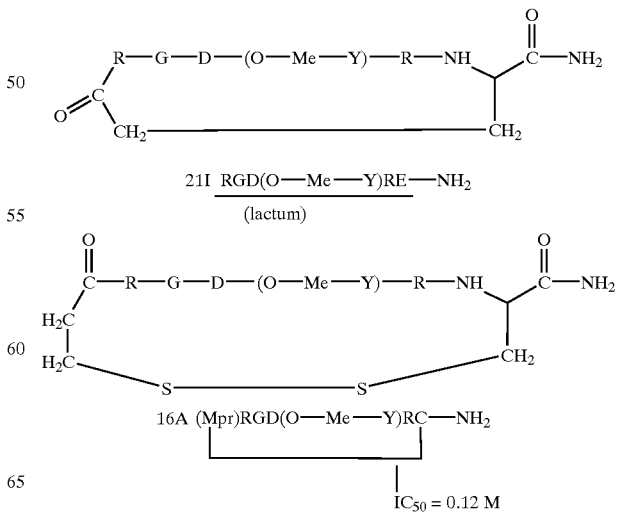

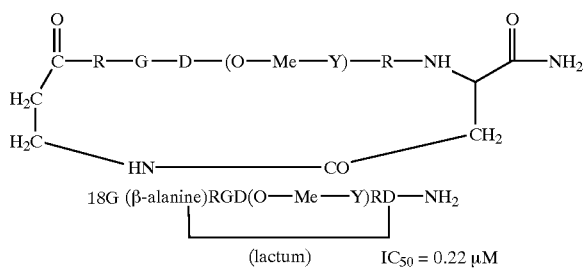

18G (β-alanine)RGD(O—Me—Y)RD—NH₂
(lactum)    IC₅₀ = 0.22 μM

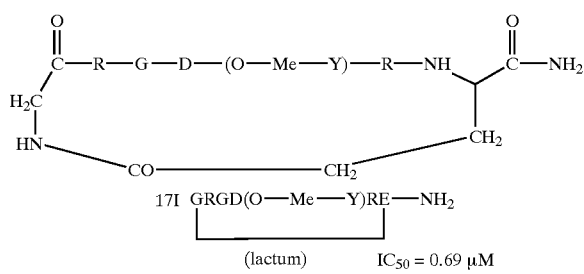

17I GRGD(O—Me—Y)RE—NH₂
(lactum)    IC₅₀ = 0.69 μM

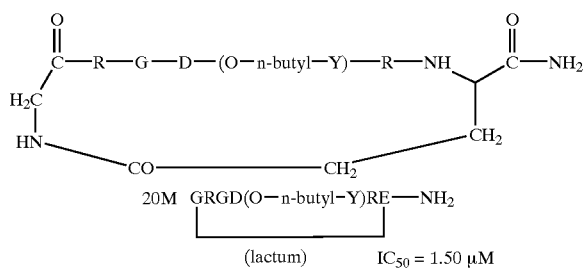

20M GRGD(O—n-butyl-Y)RE—NH₂
(lactum)    IC₅₀ = 1.50 μM

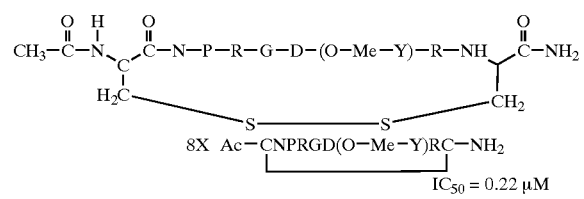

8X Ac—CNPRGD(O—Me—Y)RC—NH₂
IC₅₀ = 0.22 μM

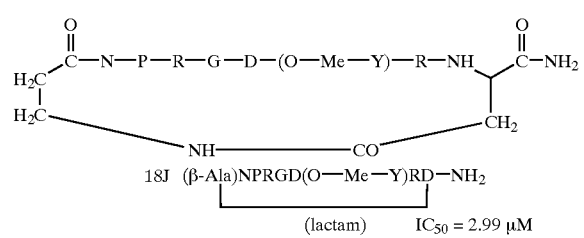

18J (β-Ala)NPRGD(O—Me—Y)RD—NH₂
(lactum)    IC₅₀ = 2.99 μM

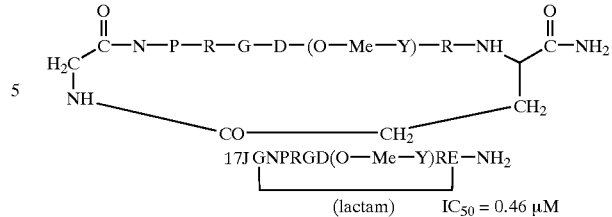

17J GNPRGD(O—Me—Y)RE—NH₂
(lactam)    IC₅₀ = 0.46 μM

20Q GNPRGD(O—Me—Y)RD—NH₂
(lactam)    IC₅₀ = 0.16 μM

The claimed subject matter further include cyclic RGD-containing peptides which bear an exocyclic positive charge:

14S Ac-CRGD(O-Me-Y)P(Pen)-R-NH₂ (SEQ ID NO. 39)

22I Ac-C(N-Me-R)GD(Pen)-R-NH2 (SEQ ID NO. 40)

These peptides can be described using the terms of the previous formulas as $X_1X_2X_3X_4GDX_5X_7X_6$, where $X_5$ may be 0.

The present invention also contemplates a linear peptide having the formula:

18F Ac-RGD(O-n-butyl-Y)-R-NH₂ (SEQ ID NO. 41)

The following Examples are intended to illustrate but not limit the invention.

EXAMPLE I

Peptide Synthesis

Peptides of the present inventiion were synthesized according to the procedure in this Example or in Example XI. Peptides were synthesized on an automated peptide synthesizer (Model 430A, Applied Biosystems, Foster City, Calif. USA) using optimized n-methyl pyrrolidone chemistry on PAM resin as recommended by the manufacturer. Cleavage of the peptides from the resin was achieved with 100% hydrogen fluoride. The peptides were further purified by HPLC using a VYDAC reverse phase $C_{18}$ column with 0 to 60% acetonitrile gradients. Peptides were used only if found to be ≧98% pure.

For Pen cyclization, 611 mg of the peptide synthesized as described above were dissolved in 4 liters of water that had been previously boiled and allowed to cool. Immediately prior to addition of the peptide, nitrogen was bubbled through the water for 45 minutes. After the peptide was dissolved, a solution of 0.1 μg/ml of potassium ferrous cyanide $K_3[Fe(CN)_6]$ in water was added dropwise to the stirred peptide solution until the yellow color persisted for 5 minutes (approximately 5 ml). The pH of the solution was held at 7.0 throughout this procedure by addition of $NH_4OH$. The solution was allowed to stand for 20 hours under low vacuum and then lyophilized. Excess $K_3[Fe(CN)_6]$ was removed by passing the cyclized material over a Sephadex G-15 column (1.8×120 cm). The peptide was purified by reverse phase HPLC using a Waters Bondapak™ $C_{18}$ column (3×30 cm; 10 μm packing) (Waters Assoc., Milford, Mass.). The peptide was loaded on the column in buffer A (20 mM ammonium acetate at pH 7.5) and eluted with a gradient of buffer B consisting of 60% acetonitrile and 40% buffer A. Eluted fractions were tested for their ability to inhibit receptor binding.

The major peak obtained from the $C_{18}$ column constituted 90% of recovered peptide and was deduced to be a monomeric cyclic peptide because it was retained on the column for the length of time predicted for that sequence and because the uncyclized material and multimeric forms were well separated from the main peak.

EXAMPLE II

Receptor and Ligand Purifications

Receptor and ligand purifications were performed according to the methods in this Example or those in Example XI.C. Receptors were purified according to the procedures of Pytela et al. (Methods Enzymol. 144:475 (1987)), incorporated herein by reference. Briefly, vitronectin receptor (Vn-R) was purified by RGD peptide-affinity chromatography from (100 mM) octyl glucoside (OG) extracted human placenta. After extraction, the suspension was filtered over a Sepharose 6B column and then applied to a GRGDSPK column. Except where stated, all procedures were carried out at 4° C. The peptide column was washed with three volumes of Tris-buffered saline (TBS) containing 1 mM $Ca^{2+}$ and 25 mM OG and then with TBS containing 1 mM $Ca^{2+}$ and 25 mM octyl thioglucoside (OTG) at room temperature. Elution of bound receptor was achieved at room temperature with TBS containing 20 MM EDTA and 25 mM OTG. Finally, $Ca^{2+}$ and $Mg^{+2}$ were added to eluted fractions to achieve final concentrations of 1 mM for both ions.

Fibronectin receptor (Fn-R) was similarly purified from (100 mM) octyl glucoside-extracted human placenta using a procedure identical to that for the Vn-R up to and including the initial Sepharose chromatography step. The Sepharose 6B column flow-through was brought to 2 nM $Mn^{+2}$ and the resulting solution was run over a 110 kd fibronectin fragment-affinity column. Washing and elution steps were identical to those used in purifying vitronectin receptor.

Platelet glycoprotein IIb/IIIa was purified from outdated human platelets. Briefly, the platelets were washed 3 times with 10 mM tris-HCl, 150 mM NaCl (TBS), 1 mM EDTA, pH 7.5, and centrifuged at 2000×g to pellet cells. Cells are lysed in 5 pellet volumes of TBS, 1% Triton X-100, 1 mM $Ca2Cl_2$, and followed by centrifugation at 30,000×g. The supernatant fraction is collected and the supernatant is loaded onto a concanavalin-A column, previously equilibrated in TBS, 1 mM $Ca2Cl_2$, 0.1% Triton, 0.05% $NaN_3$ and eluted with 0.2 M α-methylmannoside. Fractions were pooled and loaded onto a heparin-agarose column. The flowthrough is collected and concentrated on an Amicon YM 30 filter to a volume of approximately 5–10 ml. The concentrate is then applied to an S-300 column (500 ml) and 6 ml fractions are collected. The $GPII_bIII_a$ containing fractions are collected, pooled and stored at −80° C.

The purification of fibrinogen is conducted essentially as described by Lipinska et al., (J. Lab. Clin. Med. 507 (1974)). Briefly, a 0.3% w/v/ solution of human fibrinogen (Kabi #5302) is dissolved in 150 mM NaCl. Saturated $(NH_4)_2SO_4$ is added dropwise with stirring to the fibrinogen solution to obtain about 16% saturation. The precipitate is spun down in appropriate size bottles at 2000×g. The supernatant is decanted and the precipitate resuspended in 150 mM NaCl (approximately 50% of the original volume). $NH_4SO_4$ is again added dropwise to obtain 16% saturation. The suspension is spun down and the precipitate is resuspended in Tris-saline in a minimal volume (approximately 5% of the original volume). Any remaining insoluble material is spun down at 2000 rpm in a Sorval type centrifuge and the fibrinogen supernatant is decanted and dialyzed overnight at 4° C. against Tris-saline. Characterization of the fibrinogen is by the Bradford protein assay, SDS-PAGE, and/or Western blotting using well known standard procedures.

EXAMPLE III

Enzyme-Linked Immunosorbent Assays (ELISA)

The ELISA assays were performed according to the methods of this Example or those of Example XI.D–F.

1. Human Vitronectin-Vitronectin Receptor ($α_vβ_3$) ELISA Assay

Human vitronectin (Vn) is isolated from human plasma and purified by affinity chromatography by the method of Yatohgo et al., (Cell Structure and Function 13:281–292 (1988)).

The purity of each receptor was assessed with SDS-PAGE under reducing and non-reducing conditions. Each receptor was flash-frozen in liquid nitrogen and stored frozen until use.

2. Fibronectin Receptor (Fn-R) ELISA Assay

Peptide binding to purified Fn-R was determined by using a competitive enzyme-linked immunosorbent assay (ELISA) in which fibronectin is immobilized and the binding of solubilized Fn-R and the binding of solubilized FN-R, in the presence of various concentrations of peptide analogue, is detected with a polyclonal anti-Fn-R antibody followed by a labelled anti-rabbit IgG conjugate.

Microtiter plates were coated with 110 μl of human fibronectin (at 2 μg/ml) in TBS. The plates were washed three times with TBS that contained 0.05% Tween 20. 50 microliters of receptor in TBS containing 20 mM octylglucoside and 2 mM $NmCl_2$ was added to each well. 50 microliters of peptide in the same buffer was then added in 10-fold serial dilutions. The plates were incubated for three hours at room temperature, washed with 200 μl of the above TBS-Tween buffer. 100 μl of affinity-purified rabbit anti-human fibronectin receptor antibody was added to the wells and the plates were incubated for an additional two hours, washed twice with TBS-Tween and then distilled water. Affinity-purified goat anti-rabbit IgG conjugated to horseradish peroxidase (100 μl) was then added to each well. Bonding reactions were incubated for 16 hours at room temperature. The following day, the plates were washed twice with TBS-Tween and then distilled water. 100 μl of substrate mixture (10 mg O-phenylenediamine in 25 ml 0.1 M citrate-phosphate buffer, pH 5.0, plus six microliters of 30% $H_2O_2$) was added to the plates and allowed to develop. The development process was stopped by adding 50 μl of 4N $H_2SO_4$ to each well.

3. Fibrinogen-GPIIbIIIa Receptor ELISA (Fg/IIbIIIa)

Microtiter plates, 96 wells were coated (Type Nunc 1 Maxispor™) with 10 μg/ml purified fibrinogen (100 μl/well), and allowed to stand overnight at 4° C. The plates were washed three times with PBS Tween, 0.137 M NaCl, 0.003 M KCl, 0.008 M $Na_2HPO_4$, pH 7.4 at room temperature, 0.05% Tween-20 and blocked for 1 to 2 hours at room temperature with 200 μl/well TNCNT (which is 0.5% BSA, 20 mM Tris, pH 7.5 at room temperature, 120 mM NaCl, 0.2% $NaN_3$, 2 mM $CaCl_2$, 0.05% Tween 20, [Calbiochem RIA grade or better]) on a plate shaker. The plates were again washed three times with PBS/Tween and 50 μl of sample in TNCNT is added. The mixture was incubated for 15 minutes at room temperature on a plate shaker. The stock solution of purified $GPII_bIII_a$ receptor from human platelets, (0.4–1.0 mg/ml $GPII_bIII_a$ in 0.1% Triton X-100, 1 mM $CaCl_2$, 20 mM Tris, 150 mM NaCl, 0.05% $NaN_3$ in 0.3 M N-acetyl glucosamine pH 7.5, stored at −70° C.), was reconstituted in TNCNT. Fifty (50) μl of this diluted $GPII_bIII_a$ was then added to each well and incubated on a plate shaker at room temperature. After one hour, the plates were washed four times with PBS/Tween and 100 μl of a polyclonal or monoclonal antibody specific for $GPIII_a$ such as AP3 (1 μg/ml) (See e.g. Newman et al., Blood, 65:227–232 (1985), incorporated herein by reference) and ELISA buffer (PBS, 0.5 BSA, 0.05% Tween 20, 0.01% Thimerasol) was added. After one hour incubation at room temperature on a plate shaker, the samples were washed 4 times with PBS/Tween. One hundred (100) μl of GAMHRP (horse radish peroxidase conjugate of goat anti-mouse IgG (Pel-Freeze Cat. 715305-1) dissolved in ELISA buffer) previously diluted to 1:10,000 was then added and incubated 1 hour at room temperature on a plate shaker. Samples were then washed 4 times with PBS/Tween and 100 ml $OPD/H_2O_2$ substrate was added ($OPD/H_2O_2$ substrate: dissolve 10 mg o-phenylenediamine in 15 ml phosphate/citrate buffer, kept at room temperature, in a 50 ml Falcon™ tube covered with foil; just before use, 6.25 μl of 30% $H_2O_2$ is added to give a final solution of 0.67 mg OPD/ml in 0.0125% $H_2O_2$). (The phosphate/citrate buffer consists of 16 mM Citric Acid, 50 mM $Na_2HPO_4$, pH 5.0). The color developed within 3 to 20 minutes and the reaction was stopped with 100 μl 1 M $H_2SO_4$. The optical density at 492 nm vs 405 nm was recorded and $IC_{50}$ values are determined.

4. Vitronectin-Vitronectin Receptor ELISA (Vn/VnR)

Anti-$GPII_bIII_a$ monoclonal antibodies specific for human $GPIII_a$ was prepared by the method of Newman et al. (Blood, 65:227–232 (1985), incorporated herein by reference), or a similar procedure. This mouse Mab is specific for the $β_3$ subunit of the vitronectin receptor. Rabbit Fab 2 anti-mouse Fc fragment horse radish peroxidase conjugate (anti-MuFc HRP) was obtained from PelFreeze (Cat. No. 715305-1).

Maxisorp microtiter plates were coated with 2 μg/ml human vitronectin dissolved in PBS (50 ml/well) and stored overnight at 4° C. The plates were washed two times with PBS-0.05% Tween-20 (wash buffer) and blocked by incubating with about 150 μl/well of assay buffer (1%, BSA (RIA grade or better) in 50 mM Tris-HCl, 100 mM NaCl, 1 mM $MgCl_2$, $CaCl_2$, $MnCl_2$ pH 7.4) for 60 minutes. Dilutions of standards were prepared and putative inhibitors (Table 2) were dissolved in assay buffer. The blocked plates were emptied and 20 μl well of inhibitor or standard solution was added to each well. Twenty-five (25) μl of a 30 μg/ml solution of purified $α_vβ_3$ in assay buffer was pipetted into the coated plate. The final concentration of receptor in the assay well was about 15 μg/ml. The plate was incubated on a shaker for 60 minutes. Meanwhile, for each microtite plate, 6 ml buffer solution containing 1.5 μg/ml of mouse monoclonal antibody specific for $β_3$ is prepared. To this solution was added the secondary antibody, which is anti-mouse-Fc-HRP antibody conjugate. For example, for one plate, 6 ml of a 1.5 μg/ml mouse Mab solution was prepared to which was added 1 μl of anti-mouse-Fc-HRP antibody stock, (this represents a 1:6000 dilution of the antibody—HRP conjugate). This mixture was allowed to incubate during the receptor-inhibitor incubation. The assay plates were washed 4 times with PBS-Tween and 50 μl/well of the antibody mixture was then pipetted into the plate for a 60 minute incubation. The plate was washed 4 times and the color reaction was developed with 50 μl /well of 0.67 mg/ml o-phenyldiamine in PBS containing 0.012% $H_2O_2$. Alternatively, 16 mM citric acid, 50 mM $Na_2PO_4$ at pH 5.0 can be used as a substrate buffer. The reaction is stopped with 50 μl/well 1 M $H_2SO_4$. The plates were read at 492–405 nm and the data analyzed by four-parameters fit.

5. Von Willebrand Factor—$GPII_bIII_a$ Receptor ELISA (VWf/$II_bIII_a$)

Microtiter plates were coated with 1.0 μg/ml $GPII_bIII_a$, prepared by the method of Fitzgerald et al., (Anal. Biochem. 151:169–177 (1985) ), incorporated herein by reference, and allowed to incubate overnight in coat buffer. The plates were then washed three times in wash buffer (0.05% Tween 20 in PBS) and 150 μl of assay buffer was added and allowed to incubate for 1–2 hours at room temperature on plate shaker. The plates were washed three times and 50 μl of 2× inhibitor in assay buffer (Assay buffer: 0.5% BSA/50 mM Trix, 100 mM NaCl, 1.0 mM $CaCl_2$, 1.0 mM $MgCl_2$, 1.0 mM $MnCl_2$; coat buffer was the same but with out BSA) was added. Fifty μl of 4.0 μg/ml vWF (prepared as described by Ledford et al., Thrombosis and Hemostasis, 64(4):569–575 (1990), incorporated herein by reference) in assay buffer was then added and allowed to incubate for one hour at room temperature on plate-shaker. The plates were washed three times and the antibody mixture was added (1:5000 of mouse anti-vWF and 1:5000 of rabbit-anti-mouse-Fc-HRP, both commercially available) in assay buffer and incubated for 1 hour at room temperature on plate-shaker. Plates were again washed three times and 100 μl of substrate solution (10 mg OPD, 6.5 μl $H_2O_2$, 15 ml phosphate citrate buffer) was added and incubated at room temperature. The color change of $OPD/H_2O_2$ reagent was read at 492 nm with a 405 nm reference wavelength on the filter photometer.

EXAMPLE IV

Liposome Attachment Assay for Vitronectin Receptor (Vn-R)

This assay was performed with minor modifications, according to the method of Pytela et al., Methods Enzymol. 144:475 (1987), incorporated herein by reference. Briefly, 1:4 mixture of labelled and unlabelled phosphatidylcholine (PC) liposomes was dissolved under nitrogen and diluted with an equal volume of purified receptor (purified as described in Example II) to achieve a fixed predetermined receptor-liposome concentration ratio. This mixture was then dialyzed overnight at 4° C. in phosphate buffered saline (PBS) containing 1 mM $Ca^{2+}$. An aliquot of the dialyzed sample was counted to assess radioactive content; the receptor-liposome mixture was then diluted to obtain a set radioactivity per unit volume.

Microtiter plates were coated with 10 μg of vitronectin. Non-specific sites were blocked for 2 hours at 37° C. in PBS containing 5 mg/ml BSA and 1 mM each of $CaCl_2$ and $MgCl_2$. The plates were then rinsed twice with PBS containing 1 mM $Ca^{+2}$ and $Mg^{+2}$, and 100 μl of the liposome-receptor mixture was added to each well. If necessary, peptides were added before this step in a 1–10% dilution. The plates were then incubated at 4° C. for 24 hours. The following day, the liquid in each well was aspirated and the plates were washed twice with PBS containing 1 mM $Ca^{+2}$ and $Mg^{+2}$. Finally, 100 μl of 2% SDS was added, the plates were shaken for 10–15 minutes, and the supernatants were collected, vortexed, and subjected to liquid scintillation counting. This procedure typically yielded ca. 1000 total and 100 non-specific counts per well.

EXAMPLE V

Platelet Aggregation and Potencies of Hydrophobically Enhanced RGD Peptides

Platelet aggregation assays were performed following the methods of this Example or those of Example IX.G. Platelet aggregation was assessed using the method of Born, (Nature 194:927–929 (1962)), incorporated herein by reference. Briefly, the change in light transmission was measured through a stirred suspension of platelets in an aggregometer (Model 400 VS, Chrono-Log, Havertown, Pa., USA). Studies employing ADP were performed with platelet-rich plasma (PRP), which was obtained by low-speed centrifugation (200×g for 10 min.) of whole blood freshly drawn into trisodium citrate (at a final concentration of 11 mM). In studies using thrombin, the PRP was gel-filtered on Sepharose 2B in divalent ion-free Tyrode's solution containing 2% BSA. For all studies, the reference standard was platelet-poor plasma, which was obtained by centrifuging PRP at 1000×g for 5 min.

All aggregation studies were performed at 37° C. with a constantly stirred suspension of 3×10$^8$ platelets/ml. (Platelet count was determined with the aid of a hemacytometer.) Peptides and stimulants were added to these suspensions in 1% dilutions. The PRP and gel-filtered platelets were used within three hours from the time of blood collection.

Peptide anti-aggregation potencies were determined from dose-responsive curves for the inhibition of the maximum aggregation responses stimulated by physiologic doses of ADP (10 μm) and thrombin (2 U/ml). The 50% inhibitory concentration of each peptide (IC$_{50}$) was determined by regression analysis of these curves.

In an independent study, a slightly modified aggregation assay was used. The modified method was as follows and the results are shown in Table II. Platelet aggregation assays were performed in human platelet rich plasma (PRP). Fifty milliliters of whole human blood (9 parts) was drawn on 3.6% sodium citrate (1 part) from a donor who had not taken aspirin or related medications for at least two weeks. The blood was centrifuged at 160×g for 10 minutes at 22° C. and allowed to stand for 5 minutes after which the PRP was decanted. Platelet poor plasma (PPP) was isolated from the remaining blood after centrifugation at 2000×g for 25 minutes. The platelet count of the PRP was diluted to about 300,000 platelets per microliter with PPP.

A 225 μl aliquot of PRP plus 25 μl of either a dilution of the test inhibitor sample or a control (PBS) was incubated for 5 minutes in a Chrono-log Whole Blood Aggregometer at 37° C. An aggregating agent (collagen, 1 μg/ml; U46619, 100 ng/ml; or ADP, 17 μM) was added and the transmission was recorded.

The hydrophobically enhanced RGD peptides have been grouped into four distinguishable classes for systematic comparison. They are (1) cyclic RGD peptides which vary the size and hydrophobicity of the amino acid at the position immediately following the Asp residue in the tripeptide RGD (the first and last position as depicted in Table I may vary by substitution with Arg); (2) cyclic RGD peptides which vary the size and hydrophobicity of the bridging structure for cyclization; (3) cyclic RGD peptides which vary the size and hydrophobicity of both the bridging structure and the residue immediately following the Asp residue in the tripeptide RGD and (4) cyclic RGD peptides which fall into one of the above three classes and also vary the charge at the residue adjacent to the hydrophobic amino acid. Other RGD peptides, both linear and cyclized, are included in Table I for comparison. Underlining indicates a bridge between the first and last residue included in the underlined portion.

As shown in Table I, each class of cyclized, hydrophobically enhanced RGD peptide analogues demonstrated inhibitory effects on platelets stimulated with thrombin or ADP. Eight analogues had inhibitory potencies (IC$_{50}$) less than or approximately equal to 10 μm against thrombin-stimulated platelet aggregation while as many as twenty-two demonstrated inhibitory potencies in this range for the ADP-stimulated response. For example, the inclusion of hydrophobic residues phenylalanine (F) and tryptophan (W) in the "X" position of template structures GPenGRGD-X-PCA (SEQ ID NO. 42) and GPenGHRGD-X-RCA (SEQ ID NO. 43) imparted greater anti-aggregation inhibitory potency relative to GPenGRGDSPCA (SEQ ID NO. 44) and GPenGHRGDLRCA. This effect was further enhanced by other non-natural hydrophobic structures, such as para-chloro-phenylalanine (PheCl), and para-methyl-tyrosine (TyrMe) O-n-hexyl-tyrosine, 3,5 -diiodo-tryosine, O-n-butyl-tyrosine, p-nitro-phenylalanine and the like in the same position. The inclusion of positively charged amino acids such as arginine (R) or lysine (K) in the "X" positions of XPen-GRGDSPCA (SEQ ID NO. 45) or (X-PenGHRGDKRCA (SEQ ID NO. 46) also increased anti-aggregation potency. Moreover, the inclusion of a positively charged amino acid outside the cyclic structure also yielded peptides with high potency.

Organic mimic bridging structures were substituted for penicillamine and Pmp in the "X" position of the template structure G-X-GHRGDLRCA (SEQ ID NO. 47). When substituted alone, tert-butyl-Pmp and amino-Pmp lessened peptide anti-aggregation potency. On the other hand, peptide derivatives containing these amino acids and an N-terminal R significantly out-performed the previously disclosed cyclic RGD structures GPenGHRGDLRCA and PmpGHRGDLRCA, in platelet aggregation assays. Finally, replacement of 1-Pen in G(1-Pen)GHRGDLRCA (SEQ ID NO. 48) by the d-form of penicillamine lowered anti-aggregation potency by 2-fold.

The modifications described above have resulted in inhibitory potencies 10 to 250-fold more potent than the prototype GRGDSP (SEQ ID NO. 49) linear peptide and 2 to 5-fold more potent than the initial conformationally restrained cyclic peptide GPenGRGDSPCA. The results from the independent study, shown in Table II, further corroborate these conclusions.

TABLE I

Potencies of Hydrophobically Enhanced RGD Peptide Analogs Against Platelet Aggregation and Receptor Binding

| Peptide (SEQ ID NOS. 49, 44, 50, 51, 42, 42, 52, 5, 53, 6, 7, 54, 8, 55, 167, 56 and 9, respectively) | Thrombin Stimulated Aggregation | ADP-Stimulated Aggregation | FnR Binding | VnR Binding | IIb/IIIa Binding |
|---|---|---|---|---|---|
| GRGDSP | | 135 ± 15 | 0.032 ± 0.006 (4)* | 0.70 | 50 |
| G(Pen)GRGDSPCA | | 27.5 | 0.015 | 0.15 | 0.29 |

TABLE I-continued

Potencies of Hydrophobically Enhanced RGD Peptide
Analogs Against Platelet Aggregation and Receptor Binding

| | | | | | |
|---|---|---|---|---|---|
| G(Pen)GRGDTPCA | 28 | 22.3 | .063 | 0.033 | |
| G(Pen)GRGDLPCA | | 19.3 | 0.96 | 0.073 | |
| G(Pen)GRGDFPCA | | 3.5 | .084 | 2.7 | 4.1 |
| G(Pen)GRGDWPCA | | 1.6 | 0.13 | 12.7 | |
| R(Pen)GRGDWPCR | 0.53 | 0.65 | 0.014 | 4.2 | 0.098 |
| G(Pen)GHRGDLRCA | 18 | 15 | 10 | 1.2 | 10 |
| R(Pen)GHRGDLRCR | 3.2 | 10.3 | 5.9 | 37.1 | 6.2 |
| R(Pen)GHRGDWRCR | 1.2 | 1.3 | 7.3 | 6.9 | 0.80 |
| R(Pen)GHRGD(Cha)RCR | | 4.1 | 3.9 | 10 | |
| R(Pen)GHRGD(1-Nal)RCR | | 29 | 10 | | |
| (Pmp)GHRGDLRCA | 6.3 | 7.2 | 0.34 | 10 | |
| G(am-Pmp)GHRGDLRCA | | 83 ± 23 (2) | 3.4 | | |
| (t-but-Pmp)GHRGDLRCA | | 120 | 1.1 | | |
| (t-but-am-Pmp)GHRGDLR(Pen)A | | 89 | | | |
| G(dPen)GHRGDLRCA | | 6.28 ± 0.7 (2) | 1.5 | 5.3 | 1.4 |

| Peptide (SEQ ID NOS. 10, 10, 11, 12, 57, 13, 13, 14, 14, 58–69, 1 and 70–77, respectively) | Thrombin Stimulated Aggregation | ADP-Stimulated Aggregation | FnR Binding | VnR Binding | IIb/IIIa Binding |
|---|---|---|---|---|---|
| R(am-Pmp)GHRGDWRCR-1 | | 1.4 | 1.7 | 5.9 | 0.06 |
| R(am-Pmp)GHRGDWRCR-2ª | | 1.4 | 1.7 | | |
| R(am-Pmp)GHRGD(TyrMe)RCR | | 0.45 | 2.1 | 1.0 | 0.018 |
| R(am-Pmp)GHRGD(PheCl)RCR | | 0.65 | 1.2 | 10 | 0.02 |
| R(am-Pmp)RGD(Cha)CR | | <200* | 0.35 | | |
| R(am-Pmp)GHRGDLRCR-1 | 1.3 | 1.5 | 1.1 | 6.7 | 0.4 |
| R(am-Pmp)GHRGDLRCR-2ª | 1.3 | 1.5 | 2.9 | | |
| R(t-but-am-Pmp)GHRGDLRCR-1 | | 1.9 | 2.2 | | |
| R(t-but-am-Pmp)GHRGDLRCR-2ª | | 1.9 | 2.2 | 3.7 | 0.06 |
| R(am-Pmp)GRGDWPCR | | 1.2 | 0.05 | 0.84 | 0.025 |
| R(Pmc)GHRGD(O-n-hexyl-Tyr)RCR | | 0.96 | 2.0 | | |
| R(Pmcghrgd(3,5-diiodo-Tyr)RCR | | 1.10 | 6.1 | 0.9 | 0.013 |
| R(Pmc)GHRGD(Hpa)RCR | | 1.15 | 1.81 | 4.2 | 0.02 |
| R(Pmc)GHRGD(O-n-butyl-Tyr)RCR | | 0.35 | 6.60 | 2.20 | 0.028 |
| R(Pmc)GHRGD(p-nitro-Phe)RCR | | 0.38 | 5.74 | 6.05 | 0.023 |
| R(Pmc)GHRGDVRCR | | 0.69 | 2.30 | 2.00 | 0.15 |
| R(Pmc)GHRGDFRCR | | 0.62 | 8.70 | 10.00 | 0.043 |
| R(Pmc)GHRGDYRCR | | 1.00 | 10.00 | 7.85 | 0.153 |
| R(Pmc)GHRGD(O-Me-Tyr)RCR | | 0.44 | 7.72 | 6.20 | 0.068 |
| R(Pmc)GHRGD(Phg)RCR | | 0.68 | 1.23 | 0.79 | 0.023 |
| R(Pmc)GHRGD(O-Me-Tyr)RCR | | 0.83 | 6.40 | 9.90 | 0.06 |
| F(Pmc)GHRGD(O-Me-Tyr)RCR | | 0.73 | 8.70 | 6.04 | 0.07 |
| R(dPen)GHRGD(p-iodo-Phe)RCR | | 0.78 | 4.37 | 10.00 | 0.023 |
| K(Pmc)GHRGD(O-Me-Tyr)RCK | | 0.83 | 8.60 | 3.90 | 0.029 |
| R(Pmc)GHRGD(O-Me-Tyr)OCR | | 0.91 | 8.40 | 9.30 | 0.007 |
| H(Pmc)GHRGD(O-Me-Tyr)RCR | | 0.94 | 8.30 | 8.40 | 0.079 |
| R(Pmc)GHRGD(p-amino-Phe)RCR | | 0.99 | 9.01 | 10.00 | 0.34 |
| R(Pmc)NHRGD(O-Me-Tyr)RCR | | 0.99 | 4.70 | 6.90 | 0.098 |
| G(Pmc)GHRGD(O-Me-Tyr)RCR | | 1.10 | 10.00 | 10.00 | 0.104 |

| Peptide (SEQ ID NOS. 78–84, 2, 3, 85, 86, 16 and 87–103, respectively) | Thrombin Stimulated Aggregation | ADP-Stimulated Aggregation | FnR Binding | VnR Binding | IIb/IIIa Binding |
|---|---|---|---|---|---|
| R(Pmc)GHRGD(O-Me-Tyr)KCR | | 1.10 | 10.00 | 10.00 | 0.047 |
| G(Pen)IARGDWNCA | | 1.20 | 0.71 | 0.040 | 0.01 |
| T(Pmc)GHRGD(O-Me-Tyr)RCR | | 1.25 | 10.00 | 10.00 | 0.052 |
| R(Pmc)GHRGD(p-nitro-Phe)KCR | | 1.40 | 3.10 | 10.00 | 0.10 |
| R(Pmc)GHRGD(p-iodo-Phe)KCR | | 1.50 | 5.50 | 8.00 | 0.063 |
| Ac(Pmc)GHRGD(O-Me-Tyr)RC-NH$_2$ | | 1.61 | 9.70 | 10.00 | 0.40 |
| D(Pmc)GHRGD(O-Me-Tyr)RCR | | 1.75 | 10.00 | 8.85 | 0.22 |
| AcCIPRGD(O-Me-Tyr)RC-NH$_2$ | | 0.17 | 4.28 | 5.75 | 0.003 |
| AcCNPRGD(O-Me-Tyr)RC-NH$_2$ | | 0.22 | 8.20 | 4.70 | 0.029 |
| Ac(dPen)IPRGD(O-Me-Tyr)RC-NH$_2$ | | 0.28 | 4.31 | 4.32 | 0.0023 |
| Ac(dPen)NPRGD(O-Me-Tyr)RC-NH$_2$ | | 0.17 | 6.75 | 6.71 | 0.0010 |
| AcCNPRGD(O-n-butyl-Tyr)RC-NH$_2$ | | 0.10 | 1.53 | 10.00 | 0.006 |
| R(dPen)NPRGD(O-Me-Tyr)RCR | | 0.12 | 10.00 | | 0.0012 |
| GRGDSPDG | | 32 | 0.05 | 0.10 | 0.25 |
| FRGDSPDG | | 110 | 2.4 | 0.04 | |
| YRGDSPDG | | 83 | 1.1 | 0.08 | |
| LRGDSPDG | | 150 | 1.2 | 0.2 | |
| dSRGDSPDG | | 54 | .075 | 0.07 | |
| VRGDSPDG | | 92 | 0.04 | 0.24 | 0.27 |
| G(Pen)GRGDRPCA | | 22.3 | 1.3 | 0.47 | |

TABLE I-continued

Potencies of Hydrophobically Enhanced RGD Peptide
Analogs Against Platelet Aggregation and Receptor Binding

| | | | | | |
|---|---|---|---|---|---|
| G(Pen)LRGDTPCA | | | 86 | 1.9 | 0.25 |
| G(Pen)VRGDSPCA | | | 45 | | |
| G(Pen)YRGDSPCA | | | 47 | | |
| G(Pen)LRGDSPCA | | 308 | 415 | 0.54 | 0.26 | 0.48 |
| G(Pen)LRGDSRCA | | 49 | 41 | 1.1 | 1.35 | |
| G(Pen)GRGDSFCA | | | 115 | | 0.02 |
| G(Pen)FRGDSFCA | | | <200 | 0.33 | 0.05 | 3.4 |
| G(Pen)GRGDRPCR | | | 22.0 | 0.26 | 0.01 |
| R(Pen)GRGDTPCA | | 3.1 | 7.0 | 0.08 | 0.03 |

| Peptide (SEQ ID NOS. 104–124, respectively) | Thrombin Stimulated Aggregation | ADP-Stimulated Aggregation | FnR Binding | VnR Binding | IIb/IIIa Binding |
|---|---|---|---|---|---|
| K(PenGRGDTPCA | | 10.3 | 0.03 | 0.015 | |
| R(Pen)GRGDTPCR | 2.0 | 6.3 | .027 | 0.01 | |
| R(Pen)GRGDTPCK | | 7.6 | 0.49 | | |
| R(Pen)GRGDSRCA | 12 | 12 | | | |
| R(Pen)GRGDLRCA | 13 | 16 | | | |
| G(Pen)GHRGDTRCA | 17 | 11.3 | 2.9 | | |
| R₂(Pen)GRGDTPCA | 2.7 | 8.2 | | | |
| R(Pen)GHRGDTRCR | | 8.8 | | | |
| L(Pen)GHRGDLRCA | | 10.5 | 4.9 | | |
| (Pmp)GRGDSPCA | | 45 | .023 | 0.10 | 0.58 |
| (Pmp)GHRGDLR(Pen)A | | 5.8 | .078 | 5.2 | 0.55 |
| (t-butylAmino-Pmp) GHRGDLRCA | | 130 | 1.5 | | |
| R(AminoPmp)GRGDTPCA | | | 0.03 | | |
| GHRGDLRDASG | | 7.5 | 4.9 | | |
| RKGHRGDLRDR | | 75 | 1.3 | | |
| R(orn)GHRGDLRDRASG | | 24 | 22 | | |
| R(orn)GHRGDLRDR | | <200 | | | |
| R(orn)GHRGDLRER | | 44 | 1.7 | | |
| GHRGDLR(Pas)A-NH₂ | | 4.8 | 3.2 | | |
| R₉GDS | | 28 | 0.64 | | |

*concentrations unconfirmed by amino acid composition analysis
ᵃRepresents second peak after HPLC purification of synthesized peptides using a racemic am-Pmp mixture.

TABLE II

In Vitro Integrin ELISA Results

| Code | IC50 ($\mu$M) Human Platelet Aggregation | IC50 (nM) Fg/II$_b$III$_a$ | Vn/VnR | vWF/II$_b$III$_a$ | Fn/FnR | Sequence (SEQ ID NOS. 3, 125–28, 15, 129–131, 5, 88, 6, 1, 132, 133, 64, 2 and 86, respectively) |
|---|---|---|---|---|---|---|
| 8X | 0.22 | 8.7 | 4700 | 14.8 | 8200 | Ac-CNPRGD(Y-OMe)RCNH₂ |
| 11J | 3.4 | 17.3 | 48 | 6.4 | 6200 | Ac-CNPRGD(Y-OMe)EC-NH₂ |
| 11K | 4.5 | 36 | 30 | 9.3 | 840 | Ac-CNPRGD(Y-OMe)AC-NH₂ |
| 11L | 7.3 | 932 | 1818 | 640 | <10000 | Ac-CNPRGD(Y-OMe)(dR)C-NH₂ |
| 11P | 4.9 | 44.5 | 63.5 | 9.9 | 440 | Ac-CNPRGD(Y-OMe)OC-NH₂ |
| 11Q | 0.79 | 55 | 20000 | 60.2 | 5600 | Ac-CNPKGD(Y-OMe)RC-NH₂ |
| 11R | 1.0 | 96 | 705 | 89.9 | 1560 | Ac-CNPRGD(Y-OMe)KC-NH₂ |
| 11S | 7.3 | 102 | 891 | 27.1 | 440 | Ac-CNPRGD(Y-OMe)(Cit)C-NH₂ |
| 11V | 7.6 | 15.2 | 108 | 18.6 | (not tested) | Ac-CNPRGD(Y-OMe)(Nle)C-NH₂ |
| 2G | 14 | | | | | G(Pen)GHRGDLRCA |
| 2H | 20 | | | | | GRGDSPDG |
| 4Q | 3.3 | | | 86.6 | | R(Pen)GHRGDWRCR |
| 5O | 0.56 | | | 15.7 | | R(Pmc)GHRGD(Y-OMe)RCR |
| 6Z | 58 | | | | | G(Pen)RARGDNPCA |
| 7B | 0.70 | | | 11.8 | | R(Pmc)GHRGD(p-I-F)RCR |
| 7T | 0.38 | | | 29 | | R(Pmc)GHRGD(p-NO₂-F)RCR |
| 10R | 0.17 | | | | | AcCIPRGDY-OMeRCNH₂ |
| 10X | 0.17 | | | | | Ac(dPen)NPRGDY-OMeRCNH₂ |

EXAMPLE VI

Peptide Receptor Selectivity

In parallel studies with the platelet aggregation experiments (described in Example V), the apparent affinities of peptides for GP IIb/IIIa, fibronectin and vitronectin receptors were determined. Receptor-binding assays (as described in Examples III and IV) with purified receptors, were used to assess the abilities of the peptides to displace the binding of receptors to their receptor-specific ligands.

Shown in Table I, as a comparison with platelet inhibitory potencies, are the relative affinities of each peptide for the receptors shown.

The binding data are again represented as the 50% inhibitory concentration of each peptide ($IC_{50}$s) and were determined as described in Example V for the dose-response curves for the inhibition of platelet aggregation. $IC_{50}$s for FnR were determined by ELISA (Example III). Those for VnR and GP IIb/IIIa were determined either by ELISA or liposome attachment assay (Example IV). The GRGDSP prototype peptide is used as a reference for comparison between assays for an individual peptide.

Table II provides the receptor binding data as a comparison with the platelet inhibitory potencies shown therein. This data is also represented as the 50% inhibitory concentration of each peptide. The values for all receptor assays were determined by ELISA as described in Example III. The results shown in Table II further corroborate the conclusions drawn from Table I, namely, that the anti-aggregation potencies are parallel by their relative affinity for the IIb/IIIa receptor.

EXAMPLE VII

Efficacy Against Electrically Induced Canine Coronary Thrombosis

1. Surgical Preparation and Instrumentation

Male mongrel dogs weighing 14 to 20 kg were selected based on proper aggregation of their platelets in response to arachidonic acid, collagen, and adenosine disphosphate (ADP) and based on similar weights and hemodynamic properties.

Before surgery, the animals were anesthetized with sodium pentobarbital (30 mg/kg, i.v.) and then intubated and ventilated on room air with positive pressure using a respirator (Harvard Apparatus, S. Natick, Mass.) at a volume of 30 ml/kg and a frequency of 12 breaths/min. Surgery, performed under aseptic conditions, was begun with the placement of cannulae into the left carotid artery and jugular vein for monitoring arterial blood pressure (Statham P23 pressure transducer, Gould, Inc., Cardiovascular Products, Oxnard, Calif.) and administering intravenous fluids.

The heart was exposed via a left thoracotomy through the 5th intercostal space. A 2-cm segment of the left circumflex coronary artery (LCCA) was isolated from surrounding tissue by blunt dissection. This artery was instrumented from proximal to distal with an electromagnetic flow probe (Model 501, Carolina Medical Electronics, Inc., King, N.C.), intra-coronary electrode, and screw occluder (see FIG. 1). The intra-coronary electrode was constructed by attaching a 25-gauge hypodermic needle tip to a 30-gauge Teflon-insulated silver-coated copper wire. The mechanical occluder was constructed of stainless steel in a C shape with a Teflon screw (2 mm diameter) on top. It was adjusted to control vessel circumference and decrease the reactive hyperemic flow due to a 10-sec (full) occlusion by 50–70% without affecting basal coronary blood flow (FIG. 1). A monopolar epicardial electrode was sutured to the surface of the ventricle in the region of LCCA distribution to monitor ischemic changes in the electrocardiogram (ECG). The left atrium was cannulated with polyethylene tubing for administration of the peptide. Continuous recordings of blood pressure, limb lead II ECG, epicardial electrogram, and mean and phasic LCCA blood flow were obtained on a Model 7 polygraph (Grass Instrument Co., Quincy, Mass.).

2. Induction of Coronary Thrombosis

One hour after the completion of surgery, a 100 microamp continuous anodal direct current delivered from a 9 volt nickel-cadmium battery was applied to the intimal surface of the LCCA. The anode of the battery was in series with a 250,000 ohm potentiometer and the intraluminal coronary artery electrode. The electric circuit was completed by placing the cathode in a subcutaneous site. Electrical stimulation was applied for three hours. At the conclusion of each experiment, the heart was fibrillated electrically and quickly removed, and the LCCA was dissected free as far as possible to verify the position of the implanted anodal electrode.

For all ex vivo studies (see FIG. 3), control aggregation values were standardized to the percentages of light transmission observed in PRP and PPP samples (0% and 100%, respectively).

3. Peptide Administration

Animals were randomly assigned to two treatment groups: vehicle control (i.e., normal saline) or RGD peptides at various concentrations. Peptides were administered intra-atrially in both bolus and continuous injections. Each bolus injection consisted of 0.5 to 10 mg/kg and was administered 15 minutes before application of the current. A continuous infusion of the same peptide was then started immediately after completion of this initial injection. Animals received a 25 $\mu$g/kg/min to 200 $\mu$g/kg/min infusion. The anti-thrombotic effects of the peptides were monitored until 30 minutes after the occurrence of a persistent, occlusive thrombus or five hours after the initiation of electrical stimulation (whichever resulted first). If an occlusive thrombus had not developed within four hours after the initiation of current, the peptide infusion was stopped.

4. Platelet Studies

Platelet counts and ex vivo aggregation studies were performed one hour before and 1, 3, and 5 hours after application of anodal direct current. Samples of arterial blood were drawn into plastic syringes containing 3.8% trisodium citrate (giving a 1:10 final dilution) and platelet aggregation determined as described in Example V.

Figure 2B:
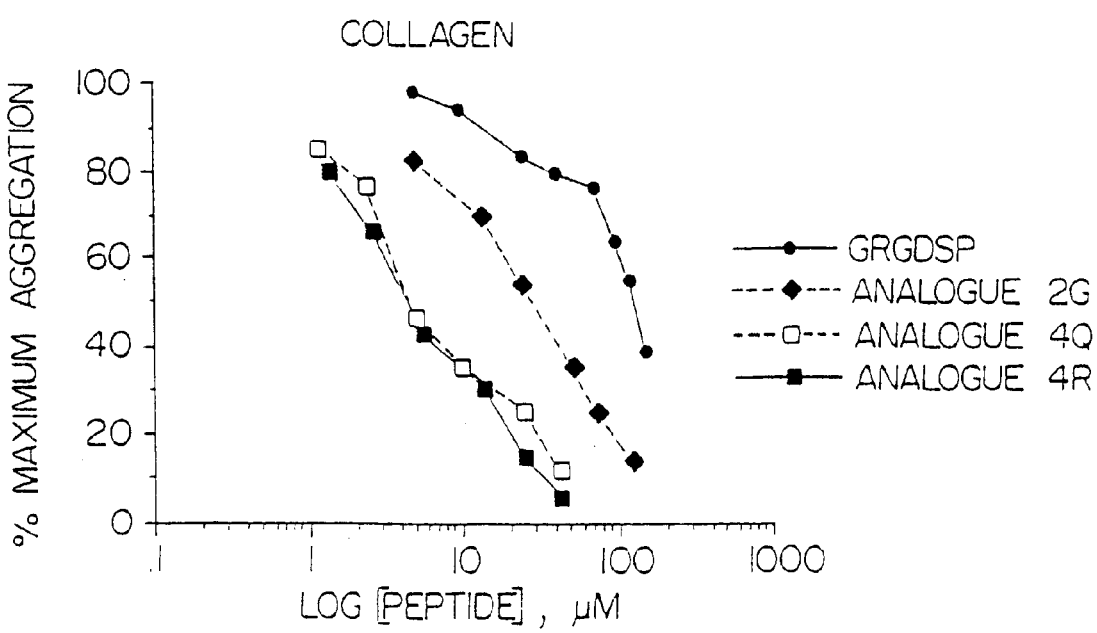
Figure 2C:
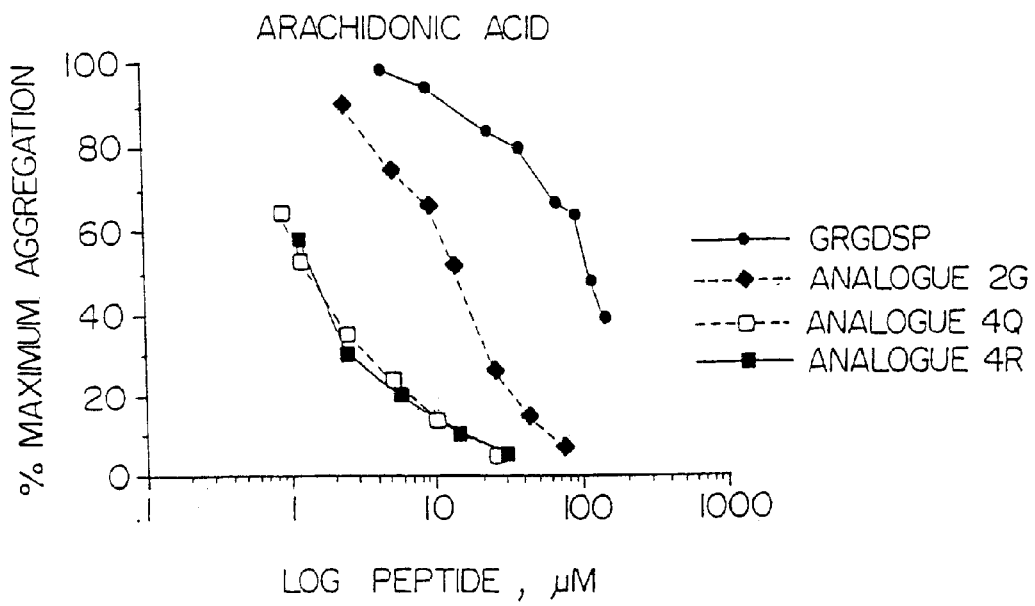

The inhibitory potencies of peptide analogues 2 G(G(Pen) GHRGDLRCA), 4Q(R(Pen)GHRGDWRCR), and 4R (R(Pen)GRGDWPCR), as well as the generic analogue GRGDSP, were determined against canine platelet aggregation stimulated maximally by 10 $\mu$m ADP, 0.65 mM arachidonic acid (AA), or 9.6 micrograms/ml collagen. Epinephrine (550 nM) was used to prime platelets before stimulation with arachidonic acid. Peptides were added in 1% dilutions to the PRP solutions. The relative anti-aggregation potencies of all injected peptides and the generic analog GRGDSP were determined at the 1 hour before current time point, with dose-response analysis (see FIG. 2). The peptide concentrations causing 50% inhibition of maximal activation ($IC_{50}$s) were derived by linear regression of these dose-response curves. For computation of these inhibitory potencies, control values (i.e., in the absence of peptide) were considered as 100% of maximum.

As shown, analogues 4Q and 4R exhibited superior potencies, inhibiting aggregation by 50% at 1.5–5 $\mu$m. Analogue 2G was slightly less potent, with $IC_{50}$s of 15–30 $\mu$m, whereas GRGDSP inhibited all three responses by 50% at ca. 130 micromolar. Notably, the potency order (4Q= 4R>2G>GRGDSP) and $IC_{50}$s of these peptides against these responses were the same as those observed for their inhibition of ADP-, collagen-, and arachidonic acid-stimulated aggregation of human platelets.

Platelet aggregation was also determined ex vivo at one, three, and five hours after current application. For these studies, arachidonic acid, or collagen was again used to stimulate the platelets.

The average aggregation values determined in these studies for all of the peptide treatments are depicted in FIG. 3.

Figure 3A:
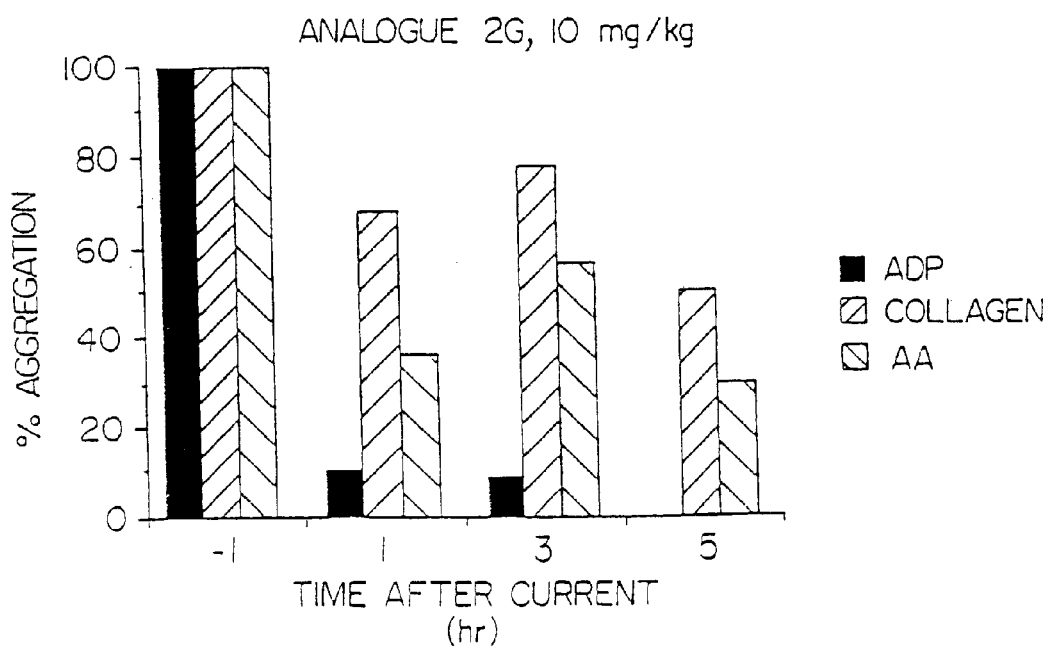
FIG. 3 (A–C) shows the platelet aggregation values for each peptide dose following time after induction of coronary thrombosis.
Figure 3B:
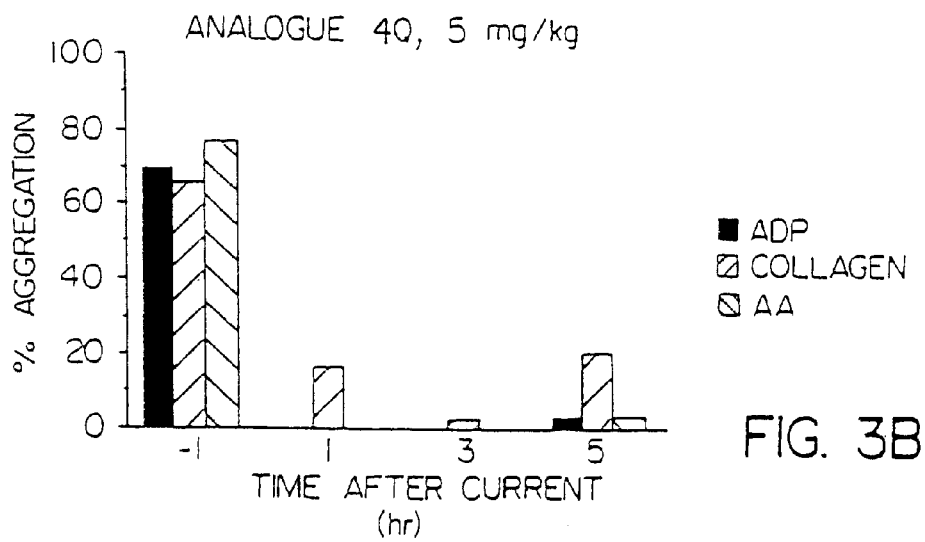
Figure 3C:
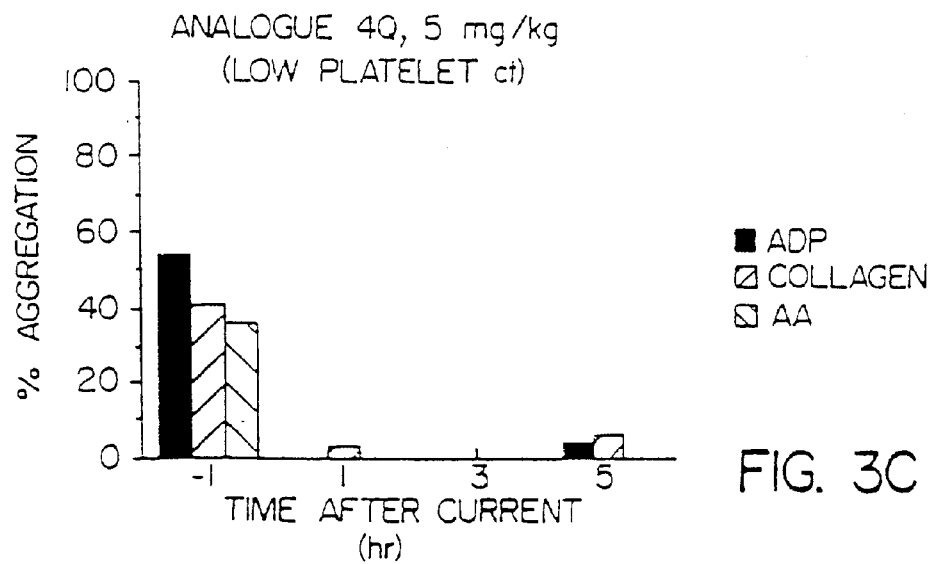
Figure 3D:
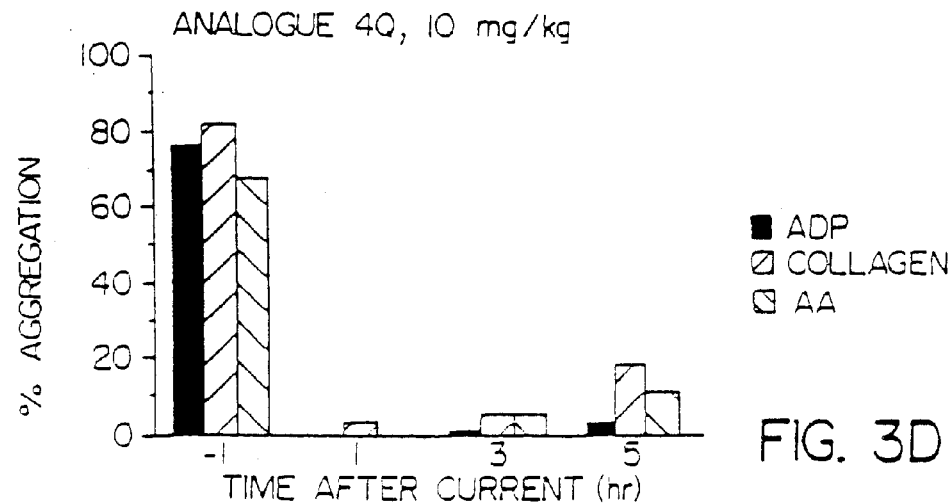
Figure 3E:
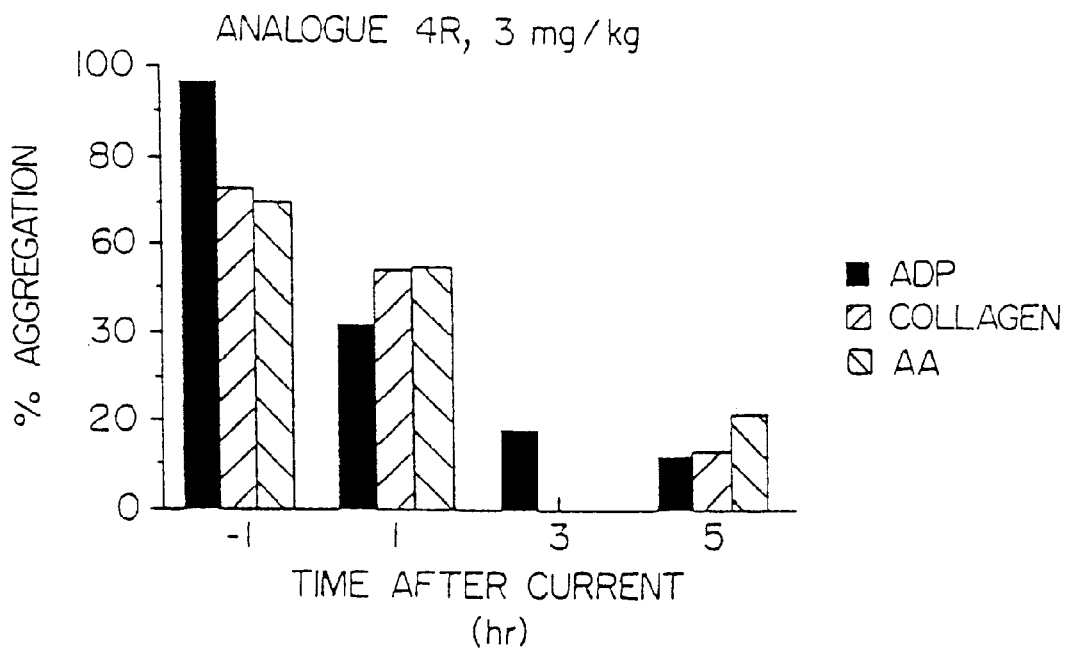
Figure 3F:
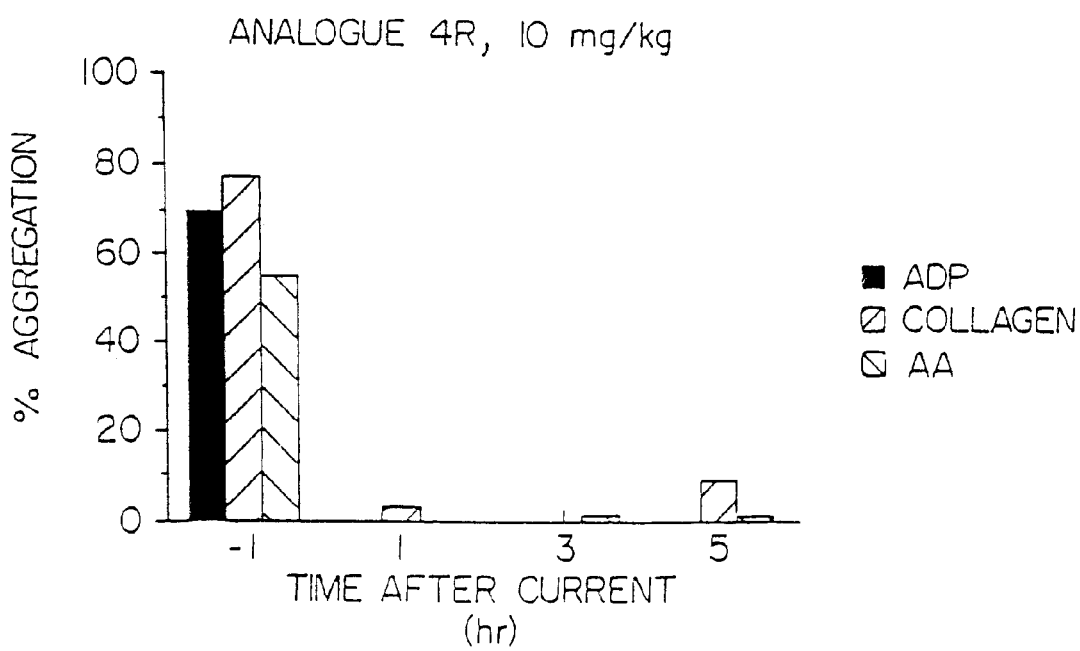

(In these histograms, 0% and 100% aggregation represent the extent of light transmission through PRP and PPP, respectively, before the addition of stimulant.) Analogue 2G, when injected at 10 mg/kg, substantially inhibited ADP-stimulated aggregation but only partially inhibited the AA- and collagen-stimulated responses (43–70% and 12–50%, respectively, relative to control levels) at all three time points (FIG. 3a). As shown in FIGS. 3b and 3c, the ex vivo anti-aggregation effects of analogues 4Q and 4R were far superior. A 5 mg/kg injection of analogue 4Q made the platelets completely unresponsive to stimulation with ADP and AA at all three time points and caused near-maximal inhibition of their activation by collagen. (Here, the absence of a coded bar indicates the absence of the corresponding response.) As shown in FIG. 3b, the effects of this same peptide at the same injection were more pronounced when platelet count was low, i.e., ca. one-third of normal (104, 000/ml vs. 361,000/ml). At a higher injected concentration (10 mg/kg), analogue 4Q prevented platelet aggregation by all three stimuli at one- and three-hour time points. At the five-hour point, platelet responsiveness was slightly improved. The control responses in these studies were 70–80% of maximum. As shown in FIG. 3c, analogue 4R, at 3 mg/kg, exerted an apparent time-dependent effect on platelet responsiveness in that aggregation was reduced only 20–58% at one hour but 75–100% at three and five hours relative to control levels. Finally, a 10 mg/kg injection of this analogue caused the platelets to be unresponsive to all modes of stimulation at all time points. Here the control responses were 55–80% of maximum.

5. Peptide Effects on Coronary Blood Flow and Thrombosis

Coronary thrombosis was quantified as the time to full occlusion. The effects of the various peptide treatments on coronary thrombosis is illustrated in FIG. 4. In the control situation (saline injections), a full occlusion was observed in slightly more than two hours. Analogue 2G, even at 10 mg/kg, did not significantly influence this frequency. Analogue 4Q at 5 mg/kg significantly prolonged the time to occlusion and at 10 mg/kg completely prevented occlusion for the full five-hour experimental period. Moreover, at the low dose (5 mg/kg), analogue 4Q was able to prevent thrombus formation in animals whose circulating platelet levels were one-third of normal. Analogue 4R at 10 mg/kg prevented occlusion throughout the duration of the study but at 3 mg/kg was ineffective.

In these studies, the degree of anti-thrombotic efficacy appeared to coincide with the anti-aggregation potency described above. For example, analogues 4Q and 4R, which were superior inhibitors of in vitro aggregation, also exerted a considerably greater in vivo protective effect than analogue 2G at the same injected concentration. Moreover, these peptides were able to prevent full occlusion only when they completely prevented platelet stimulation by all of the agonists (at 10 mg/kg). However, analogue 4Q (at 5 mg/kg) completely or near-maximally blocked all aggregation responses but could merely prolong coronary occlusion. In addition, analogue 4R at 3 mg/kg blocked aggregation responses by 72–100% at the three- and five-hour points, yet at these times an occlusive thrombus had fully developed. Finally, these peptides could completely prevent occlusion in this model only at injected concentrations equivalent to 20- to 50-fold greater than their $IC_{50}$s against in vitro aggregation.

6. Hemodynamic Responses

Bleeding time was quantified at 1 hour before and one, three, and five hours after administration of the peptide. This was done by making a small (5 mm long and 1.5 mm deep) incision in the tongue and subsequently absorbing the exuded blood at this site every 15 seconds with a piece of Whatman filter paper until bleeding stopped. Platelet counts were determined with a Haema Count MK-4/HC platelet counting system.

It is important to note that these apparently excessive peptide concentrations did not exert any significant effects on template bleeding time, platelet counts, or on the main hemodynamic parameters (heart rate and blood pressure), which remained essentially unchanged and similar to baseline values throughout the experimental periods (FIG. 5). In cases where peptide treatment did not prevent occlusion, at certain times these parameters were not determined (ND in Table II), as experiments were terminated 30 min. after circumflex coronary artery blood flow had ceased due to occlusive thrombus formation.

EXAMPLE VIII

Anti-Thrombotic Properties of Hydrophobically Enhanced RGD Peptides in Prosthetic Arterial Grafts Adult male baboons (weighing 16 to 25 kg) were used in these studies. These were sedated with ketamine hydrochloride (200 to 250 mg intramuscular injection) and maintained under anesthesia with sodium pentobarbital (50 to 75 mg administered intravenously as necessary).

Twenty-four hours before the ex vivo shunt was established, platelets were isolated from 500 ml of blood from the test animal and labelled with ca. 500 microcuries of indium-111 oxine (Medi+Physics, Emeryville, Calif.), which irreversibly and specifically binds to platelets with an efficiency of 50%. Immediately after labelling, these platelets were then injected back into the animal and allowed to circulate for 24 hours. Immediately before the start of the study, fibrinogen that had been isolated from the animal and labelled with iodine-131 (DuPont Nuclear, Boston, Mass.) was also injected back into the animal. Also at this time, baseline determinations of the clotting and template bleeding times were made, and blood samples were drawn for hematology studies.

To establish the ex vivo shunt, the femoral artery and vein were percutaneously cannulated with introducer catheters (KMA Inc., Mansfield, Mass.). The catheters were then connected to medical-grade, heparin-coated silastic tubing (2.59 mm internal diameter, (Extracorporeal Medical Specialties, Inc., King of Prussia, Pa.). An electromagnetic flow probe was then inserted into the tubing by varying the resistance imparted by a partially occluding screw clamp that was distal to the probe. Finally, a 5 cm-long test segment of a 4 mm (internal diameter) vascular graft was inserted at the apex of the circuit. The graft used in these studies was Gore-tex (expanded polytetrafluoroethylene, (W. L. Gore and Associates, Inc., Flagstaff, Ariz.). An electromagnetic flow probe was then inserted into the tubing circuit to measure blood flow, which was maintained at 100 ml/min. by varying the resistance imported by a partially occluding screw clamp that was distal to the probe. Finally, a 5 cm-long test segment of a 4 mm (internal diameter) vascular graft was inserted at the apex of the circuit. The graft used in these studies was Gore-tex (expanded polytetrafluoroethylene, W. L. Gore and Associates, Inc., Flagstaff, Ariz.).

Platelet deposition onto the grafts was monitored by dynamic scanning with a gamma camera (Sigma 400, Ohio Nuclear, Inc., Sohon, Ohio), which detects the gamma radiation emitted by the $^{111}$indium-labelled platelets. Once the circuit was in place, the animal was placed under this camera, and blood flow was initiated. Scans were then taken at the rate of one frame per two minutes for two hours. The data from these scans were collected on a dedicated Digital MDA computer (Maynard, Mass.). The scans were corrected for graft size, isotope dose and decay, circulating platelet activity and background, and the surface areas of the grafts.

At one- and two-hour time points, template bleeding times were measured, and blood samples were drawn to assess the hematology aggregation studies. Platelet aggregation studies were performed as described in Example V using ADP as the stimulus.

After a second, identical shunt was attached to the animal, the anti-platelet peptide GPenGHRGDLRCA was administered as an intravenous (IV) injection. A second series of scans was then obtained to ascertain the effect of the peptide on the platelet uptake pattern of the graft.

Upon the completion of each study, each shunt was flushed with lactated Ringer's solution, and each graft was then removed. Sections of these grafts were subjected to liquid scintillation counting to determine their content of residual $^{131}$iodine-fibrinogen and $^{111}$indium-platelets. The catheters in the femoral artery and vein were then removed, and hemostasis was achieved by compression. Finally, post-procedural blood samples were drawn, and determinations of template bleeding and clotting times were also made.

Three different animals were used in order to account for animal variability. Two of the three test animals displayed normal platelet uptake patterns, as determined from gamma camera images of $^{111In}$-labeled platelets on the graft material. Treatments for these two animals are described below.

Figure 6:
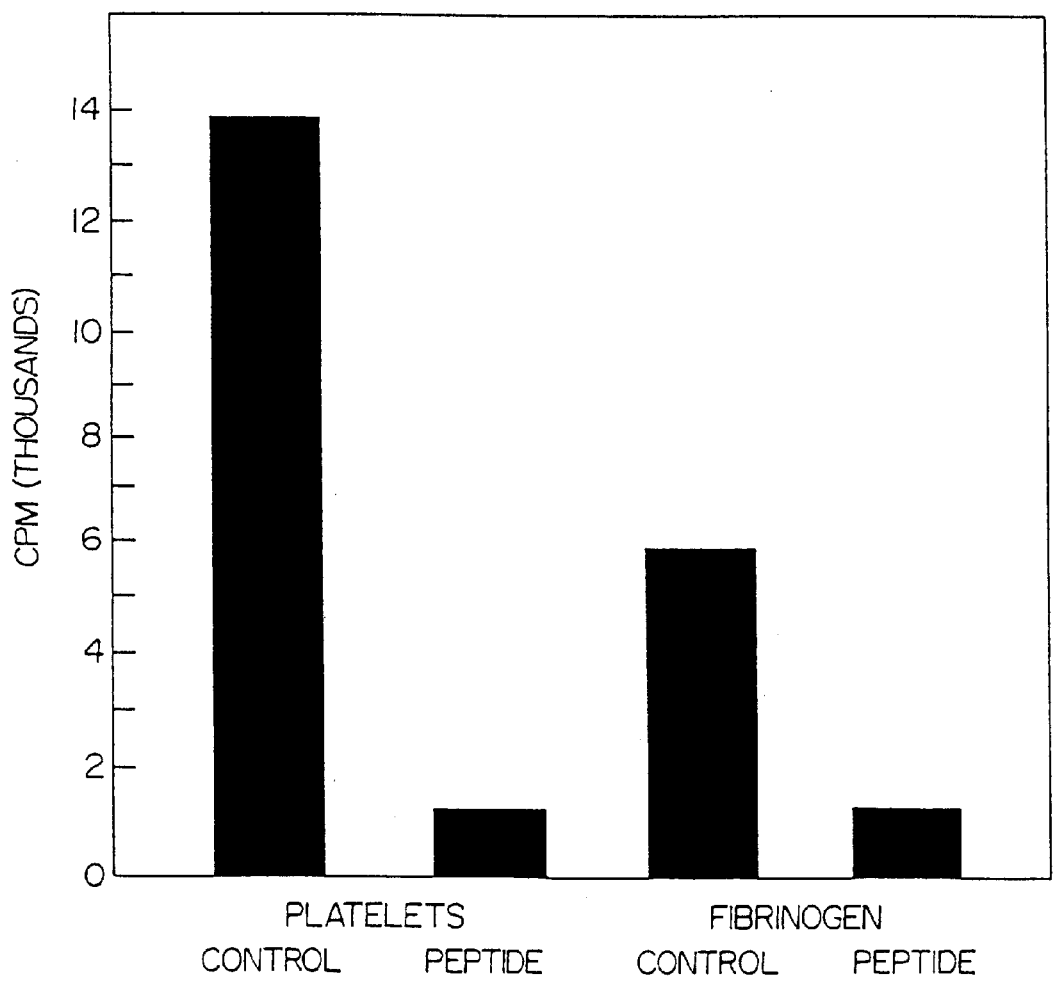
FIG. 6 shows the platelet and fibrinogen uptake by Gore-Tex grafts in animal 1 injected with the peptide of Example VIII.
Figure 7:
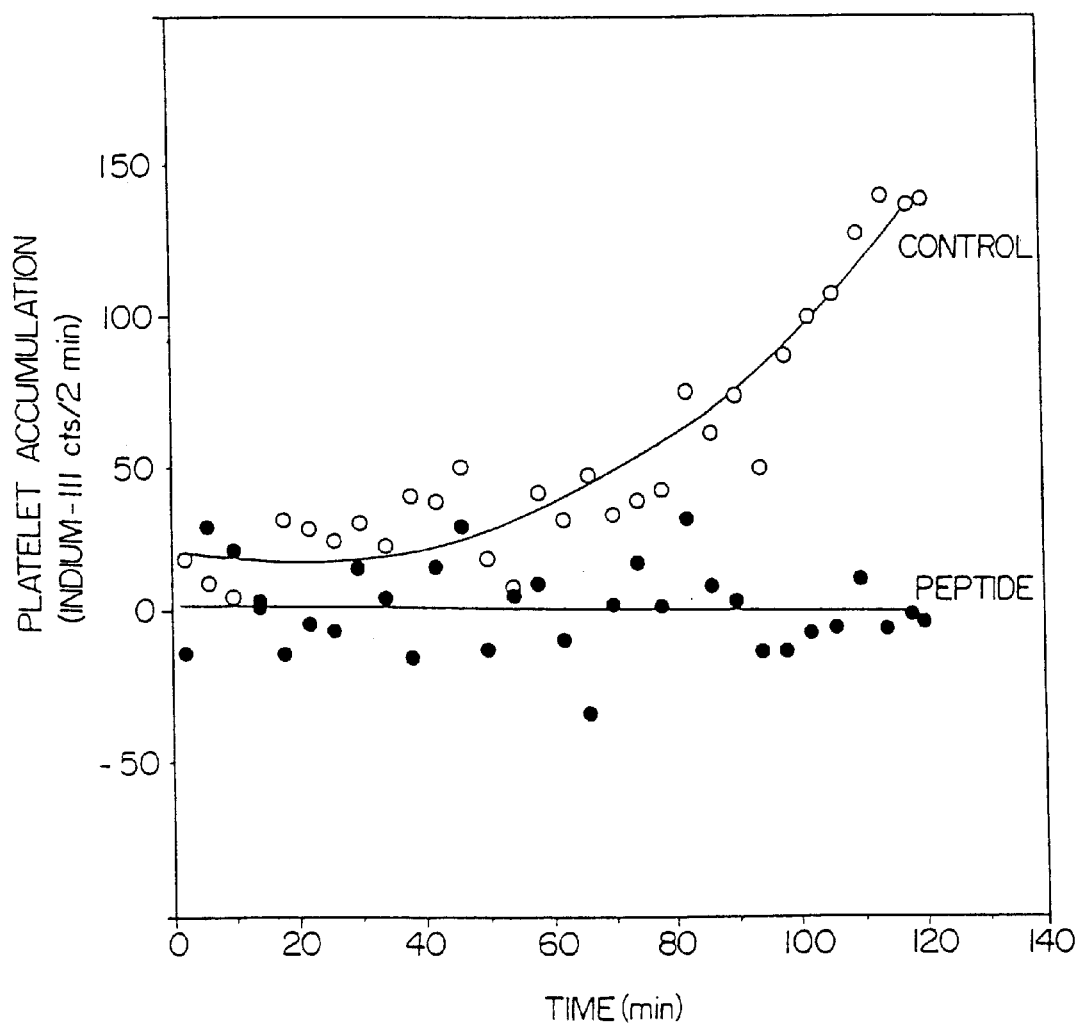
FIG. 7 shows the platelet uptake rates by Gore-Tex grafts in animal 1 injected with the peptide of Example VIII.

In the first of these animals, the peptide was administered as two bolus IV injections of 10 mg/kg (160 mg per injection). The first injection was given fifteen minutes before the establishment of the second shunt and the second injection was administered one hour afterward. As shown in FIG. 6, these injections caused a significant reduction in both $^{111}$In-platelet and $^{131}$I-fibrinogen uptakes (90% and 79%, respectively). This inhibitory effect is also apparent from a plot of platelet uptake rates in peptide-treated and untreated grafts over the entire time course of the studies (FIG. 7). Here, the rate of $^{111}$In-labelled platelet accumulation represents the counts observed in a graft piece minus those found in a background section of tubing at each time point when a scan was performed.

As shown in FIG. 8, peptide treatment did not lower template bleeding and clotting times. In blood samples taken immediately after completion of the second shunt, white blood cell and platelet counts, however, were reduced by 37% and 14%, respectively. Other parameters were unaffected.

Figure 9:
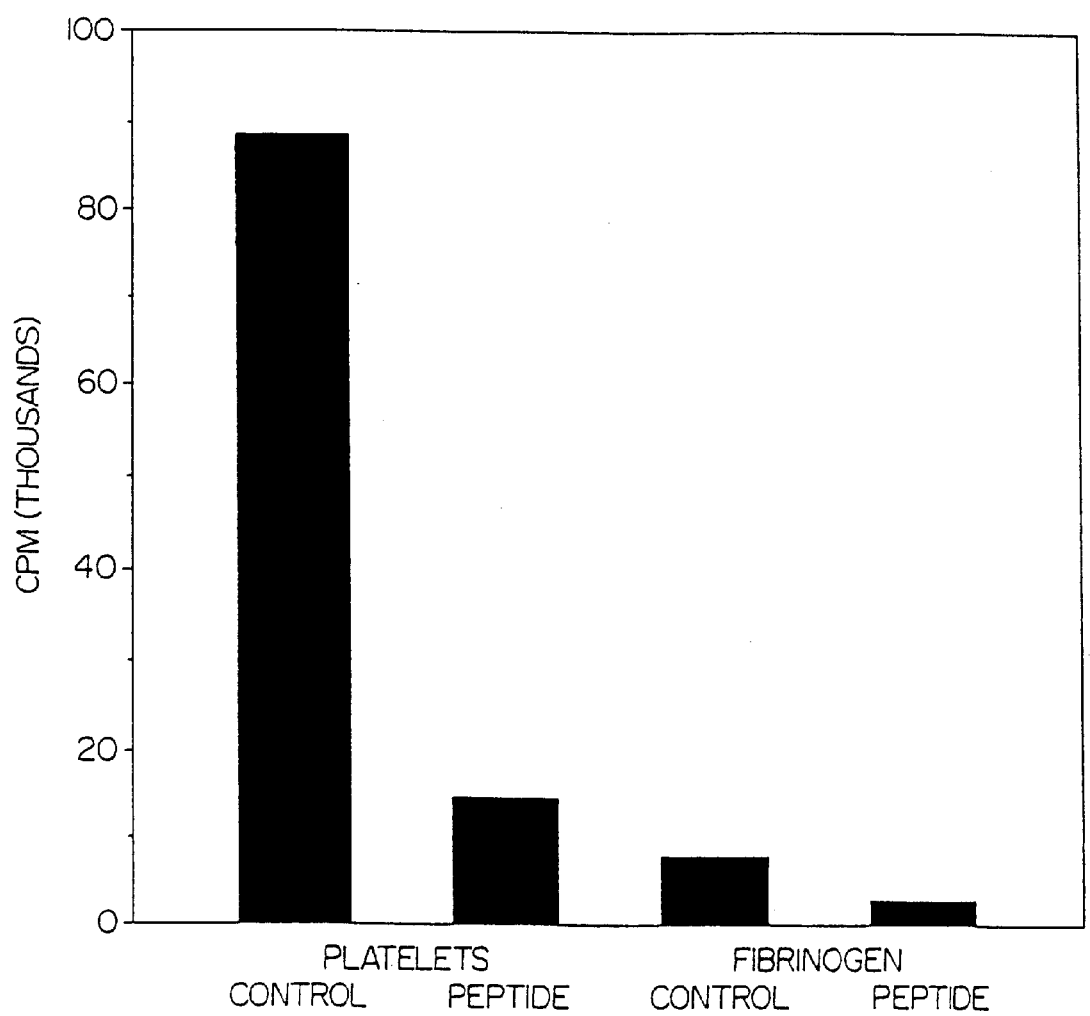
FIG. 9 shows the platelet and fibrinogen uptake by Gore-Tex grafts in animal 2 injected with the peptide of Example VIII.
Figure 10:
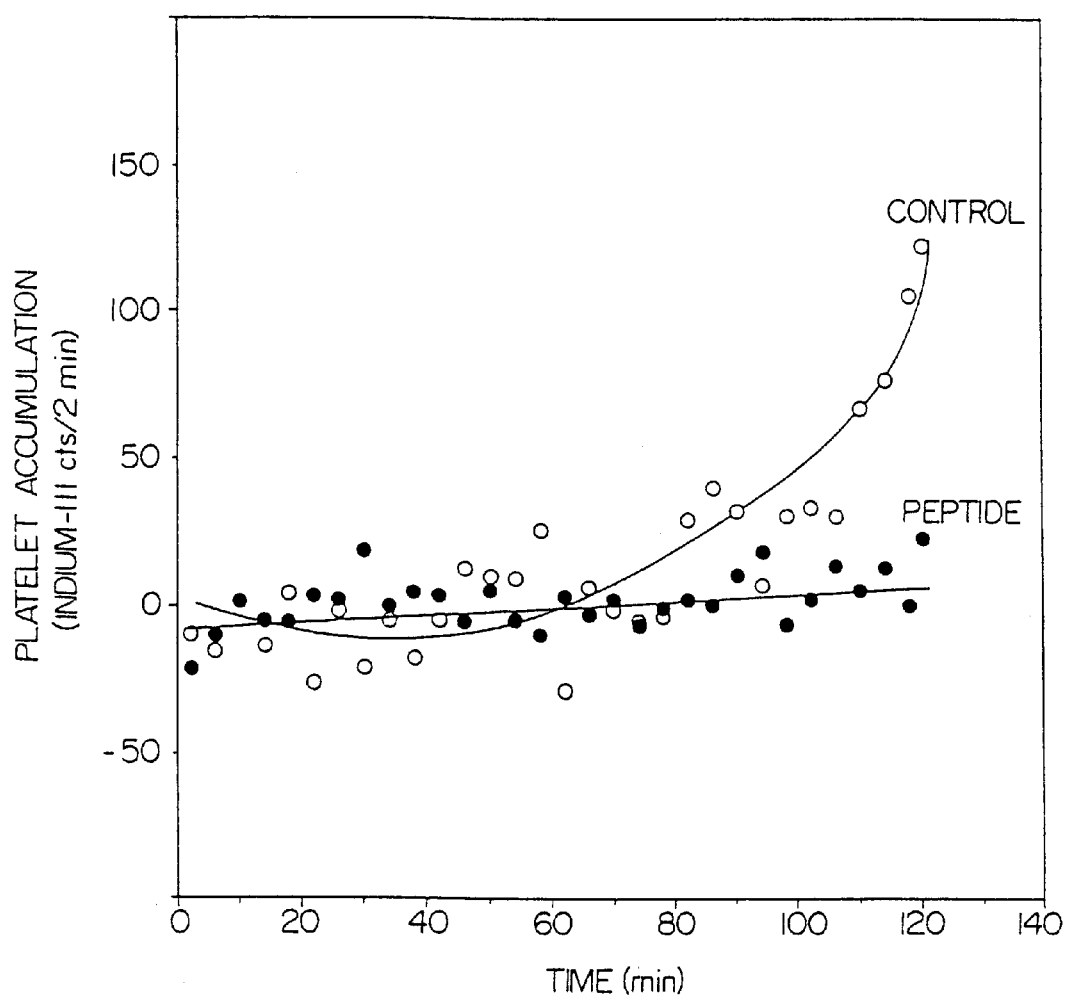
FIG. 10 shows the platelet uptake rates by Gore-Tex grafts in animal 2 injected with the peptide of Example VIII.

For the second animal, a 10 mg/kg bolus (250 mg) of the peptide was again given IV fifteen minutes before the initiation of the second shunt. This was immediately followed by a continuous infusion of 10 mg/kg/hr that lasted for the entire two hours of the shunt (500 mg total). As shown in FIG. 9, this treatment also caused significant reductions in labelled platelet and labelled fibrinogen uptakes (84% and 78%, respectively). Platelet uptake rates were again plotted in the presence and absence of the peptide (FIG. 10).

In addition, platelet aggregation studies were conducted on PRP derived from the second animal. Whole blood was drawn at three time points (0, 1 and 2 hours) of both control and experimental shunts. Platelets were completely unresponsive to the peptide treatment at a maximally effective concentration of ADP (10 μm). The peptide treatment also had no effect on template bleeding time, clotting time, or on all blood cell counts (FIG. 11).

EXAMPLE IX

Bleeding Time and Ex Vivo Platelet Aggregation Rabbit Model

1. Animal Preparation and Blood Sampling

Unanesthetized male New Zealand White rabbits (2.5–3.5 kg) were placed in a standard rabbit restrainer. Ears were shaved and a 20G teflon catheter with flowswitch (Viggo) was placed in the medial artery, flushed with saline and locked with 1 ml of heparinized saline (10 m/ml). A 22G catheter (Abbott) fitted with an injection cap (Medex) was placed in the marginal vein of the same ear. Saline or a GP $II_bIII_a$ receptor antagonist, at a concentration of 1 to 3 mg/ml, was infused via the venous catheter. At time 0, 41% of the dose was given as a bolus over 2 minutes. The remainder was continuously infused over the following 60 minutes. Blood samples (3.2 ml) were collected into syringes without needles via the arterial catheter at –10, –5, 10, 45 and 60 minutes. The first 0.5 ml was discarded and the following 2.7 ml was collected directly into a syringe containing 0.3 ml of 3.8% sodium citrate. The sample was divided into 1.5 ml aliquots and centrifuged at room temperature for 5 seconds at 12,000 G. The resulting platelet rich plasma (PRP) is used to measure ex-vivo platelet aggregation (XPA). At –10 and 60 minutes an additional 1.5 ml sample is drawn for an automated blood count (Baker Instruments). Catheters are flushed and locked after every sample.

2. Ex-Vivo Platelet Aggregation 300 ml of PRP was placed in a disposable glass cuvette with a stir bar. The cuvette was placed in the temperature regulated light path of a light transmittance aggregometer (Chrono-log) and equilibrated to a 37° C. Baseline transmittance was recorded for 30 seconds, after which 10 ml of ADP (1 mM) was added and the change in transmittance recorded. The maximum change from baseline (dT) was noted for each sample. The extent of inhibition of XPA that was produced by an inhibitor was calculated for each animal as follows: Mean dTs were calculated for the pre and post infusion values, and then, percent inhibition was calculated as (1–dt(post)/ddt(pre))×100.

3. Cutaneous Bleeding Times (CBT)

CBT was measured at –10, –5, 10, and 45 minutes on the opposite ear, using an automated incision-making instrument (Surgicutt®, ITD). An incision (5 mm×1 mm deep) was made on the dorsal surface of the ear at sites not supplied by major blood vessels. Blood was blotted away with absorbent paper placed near the incision site, every 2 to 15 seconds, to a maximum of 15 minutes. Cessation of bleeding was defined as no blood forming at the incision site for 15 seconds. The range of duplicate CBT in 40 normal rabbits was 0.88 to 3.38 minutes.

4. Peripheral Blood Flow (PBF)

For the experiments summarized in Table I, PBF was monitored by observation of the condition of the blood vessels in the rabbits' ears, prior to and during the infusion. Normal flow was defined as ears that appeared pink to red, with no visible constriction of the major blood vessels. Decreased flow applied to ears that have constricted vessels resulting in cold, pallid ears for up to 40 minutes following the start of the inhibitor infusion.

In an alternative series of experiments, (Table 2) PBF was measured quantitatively with a laser dopler flow probe (Perimed). The probe was positioned securely over the vascular bed of one ear and flow monitored continuously. Each inhibitor was infused and CBT measured in the opposing ear. No arterial catheter was placed for blood sampling, consequently XPA was measured in these animals. However, the doses used were shown in previous experiments to effectively inhibit XPA.

5. Results

CBT, XPA, and observed PBF were summarized in FIG. 12. The ratio of the post to pre treatment CBT was calculated for each animal by dividing the mean of the 2 post-treatment (and during infusion) samples by the mean of the pre samples. In two saline control rabbits the mean±sd ration of post treatment CBT (n=10) to a mean pre-treatment CBT was 1.12±0.19.

The experiments measuring PBF by laser doper probe are summarized in Table III. As positive control, epinephrine was infused intravenously (1 mg over 2 minutes) at 60 minutes. The resulting vasoconstriction reduced flow to near 0 flow units within 5 minutes.

The doses listed in FIG. 12 and in Table III refer to the bolus portion only. There were no significant changes in any of the blood indices measured.

described in Example VII to measure bleeding, four additional peptides were tested. These peptides included 11J, 11Q, 11K and 11V. Results are shown in Table IV. While all four peptides inhibited ex vivo platelet aggregation at the doses indicated, peptides 11J, 11K and 11V cause extensive prolongation of bleeding time, 11Q, in contrast, did not affect bleeding time. These results corroborated that it is the presence of a positive charge in the +4 position, as possessed by 11Q, which on platelet aggregation inhibiting peptides confers the characteristic of not prolonging bleeding time.

TABLE IV

| Code | Dose | ex vivo inhibition platelet aggregation (%) | Pre dose bleeding time (min.) | Post dose bleeding time (min.) |
|---|---|---|---|---|
| 11J | 5 Mg/Kg bolus; 120 µg/Kg/min. infusion | >98 | 2.1 | >30 |
| 11K | 6.8 Mg/Kg bolus; 163 µg/Kg/min. infusion | >98 | 2.1 | >30 |
| 11V | 8.5 Mg/Kg bolus | >98 | 2.0 | 21 |
| 11Q | 1.1 Mg/Kg bolus; 28.5 µg/Kg/min. infusion | >95 | 2.1 | 3.5 |

TABLE III

| Drug | Time (min.) | CBT (min.) | PBF (units) |
|---|---|---|---|
| R(Pen)GHRGDWRCR | 0 | 2.8 | 282 |
| 3.75 mg/kg | 10 | 1.5 | 9 |
| | 45 | ND | ND |
| R(Pmc)GHRGD(Y—OMe)RCR | 0 | 2.9 | 392 |
| 1.5 mg/kg | 10 | 0.8 | 5 |
| | 45 | 1.5 | 360 |
| R(Pmc)GHRGD(Y—OMe)RCR | 0 | 2.1 | 318 |
| 1.5 mg/kg | 10 | 3.8 | 0 |
| | 45 | 1.2 | 283 |
| AcCNPRGDY—OMeRCNH$_2$ | 0 | 1.8 | 263 |
| 4.5 mg/kg | 10 | 2.2 | 317 |
| | 45 | 3.0 | 293 |

Although the second and third peptides listed in Table III are identified by the same sequence, they differ by the isomeric form of Pmc, which can be in either the D or C configuration. The two forms were separated and individually tested, although the identify of the form was not determined.

EXAMPLE X

Additional Results

Using the method described in Example V to measure ex vivo inhibition of platelet aggregation and the method

TABLE V

Inhibition of Platelet Aggregation
(SEQ ID NOS. 134–139, respectively)

| Code | Formula | IC$_{50}$ (µM) |
|---|---|---|
| 11Z | AcCSPRGD(TyrOMe)RC—NH$_2$ | 0.45 |
| 12A | AcCAPRGD(TyrOMe)RC—NH$_2$ | 0.41 |
| 12B | AcCLPRGD(TyrOMe)RC—NH$_2$ | 0.28 |
| 12C | AcCDPRGD(TyrOMe)RC—NH$_2$ | 3.0 |
| 12D | AcCYPRGD(TyrOMe)RC—NH$_2$ | 0.22 |
| 12E | AcCRPRGD(TyrOMe)RC—NH$_2$ | 0.34 |

As can be seen from the data in Table V, the residue lying two positions to the amino side of the RGD binding site is preferably non-acidic residue.

EXAMPLE XI

A. Synthesis of Cyclic Peptides with Disulfide Bridges

Peptide syntheses were performed by the solid-phase method (Steward, J. M. and Young, J. D., Solid Phases Peptide Synthesis, 2nd ed.; Pierce Chemical Co., Rockford, Ill., 1984), incorporated herein by reference, utilizing an automated synthesizer (Applied Biosystems, Inc. Model 431A). Carboxamide peptides were synthesized with p-methylbenzhydrylamine (pMBHA) resin and peptides with C-terminal acids were synthesized with chloromethylated resin. N-terminal tert-butyloxycarbonyl protection was employed for all amino acids. Boc-Arg(Tos)-OH, Boc-Asp(OcHx)-OH, Boc-Cys(4-MeBzl)-OH, Boc-Gly-OH, Boc-Hpa-OH, Boc-Lys(CZ)-OH, Boc-Pen(4-MeBzl)-OH, Boc-DPen(4-MeBzl)-OH, Boc-Pro-OH, and Boc-Tyr(Me)-OH were obtained from Bachem Inc. (Torrance, Calif.). Pmp(4-MeBzl)-OH and Boc-Tyr(n-Butyl)-OH were synthesized according to the procedures of Yim, C. F. N. and Huffman, W. F. *Int.J. Peptide Protein Res.* (1983) 21:568, and Solar, S. L. and Schumaker, R. *J. Org. Chem.*, (1966) 31:1996, respectively. Dicyclohexylcarbodiimide and hydroxybenzyltriazole were used in the coupling reactions, which were monitored by the ninhydrin test.

For the preparation of peptides with N-terminal acetyl, the peptides were acetylated using a mixture of acetic anhydride (20 eq.) and diisopropylethylamine (20 eq.) in N-methyl pyrrolidone.

The peptides were removed from resin and deprotected with anhydrous hydrogen fluoride (HF; 10 mL/g of resin-bound peptide) containing anisole (1 mL/g) at 0° C. for 60 minutes. After the evaporation of HF, the residue was washed with anhydrous ether, and the crude peptides were extracted with water or 15% aqueous acetic acid. The aqueous fractions were combined and lyophilized.

The crude acyclic peptide was dissolved in 0.1 M ammonium bicarbonate (0.5 mg/mL) and stirred open to the air. The course of the reaction was monitored via HPLC. After cyclization was complete (several hours to several days), the solution was filtered and purified via preparative RP-HPLC on a $C_{18}$ silica gel column Waters Delta-Pak, 15 $\mu$m, 300A, 47×300 mm. Elution was with a linear acetonitrile gradient (0–40%) with a constant concentration of trifluoroacetic acid (0.1%, v/v) over 20 minutes at a flow rate of 40 mL/min.

The purified peptides were analyzed by analytical reversed-phase HPLC on C-18 Columns (Vydac, 5 $\mu$m, 300A, 4.5×250 mm). The purified peptides, recovered by lyophilization of the HPLC fractions, were at least 98% pure. The solvent system used for analytical HPLC was a binary system, water containing 0.1% TFA and acetonitrile containing 0.1% TFA as the organic modifier, and the solvent programs involved linear gradients as follows: (1) 0% to 40% acetonitrile over 15 min. with flow rate of 1.5 mL/min.; (2) 0% to 50% acetonitrile over 15 min. with flow rate of 1.5 mL/min.; (3) 0% to 60% acetonitrile over 15 min. with flow rate of 1.5 mL/min.

All peptides were characterized by FAB (Fast Atom Bombardment) mass spectroscopy and amino acid analysis (AAA). FAB mass spectroscopy was performed at Mass Spectrometry Service Laboratory, Department of Chemistry, University of Minnesota. Amino acid analysis was performed on a Pickering Labs-Trione amino acid analyzer, equipped with spectra-physics UV detector. Hydrolysis of peptide samples for AAA was carried out on 1-mg samples with 6N constant-boiling HCl (1 mL), which were degassed and sealed under vacuum and then heated for 24 h at 110° C.

B. Synthesis of Cyclic Peptides with Lactam Bridges

Figure 13:
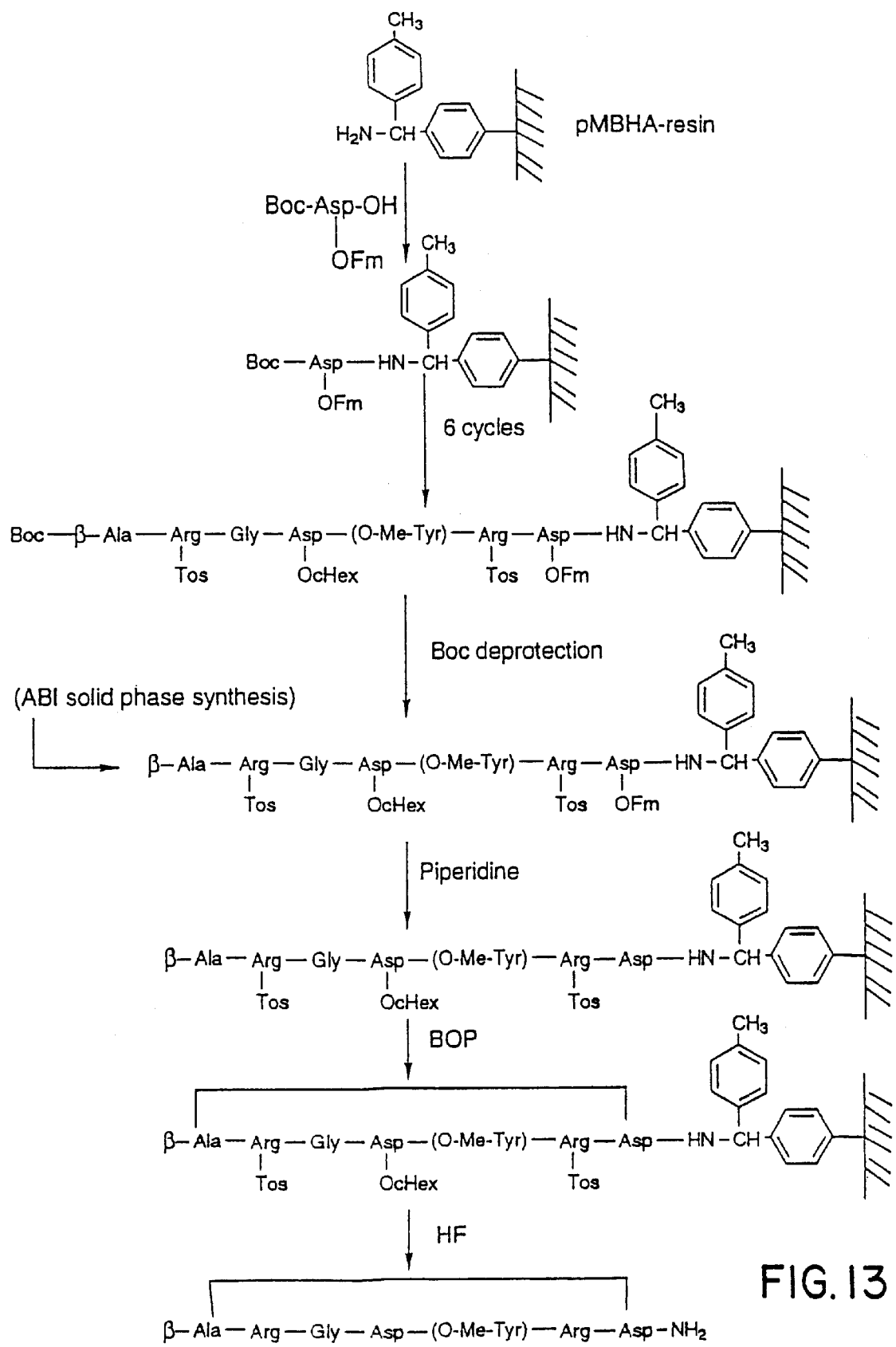
FIG. 13 shows the synthesis of one representative cyclic lactam analogue.

The cyclic lactam analogues were synthesized as outlined in FIG. 13. The protected peptide resin was synthesized with p-methylbenzhydrylamine (PMBHA) resin. The formation of the lactam on the resin was by the methodology introduced by Felix and co-workers. Felix, et al. *Int. J. Peptide Protein Res.* (1988) 31:231; Felix, A. F. et al. *Int. Int. J. Peptide Protein Res.* (1988) 32:441. This methodology uses $N^{\alpha}$-Boc-amino acids together with OFm side-chain protection for Asp and Glu. Asp and Glu were introduced with Boc-Asp(OFm)-OH and Boc-Glu(OFm)-OH. After coupling the last amino acid, the OFm protecting groups were selectively removed by treating the peptide resin in 50% piperidine in DMF (Dimethylformamide) for 1 h. The peptide resin was washed with DMF (3×40 mL), DCM (dicholoromethane) (3×40 mL), suspended in 15 mL of DMF, and mixed with a 6-fold excess of BOP reagent in the presence of an 8-fold excess of diisopropylamine (DIEA) for 5 h. The coupling was repeated until the resin gave the negative ninhydrin test.

After the cyclization, the peptides were removed from resin and deprotected with anhydrous Hydrogen fluoride (HF; 10 mL/g of resin-bound peptide) containing anisole (1 mL/g) at 0° C. for 60 minutes. After the evaporation of HF, the residue was washed with anhydrous ether, and the crude peptides were extracted with water or 15% aqueous acetic acid. The aqueous fractions were combined and lyophilized.

The crude peptides were purified via preparative RP-HPLC on a $C_{18}$ silica gel column (Waters Delta-Pak, 15 $\mu$m, 300A, 47×300 mm) eluting with a linear acetonitrile gradient (0–40%) with a constant concentration of trifluoroacetic acid (0.1%, v/v) over 20 minutes at a flow rate of 40 mL/min.

The purified peptides were analyzed by analytical reversed-phase HPLC on C-18 Columns (Vydac, 5 $\mu$m, 300A, 4.5×250 mm). The solvent system used for analytical HPLC was a binary system, water containing 0.1% TFA and acetonitrile containing 0.1% TFA as the organic modifier, and the solvent programs involved linear gradients as follows: (1) 0% to 40% acetonitrile over 15 min. with flow rate of 1.5 mL/min.; (2) 0% to 50% acetonitrile over 15 min. with flow rate of 1.5 mL/min.; (3) 0% to 60% acetonitrile over 15 min. with flow rate of 1.5 mL/min.

All peptides were characterized by FAB (Fast Atom Bombardment) mass spectroscopy and amino acid analysis. FAB mass spectroscopy was performed at Mass Spectrometry Service Laboratory, Department of Chemistry, University of Minnesota. Amino acid analysis was performed on Pickering Labs-Trione amino acid analyzer, equipped with spectra-physics UV detector. Hydrolysis of peptide samples for AAA was carried out on 1-mg samples with 6N constant-boiling HCl (1 mL), which were degassed and sealed under vacuum and then heated for 24 h at 110° C.

C. Receptor and Ligand Purifications

Receptors were purified according to the procedures of Pytela et al. (Methods Enzymol. 144:475 (1987), incorporated herein by reference. Briefly, vitronectin receptor (VnR) was purified by RGD peptide-affinity chromatography from (100 mM) octyl glucoside (OG) extracted human placenta. After extraction, the suspension was adsorbed to a Sepharose CL4B column and then applied to a GRGDSPK affinity column. Except where stated, all procedures were carried out at 4° C. The peptide column was washed with five volumes of Tris-buffered saline (TBS) containing 3 mM $CaCl_2$ and 50 mM OG and then with five column volumes of room temperature TBS containing 3 mM $CaCl_2$ and 50 mM OG. Elution of bound receptor was achieved at room temperature with TBS containing 10 mM EDTA and 50 mM OG. Finally, 12 mM $Ca^{2+}$ was added to eluted fractions. The fractions were evaluated by 8% SDS-PAGE (non-reduced) and fractions exhibiting bands indicative of 150, 145 and 90 KDa MW were pooled and dialyzed into Tris buffered saline (TBS) pH 7.5 containing 50 mM OG and 3 mM $CaCl_2$, then concentrated on an amicom YM 30 filter.

The VnR preparation described above comprises both avB3 and avB5 integrin. For the ELISA assay described in Section F below, it is an alternative to have a purified avB5 VnR preparation. The avB5 VnR is prepared as described above, with the following modifications. Affinity chromatography was with vitronectin polypeptide instead of GRGDSPK (SEQ ID NO. 140) affinity column. The wash was as before, but elution was with TBS, 50 mM OG, and 0.1 mg/ml GRGDSP. The eluted fractions were evaluated by SDS as described, then pooled, dialyzed, and concentrated.

Fibronectin receptor (FnR) was similarly purified from (100 mM) octyl glucoside-extracted human placenta using a procedure identical to that for the VnR up to and including the initial Sepharose chromatography step. The Sepharose CL4B column flow-through was brought to 3 mM $Mn^{2+}$ and the resulting solution was run over a 110 Kd fibronectin fragment-affinity column (Pytela supra). Washing and elution steps were the same as those used in purifying vitronectin receptor, with the exception of the use of $MnCl_2$ rather than $CaCl_2$ in the wash buffer. The fractions were evaluated by 8% SDS-PAGE (non-reduced) and fractions exhibiting bands indicative of 155 and 110 KDa MW were pooled and dialzyed into TBS pH 7.5 containing 50 mM OG and 3 mM MnCl$_2$, then concentrated on an amicron YM 30 filter.

Platelet glycoprotein IIb/IIIa was purified from outdated human platelets. Briefly, the platelets were centrifuged for ten minutes at 800×g to pellet RBC's. The platelets were then washed three times with 20 mM tris-HCl, 150 mM NaCl (TBS), 1 mM EDTA, 0.2% glucose, pH 7.5, and centrifuged at 1500×g to pellet cells. Cells were lysed in two pellet volumes of TBS, 100 mM OG, 1 mM MnCl$_2$, 1 mM MgCl$_2$ and 0.1 mM PMSF, followed by centrifugation at 30,000×g. The supernatant fraction was collected and loaded onto a Sepharose 2B column, previously equilibrated in TBS, 1 mM MnCl$_2$, 1 mM MgCl$_2$, 0.1 mM PMSF, 0.1 mM OG. Flow-through from Sepharose 2B column was collected and passed over a RGD-peptide (GRGDSPK) affinity column. The peptide column was eluted with TBS, 50 mM OG, and one mg per ml GRGDSP. The fractions were collected, evaluated by 8% SDS-PAGE (non-reduced) and fractions exhibiting bands indicative of 145 and 90 KDa were pooled, dialyzed into TBS pH 7.5 containing 3 mM OG, 1 mM MgCl$_2$ and 1 mM MnCl$_2$ and concentrated on an Amicon YM 30 filter.

D. Fibronectin Receptor (FnR) ELISA Assay

Peptide binding to purified FnR was determined by using a competitive enzyme-linked immunosorbent assay (ELISA) in which fibronectin is immobilized and the binding of solubilized FnR, in the presence of various concentrations of peptide analogue, is detected with a polyclonal anti-FnR antibody, followed by a labelled anti-rabbit IgG conjugate.

Microtiter plates were coated overnight at room temperature with 110 μL of human fibronectin purified according to the method of Ruoslahti and Engvall, *Intl. J. Canc.* 20:1–5 (1977), which is incorporated herein by reference (at 2 μg/mL) in TBS. The plates were washed three times with TBS that contained 0.05% Tween-20. 50 μL of receptor in TBS containing 20 mM octylglucoside and 2 mM MnCl$_2$ were added to each well. 50 μL of peptide in the same buffer were then added in 10-fold serial dilutions. The plates were incubated for three hours at room temperature, washed with 200 μL of the above TBS-Tween buffer. 100 μL of affinity-purified rabbit anti-human fibronectin receptor antibody were added to the wells and the plates were incubated for an additional two hours, washed twice with TBS-Tween and then distilled water. Affinity-purified goat anti-rabbit IgG conjugated to horseradish peroxidase (100 μL) was then added to each well and incubated overnight at room temperature. The following day, the plates were washed with TBS-Tween and then distilled water. 100 μL of substrate mixture (10 mg O-phenylenediamine in 25 mL 0.1 M citrate-phosphate buffer, pH 5.0, plus six microliters of 30% H$_2$O$_2$) were added to the plates and allowed to develop in the dark. The development process was stopped by adding 50 μL of 4N H$_2$SO$_4$ to each well.

Results are shown in FIGS. 15 and 16.

E. IIb/IIIa-Fibrinogen ELISA

Microtiter plates were coated overnight at room temperature with 110 μL of human fibrinogen (at 10 μg/mL) diluted in TBS. The plates were then washed three times with 200 μL per well of TBS+0.05% Tween-20. Fifty (50) μL of purified IIb/IIIa diluted in TBS with 20 mM octylglucoside, 2 mM MgCl$_2$ and 2 mM CaCl$_2$ were added to the wells. Fifty (50) μLs of peptide in the same buffer were then added in 10-fold serial dilutions and the plates were incubated for three hours at room temperature. The plates were washed three times with TBS-Tween and 100 μL of rabbit anti-IIb/IIIa were added to each well. After a two hour room temperature incubation, the plates were washed and the remaining steps done as described for the FnR ELISA.

Results are shown in FIGS. 15 and 16.

F. Vitronectin Receptor (VnR) ELISA

Purified human vitronectin purified according to the method of Yatohgo et al., *Cell Struct. Funct.* 13:281–292 (1988) was diluted to 10 mg/mL in 0.1 M Carbonate buffer (pH 9.6), 110 μL were added to the wells of a microtiter plate, and the plate was incubated overnight at room temperature. The plate was washed three times with 200 μL per well of TBS-Tween at room temperature. Fifty (50) μL of purified human VnR was diluted in TBS containing 20 mM octylglucoside, 2 mM MgCl$_2$ and 2 mM CaCl$_2$. Fifty (50) μL of peptide sample, diluted in the same buffer, were then added in 10-fold serial dilutions and the plates were incubated for three hours at room temperature. The plates were washed three times with TBS-Tween and 100 μL of affinity purified rabbit anti-VnR were added to each well. The first antibody was incubated for two hours at room temperature, washed, and the procedure continued as described for the FnR ELISA.

Results are shown in FIGS. 15 and 16.

G. Platelet Aggregation Assay

Platelet aggregation was assessed using the method of Born, *Nature* 194:927–929 (1962), incorporated herein by reference. Briefly, the change in light transmission was measured through a stirred suspension of platelets in an aggregometer (Model 400 VS, Chrono-Log, Havertown, Pa., USA). Studies employing ADP were performed with platelet-rich plasma (PRP), which was obtained by low-speed centrifugation (200×g for 10 min.) of whole blood freshly drawn into trisodium citrate (at a final concentration of 11 mM). In studies using thrombin, the PRP was gel-filtered on Sepharose 2B in divalent ion-free Tyrode's solution containing 2% BSA. For all studies, the reference standard was platelet-poor plasma, which was obtained by centrifuging PRP at 1000×g for 5 min.

All aggregation studies were performed at 37° C. with a constantly stirred suspension of 3×10$^8$ platelets/mL. (Platelet count was determined with the aid of a hemacytometer.) Peptides and stimulants were added to these suspensions in 1% dilutions. The PRP and gel-filtered platelets were used within three hours from the time of blood collection.

Peptide anti-aggregation potencies were determined from dose-responsive curves for the inhibition of the maximum aggregation responses stimulated by physiologic doses of ADP (10 μM) and thrombin (2 U/mL). The 50% inhibitory concentration of each peptide (IC$_{50}$) was determined by regression analysis of these curves.

Results are shown in FIGS. 14, 15 and 16.

An alternative assay of platelet aggregation is performed as follows. Blood is drawn from a donor who has not taken any medication (including aspirin) in at least two weeks and transferred to a 50 ml tube containing either 1/10th volume of 3.8% citrate (w/v) or 5.1 U/ml heparin. The tube is gently inverted to mix and then centrifuged at 1200 rpm in a swinging bucket rotor for 15 minutes at room temperature (Sorvall RT6000B). The upper platelet rich plasma (PRP) phase is removed with a polypropylene transfer pipette and transferred to a new polypropylene tube, and gently inverted to mix. Store at room temperature.

The assay is a competitive assay based on aggregation of stirred platelets in PRP which is obtained by centrifugation of citrated or heparinized whole blood. The progress and the extent of the platelet aggregation reaction is monitored by measuring transparency of the platelet suspension in an aggregometer. The addition of increasing amounts of peptide results in an increase in inhibition of platelet aggregation and yields an inhibition curve from which can be determined an $IC_{50}$ which denotes the concentration of peptide necessary to inhibit 50% of the control platelet aggregation response (without peptide).

The assay is conducted as follows. 0.6 mL of platelet rich plasma (PRP) were removed and placed in a 1.5 ml Eppendorf tube, along with a 0.6 mL $H_2O$ blank, and was centrifuged in an Eppendorf micro-centrifuge at 14,000×g for four minutes at room temperature. After centrifugation, 0.5 ml of supernatant [or platelet poor plasma (PPP)] was removed with a pipet and placed in an aggregometer tube. The tube was put in the PPP slot of the aggregometer where it served as a blank for PRP. This blank remained during the entire time of the assay. The platelet concentration was determined in PRP with a cell counter and diluted with homologous PPP to obtain 300,000 platelet/µL. 0.5 mL of PRP (300,000 platelets/µL) were removed with a pipette and placed in an aggregometer tube with a stir bar. The tube was incubated in the incubation slot at 37° C. without stirring for 5 minutes. The tube was then transferred to the PRP slot and the sample was stirred for 5 to 10 seconds at 1,200 rpm at 37° C. for baseline adjustment.

Aggregation reaction was initiated with 5 µL of 1 mM ADP stock solution to obtain final concentration of approximately 10 µM ADP. The aggregation reaction was recorded for two minutes to obtain the platelet aggregation control response (without the peptide). The platelet aggregation control reaction was repeated two more times and the average of three control aggregation reactions were determined. The aggregation response was measured in 2 mm units from baseline (before ADP addition) to respond at two minutes from the time of ADP addition or maximal response (if before 2 min), whichever was larger.

The inhibitory activity of the peptide was determined in platelet aggregation assay. The desired amount of the peptide (1 to 10 µL) was added to 0.5 ml PRP previously incubated for 5 min in the aggregometer. 5 µL of 1 mM ADP was added to initiate the aggregation reaction. The reaction was monitored for two minutes. This procedure was repeated with five different concentrations of the peptide (final concentrations 0.1 µM to 0.3 µM for citrated PRP and 1.8 µM to 3 µM for heparinized PRP) to obtain aggregation responses ranging between 30 to 70% of control. The aggregation response was determined in 2 mm units. The platelet aggregation control reactions were repeated to determine the average control response in 2 mm units. The mean value of all control aggregation reactions was determined. After the aggregation reaction, the stir bar was removed with a magnet, washed in ethanol and rinsed with distilled water.

EXAMPLE XII

Selectivity and Potency of Peptides Differing by Single Substitutions

The peptides described in this Example were synthesized according to the methods of Examples I and XI. Selectivity and potency were measured according to the methods of Examples II through XI. The peptide identification numbers used in this Example are consistent and relevant to this Example only. Some of the peptides are identified by other nomenclature elsewhere in this document.

A. Effects of Pen Substitutions

To investigate the effect on $\alpha_{IIb}\beta_3$ potency and selectivity of altering the chirality at the amino-terminal L-Pen in the prototype peptide 1 (G(Pen)GHRGDLRCA), the D-Pen-containing analogue 2 (G(D-Pen)GHRGDLRCA) was synthesized. Data is presented in FIG. 17. Analogue 2 was approximately 2-fold more potent than the L-Pen-containing analogue 1 in the $\alpha_{IIb}\beta_3$ assay. The Pen residue with D configuration at the amino-terminus had no significant effect on the selectivity. The situation is similar for analogues 3 (R(Pen)GHRGDLRCR) (SEQ ID NO. 141) and 4 (R(D-Pen)GHRGDLRCR) (SEQ ID NO. 142). The D-Pen-containing analogue 4 was 2-fold more potent in the aggregation assay than the L-Pen-containing analogue 3. The effects of additional conformational constraint in the side chains of the amino-terminal Pen were evaluated by evaluating amino-terminal Pmp, as described in Yim et al., *Int. J. Peptide Protein Res.* 21:568–570 (1983), incorporated herein by reference, and Pmc residues, as described in Stanfield et al., *Syn. Comm.* 18:531–543 (1988) and Yim et al., *J. Org. Chem.* 53:4605–4607 (1988), each incorporated herein by reference. Both contain the more lipophilic and conformationally restricting β,β-cyclopentamethylene at the β-carbon atom of the side chain. These residues have previously been used to further restrict the conformational freedom of other disulfide-bridged peptides leading to highly constrained ring systems, Hruby, V. J., *Epilepsia* 30 (Suppl. 1):S42–S50 (1989). Analogue 5, R(Pmc)GHRGDRCR (SEQ ID NO. 143), which contains D,L-Pmc at position −3, was prepared by employing BOC-D,L-PmC(4-MeBzl). Analogue 5 was found to be 3-fold more potent than analogue 3 in the aggregation assay. On the other hand, the substitution of Pen with an amino-terminal Pmp group in analogue 6 (Pmp) GHRGDLRCA, resulted in a 2-fold increase in potency over analogue 1. The structure of this analogue shows that an exocyclic residue at the amino-terminus is not necessary for potency. The Tmc residue, which contains β,β-cyclotetramethylene at the β-carbon atom of the side chain, was evaluated as a substitution for the amino-terminal Pen residue. Analogue 7 (R(Tmc)GHRGDLRCR (SEQ ID NO. 144)), which contains D,L-Tmc at position −3, was prepared by employing Boc-D,L-Tmc(4-MeBzl). The mixture of diasteromers was 2-fold more potent than analogue 3 in the platelet aggregation assay.

This series of analogues demonstrated that the substitution of Pmc for Pen is effective in obtaining more potent analogues. Altering the chirality at the amino terminal Pen residue had only a modest effect on the selectivity.

B. Effects of Substitutions at Position 3

A subsequent series of analogues was prepared based on the sequence of the potent and selective analogue 5, R(Pmc) GHRGDLRCR (SEQ ID NO. 145). Data is presented in FIG. 18. The effect of increased hydrophobicity at position 3 of analogue 5 was investigated by the incorporation of a series of hydrophobic amino acids at this position. It was found that the substitution of aromatic hydrophobic residues Phe and Tyr (analogues 9 and 10, respectively) for Leu is very effective in obtaining more potent analogues. For example, the substitution of Leu with Phe resulted in about a 5-fold increase in platelet aggregation potency in analogue 9. The effect of para substitution of the aromatic ring in the Phe residue was investigated by the substitution of Phe with p-I-Phe and p-Cl-Phe. These two analogues (12 and 13) exhibited similar platelet aggregation potencies as analogue 9. The similar potency of these analogues implied that the aromatic nucleus of the Phe residue interacts with a region of $\alpha_{IIb}\beta_3$ that is capable of accepting a range of electronegativities. The study was expanded to include the following additional hydrophobic residues at position 3: O—Me—Tyr, O-n-butyl-Tyr (Solar et al., *J. Org. Chem.*

31:1966–1997 (1966), incorporated herein by reference), Phg, Hpa and 2-Nal. These analogues (11, 14, 15, 16, and 17) also exhibited similar platelet aggregation potencies as analogue 9. Analogue 14 was the most potent analogue of this series with respect to inhibition of platelet aggregation. It contains one of the most hydrophobic aromatic side chains in this series.

The high potency of these analogues implied that these hydrophobic residues interact with a region of $\alpha_{IIb}\beta_3$ that is capable of accepting a range of molecular volumes. Surprisingly, the substitution of Leu with a shorter aliphatic residue (Val), analogue 8, also resulted in a 4-fold increase in potency. This shows that the contribution of the β-methyl group of valine may be as significant as the aromatic group for the interaction with the hydrophobic region of $\alpha_{IIb}\beta_3$.

C. Effects of Substitutions in Position -2

The effect of the substitution of the Gly residue at position -2 was examined. Data is presented in FIG. 19. Single amino acid substitutions (Ser, Asp, Ile, Asn and Arg) were introduced into analogue 11, which is highly potent in platelet aggregation assay. Substitution of Ser, Ile, Asn and Arg for Gly produced analogues (19, 20, 21 and 22) with similar platelet aggregation potencies and ELISA selectivities. However, the substitution of Asp for Gly (analogue 18) led to a 4-fold decrease in potency.

D. Effects of Substitutions at Position -1

The effect of substitution for His at position -1 was examined. Data is presented in FIG. 20. Single amino acid substitutions (D-His, Tyr, D-Tyr and Pro) were introduced into analogue 11, which afforded a series of analogues (23, 24, 25 and 26). These substitutions had little influence on the platelet aggregation inhibitory potency of analogue 11. The study with peptides 23–26 suggests that His is not interacting with $\alpha_{IIb}\beta_3$ through hydrogen bonding or by other interactions characteristic of the aromatic ring. The substitution of His with Pro did not lead to a decrease in potency.

E. Effects of the Use of Pro at Position -1 in Combination with Hydrophobic Amino Acids at Position 3

It was shown in the data presented in FIG. 17 that an exocyclic Arg residue at the amino-terminus is not necessary for potency. The subsequent series of analogues were prepared based on the sequence of analogue 26, and the Arg residues at the N-terminal and C-terminal were replaced with acetyl and amide groups, respectively. Data is presented in FIG. 21. The substitution of Gly at position -2 of analogue 26 with Ile and the replacement of the Pmc residue with Cys resulted in a 3–4 fold increase in platelet aggregation potency in analogue 27, Ac-CIPRGD(Y-OMe)RC-NH$_2$, without affecting the potency in the $\alpha_5\beta_1$ and $\alpha_v\beta_5$ assays. In general, the substitution of the Ile for Gly is very effective in obtaining more potent analogues (compare FIGS. 20 and 21).

It is known that proline is a well-known means of inducing conformational constraints into peptides. The substitution of Ile with Asn at position -2 had little effect on the platelet aggregation potency. The subsequent series of analogues was based on the sequence of the potent and selective analogue 27, Ac-CIPRGD(Y-OMe)RC-NH$_2$ and analogue 32, AC-CNPRGD(Y-OMe)RC-NH$_2$. The use of Proline at position -1 in combination with hydrophobic amino acids at position 3 yields a series of highly potent and specific $\alpha_{IIb}\beta_3$ antagonists. It was found that substitution of Tyr for Tyr (OMe) resulted in a 2-fold decrease in potency. This result suggested that the O-methyl group of Tyr(OMe) is important for the interaction with the hydrophobic region of $\alpha_{IIb}\beta_3$. The most potent analogue of this series is analogue 34, with an IC$_{50}$ in platelet aggregation of 0.1 µM. This analogue is about 150 times more potent than analogue 1, and exhibits a much higher selectivity for $\alpha_{IIb}\beta_3$.

This series of analogues demonstrated that the use of Proline at position -1 in combination with hydrophobic amino acids at position 3 is very effective in obtaining highly potent analogues.

Examination of the data for all the peptides in FIGS. 17–21 reveals a generally good correlation between the order of the IC$_{50}$ values in the $\alpha_{IIb\beta3}$ ELISA assay and the order in the platelet aggregation assay.

F. Effects of Cys Substitutions on Analogue 32

The subsequent series of analogues were prepared based on the sequence of analogue 32 shown in FIG. 22. The effect of the substitution of the amino-terminal Cys residue with other β,β-dialkylcysteins and their desamino derivatives was studied. Data is presented in FIG. 22. Replacing the Cys residue with the more lipophilic and conformationally restricting Pmc and Pmp residues did not significantly alter the relative platelet aggregation potency and had no significant effect on the selectivity compared to analogue 32. The replacement of Cys by Mpr also resulted in no significant change in potency, suggesting that there is little interaction of the N-terminal acetyl group with $\alpha_{IIb}\beta_3$.

G. Effects of Arg Substitutions at Position 4 on Analogue 32

The effect of the substitution of Arg at position 4 with other amino acids was examined. Data is presented in FIG. 23. The substitution of Arg with neutral amino acids (Ala, Cit and Leu) resulted in substantial decreases in platelet aggregation potency (analogues 43, 45 and 47). Similarly, the substitution of Arg with an acidic amino acid (Glu) led to a 15-fold decrease in potency (analogue 42) while a substitution with a Lys resulted in a compound that retained 20% of the inhibitory activity (analogue 41). This suggests that there is a specific binding pocket for a basic functional group at this position. However, the introduction of D-Arg in position 4 also led to a less favorable interaction of the peptide with $\alpha_{IIb}\beta_3$, resulting in a decrease in potency (analogue 44). Therefore it is concluded that the Arg residue at position 4 interacts with the receptor in a very stereospecific manner.

This series of analogues demonstrated that the Arg residue at position 4 plays a very important role in the binding of these analogues to $\alpha_{IIb}\beta_3$. The structure-activity relationship studies suggest that the R-G-D-Ar-R (SEQ ID NO. 168) (Ar=hydrophobic residue) sequence is the pharmacophore responsible for their high $\alpha_{IIb\beta3}$ binding affinity and very high selectivity.

H. In vivo Administration

More importantly, several peptides in FIG. 23 were administered to dogs (according to the method of Example VII) at doses capable of inhibiting ex vivo platelet aggregation by >95%. The results of this study are summarized in FIG. 24.

To measure bleeding time, two small cuts were made in the forearms of animals with a template bleeding time device (Simplate-II™, Organon Technika, Durham, N.C.), and the exuded blood was absorbed onto Whatman #2 filter paper. The template bleeding time was considered to be the time after cutting at which the absorption of blood was no longer apparent. Peptide 32 was tested using the tongue to measure template bleeding time with identical results.

Concentrations of peptides are high enough to cause >95% inhibition of ex vivo platelet aggregation. The bleeding time indicated in the parentheses was measured at a five-fold higher concentration of peptide. The agonist used for ex vivo measurement of platelet aggregation was 10 µM ADP. Ex vivo platelet aggregation using 10 µg/mL collagen as agonist was also inhibited by >95% in this experiment with Peptide 32. The peptides possessing the arginine at position 4 were the only ones that did not prolong template bleeding time at these concentrations.

The positive charge of the Arg at position 4 not only contributes binding affinity to $\alpha_{IIb}\beta_3$, but appears to be the primary element that allows the separation of inhibitory activity toward platelet aggregation and the potential to control template bleeding. This holds true in another peptide, analogue 48, which has an $IC_{50}$ of 0.7 $\mu$M in the platelet aggregation assay.

Industrial Application

The compositions of matter disclosed and claimed herein are industrially useful for the prevention and treatment of pathologies characterized by undesirable platelet aggregation, including thrombosis, stroke and vascular graft occlusion.

Although the invention has been described with reference to the presently-preferred embodiment, it should be understood that various modifications can be made without departing from the spirit of the invention. Accordingly, the invention is limited only by the following claims.

We claim:

1. A cyclic GD-containing peptide having the structure:

$$X_1X_2X_3X_4GDX_5X_7X_6$$

wherein $X_1$ is 0 to 20 amino acids;

$X_2$ is an amino acid that forms a bridge with $X_7$;

$X_3$ is 0 to 10 namino acids;

$X_4$ is a positively charged amino acids;

$X_5$ is a hydrophobic amino acid;

$X_6$ is a positively charged amino acid; and $X_7$ is an amino acid that forms a bridge with $X_2$.

2. The cyclic peptide of claim 1, wherein $X_2$ and $X_7$ are amino acids capable of forming a disulfide bridge.

3. The cyclic peptide of claim 1, wherein $X_2$ and $X_7$ are amino acids capable of forming a dicarba bridge.

4. The cyclic peptide of claim 1, wherein the amino acids capable of forming a bridge are selected from the group consisting of Cys, Pen, Pmp, Pmc, Mpr and Pas.

5. The cyclic peptide of claim 1, wherein $X_2$ and $X_7$ are amino acids capable of forming a lactam bridge.

6. The cyclic peptide of claim 5, wherein $X_2$ and $X_7$ are selected from the group consisting of aspartic acid, glutamic acid, lysine, ornithine, and α, β-diaminoproprionic acid.

7. The cyclic peptide of claim 5, wherein when $X_1$ is 0, the lactam bridge is between the N-terminal amine group of $X_2$ and the acid group of $X_7$.

8. The cyclic peptide of claim 7, wherein $X_2$ is preferably β-Ala, Gly or Arg.

9. The cyclic peptide of claim 5, wherein when $X_1$ is equal to or more than 1, the lactam bridge is between $X_2$ and $X_7$.

10. The cyclic peptide of claim 1, wherein $X_4$ is selected from the group consisting of Arg, Lys, homoArg and mimics thereof.

11. The cyclic peptide of claim 1, wherein said peptide possesses platelet aggregation inhibiting activity without substantially prolonging bleeding time.

12. The cyclic peptide of claim 1, wherein said cyclic peptides inhibit the binding of fibrinogen to GP IIb/IIIa more than they inhibit binding of fibronectin or vitronectin to their respective receptors.

13. A composition comprising the peptide of claim 1, 16 or 19 in a physiologically acceptable carrier.

14. A method of treatment or prophylaxis of thrombosis, comprising administering a therapeutically effective amount of the composition of claim 13.

15. A method of prophylaxis of vascular graft occlusion, comprising administering a therapeutically effective amount of the composition of claim 13.

16. A method of treatment or prophylaxis of a pathology characterized by undesirable platelet aggregation, comprising administering a therapeutically effective dose of the composition of claim 13.

17. The method of claim 16, wherein said pathology characterized by undesirable platelet aggregation is stroke.

* * * * *

SEQUENCE LISTING (1) GENERAL INFORMATION:

(iii) NUMBER OF SEQUENCES: 168

(2) INFORMATION FOR SEQ ID NO:1:

(i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pmc)"

(ix) FEATURE:
        (A) NAME/KEY: Peptide
        (B) LOCATION: 8
        (D) OTHER INFORMATION: /note= "Xaa = (Y-OMe)"

(xi) SEQUENCE DESCRIPTION: SEQ ID NO:1:

Arg Xaa Gly His Arg Gly Asp Xaa Arg Cys Arg
1               5                   10

(2) INFORMATION FOR SEQ ID NO:2:

(i) SEQUENCE CHARACTERISTICS:
        (A) LENGTH: 9 amino acids
        (B) TYPE: amino acid
        (D) TOPOLOGY: circular (ix) FEATURE:
        (A) NAME/KEY: Peptide
        (B) LOCATION: 7
        (D) OTHER INFORMATION: /note= "Xaa = (Y-OMe); C-terminal              amino (xi) SEQUENCE DESCRIPTION: SEQ ID NO:2:

Cys Ile Pro Arg Gly Asp Xaa Arg Cys
1               5

(2) INFORMATION FOR SEQ ID NO:3:

(i) SEQUENCE CHARACTERISTICS:
        (A) LENGTH: 9 amino acids
        (B) TYPE: amino acid
        (D) TOPOLOGY: circular (ix) FEATURE:
        (A) NAME/KEY: Peptide
        (B) LOCATION: 8
        (D) OTHER INFORMATION: /note= "Xaa = (Y-OMe); C-terminal              amino (xi) SEQUENCE DESCRIPTION: SEQ ID NO:3:

Cys Asn Pro Arg Gly Asp Xaa Arg Cys

```
1               5
```

(2) INFORMATION FOR SEQ ID NO:4:

(i) SEQUENCE CHARACTERISTICS:
        (A) LENGTH: 10 amino acids
        (B) TYPE: amino acid
        (D) TOPOLOGY: circular (ix) FEATURE:
        (A) NAME/KEY: Peptide
        (B) LOCATION: 1
        (D) OTHER INFORMATION: /note= "Xaa = 0 to 20 amino acids"

(ix) FEATURE:
        (A) NAME/KEY: Peptide
        (B) LOCATION: 2
        (D) OTHER INFORMATION: /note= "Xaa = 0 or an amino acid capable (ix) FEATURE:
        (A) NAME/KEY: Peptide
        (B) LOCATION: 3
        (D) OTHER INFORMATION: /note= "Xaa = 0 to 10 amino acid."

(ix) FEATURE:
        (A) NAME/KEY: Peptide
        (B) LOCATION: 4
        (D) OTHER INFORMATION: /note= "Xaa = a positive amino acid."

(ix) FEATURE:
        (A) NAME/KEY: Peptide
        (B) LOCATION: 7
        (D) OTHER INFORMATION: /note= "Xaa = hydrophobic amino acid."

(ix) FEATURE:
        (A) NAME/KEY: Peptide
        (B) LOCATION: 8
        (D) OTHER INFORMATION: /note= "Xaa = a positively charged amino (ix) FEATURE:
        (A) NAME/KEY: Peptide
        (B) LOCATION: 9
        (D) OTHER INFORMATION: /note= "Xaa = 0 or an amino acid capable (ix) FEATURE:
        (A) NAME/KEY: Peptide
        (B) LOCATION: 10
        (D) OTHER INFORMATION: /note= "Xaa = 0 to 20 amino acids."

(xi) SEQUENCE DESCRIPTION: SEQ ID NO:4:

```
Xaa Xaa Xaa Xaa Gly Asp Xaa Xaa Xaa Xaa
1               5                   10
```

(2) INFORMATION FOR SEQ ID NO:5:

(i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = Pen"

(xi) SEQUENCE DESCRIPTION: SEQ ID NO:5:

```
Gly Xaa Gly His Arg Gly Asp Leu Arg Cys Ala
1               5                   10
```

(2) INFORMATION FOR SEQ ID NO:6:

(i) SEQUENCE CHARACTERISTICS:
        (A) LENGTH: 11 amino acids
        (B) TYPE: amino acid (D) TOPOLOGY: circular (ix) FEATURE:
                (A) NAME/KEY: Peptide
                (B) LOCATION: 2
                (D) OTHER INFORMATION: /note= "Xaa = Pen"

(xi) SEQUENCE DESCRIPTION: SEQ ID NO:6:

Arg Xaa Gly His Arg Gly Asp Trp Arg Cys Arg
1               5                   10

(2) INFORMATION FOR SEQ ID NO:7:

(i) SEQUENCE CHARACTERISTICS:
                (A) LENGTH: 11 amino acids
                (B) TYPE: amino acid
                (D) TOPOLOGY: circular (ix) FEATURE:
                (A) NAME/KEY: Peptide
                (B) LOCATION: 2
                (D) OTHER INFORMATION: /note= "Xaa = Pen"

(ix) FEATURE:
                (A) NAME/KEY: Peptide
                (B) LOCATION: 8
                (D) OTHER INFORMATION: /note= "Xaa = (Cha)"

(xi) SEQUENCE DESCRIPTION: SEQ ID NO:7:

Arg Xaa Gly His Arg Gly Asp Xaa Arg Cys Arg
1               5                   10

(2) INFORMATION FOR SEQ ID NO:8:

(i) SEQUENCE CHARACTERISTICS:
                (A) LENGTH: 10 amino acids
                (B) TYPE: amino acid
                (D) TOPOLOGY: circular (ix) FEATURE:
                (A) NAME/KEY: Peptide
                (B) LOCATION: 1
                (D) OTHER INFORMATION: /note= "Xaa = Pmp"

(xi) SEQUENCE DESCRIPTION: SEQ ID NO:8:

Xaa Gly His Arg Gly Asp Leu Arg Cys Ala
1               5                   10

(2) INFORMATION FOR SEQ ID NO:9:

(i) SEQUENCE CHARACTERISTICS:
                (A) LENGTH: 11 amino acids
                (B) TYPE: amino acid
                (D) TOPOLOGY: circular (ix) FEATURE:
                (A) NAME/KEY: Peptide
                (B) LOCATION: 2
                (D) OTHER INFORMATION: /note= "Xaa = (dPen)"

(xi) SEQUENCE DESCRIPTION: SEQ ID NO:9:

Gly Xaa Gly His Arg Gly Asp Leu Arg Cys Ala
1               5                   10

(2) INFORMATION FOR SEQ ID NO:10:

(i) SEQUENCE CHARACTERISTICS:
                (A) LENGTH: 11 amino acids
                (B) TYPE: amino acid
                (D) TOPOLOGY: circular

```
    (ix) FEATURE:
         (A) NAME/KEY: Peptide
         (B) LOCATION: 2
         (D) OTHER INFORMATION: /note= "Xaa = (am-Pmp)"

(xi) SEQUENCE DESCRIPTION: SEQ ID NO:10:

Arg Xaa Gly His Arg Gly Asp Trp Arg Cys Arg
 1               5                  10

(2) INFORMATION FOR SEQ ID NO:11:

(i) SEQUENCE CHARACTERISTICS:
         (A) LENGTH: 11 amino acids
         (B) TYPE: amino acid
         (D) TOPOLOGY: circular (ix) FEATURE:
         (A) NAME/KEY: Peptide
         (B) LOCATION: 2
         (D) OTHER INFORMATION: /note= "Xaa = (am-Pmp)"

(ix) FEATURE:
         (A) NAME/KEY: Peptide
         (B) LOCATION: 8
         (D) OTHER INFORMATION: /note= "Xaa = (Y-OMe)"

(xi) SEQUENCE DESCRIPTION: SEQ ID NO:11:

Arg Xaa Gly His Arg Gly Asp Xaa Arg Cys Arg
 1               5                  10

(2) INFORMATION FOR SEQ ID NO:12:

(i) SEQUENCE CHARACTERISTICS:
         (A) LENGTH: 11 amino acids
         (B) TYPE: amino acid
         (D) TOPOLOGY: circular (ix) FEATURE:
         (A) NAME/KEY: Peptide
         (B) LOCATION: 2
         (D) OTHER INFORMATION: /note= "Xaa = (am-Pmp)"

(ix) FEATURE:
         (A) NAME/KEY: Peptide
         (B) LOCATION: 8
         (D) OTHER INFORMATION: /note= "Xaa = (Cl-F)"

(xi) SEQUENCE DESCRIPTION: SEQ ID NO:12:

Arg Xaa Gly His Arg Gly Asp Xaa Arg Cys Arg
 1               5                  10

(2) INFORMATION FOR SEQ ID NO:13:

(i) SEQUENCE CHARACTERISTICS:
         (A) LENGTH: 11 amino acids
         (B) TYPE: amino acid
         (D) TOPOLOGY: circular (ix) FEATURE:
         (A) NAME/KEY: Peptide
         (B) LOCATION: 2
         (D) OTHER INFORMATION: /note= "Xaa = (am-Pmp)"

(xi) SEQUENCE DESCRIPTION: SEQ ID NO:13:

Arg Xaa Gly His Arg Gly Asp Leu Arg Cys Arg
 1               5                  10

(2) INFORMATION FOR SEQ ID NO:14:

(i) SEQUENCE CHARACTERISTICS:
         (A) LENGTH: 11 amino acids
```

(B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (t-but-am-Pmp)"

(xi) SEQUENCE DESCRIPTION: SEQ ID NO:14:

Arg Xaa Gly His Arg Gly Asp Leu Arg Cys Arg
1               5                   10

(2) INFORMATION FOR SEQ ID NO:15:

(i) SEQUENCE CHARACTERISTICS:
        (A) LENGTH: 9 amino acids
        (B) TYPE: amino acid
        (D) TOPOLOGY: circular (ix) FEATURE:
        (A) NAME/KEY: Peptide
        (B) LOCATION: 7
        (D) OTHER INFORMATION: /note= "Xaa = (Y-OMe); C-terminal          amino (xi) SEQUENCE DESCRIPTION: SEQ ID NO:15:

Cys Asn Pro Lys Gly Asp Xaa Arg Cys
1               5

(2) INFORMATION FOR SEQ ID NO:16:

(i) SEQUENCE CHARACTERISTICS:
        (A) LENGTH: 9 amino acids
        (B) TYPE: amino acid
        (D) TOPOLOGY: circular (ix) FEATURE:
        (A) NAME/KEY: Peptide
        (B) LOCATION: 7
        (D) OTHER INFORMATION: /note= "Xaa = (O-N-Butyl-Y);              C-terminal (xi) SEQUENCE DESCRIPTION: SEQ ID NO:16:

Cys Asn Pro Arg Gly Asp Xaa Arg Cys
1               5

(2) INFORMATION FOR SEQ ID NO:17:

(i) SEQUENCE CHARACTERISTICS:
        (A) LENGTH: 7 amino acids
        (B) TYPE: amino acid
        (D) TOPOLOGY: circular (ix) FEATURE:
        (A) NAME/KEY: Peptide
        (B) LOCATION: 1
        (D) OTHER INFORMATION: /note= "Xaa = (Mpr)"

(ix) FEATURE:
        (A) NAME/KEY: Peptide
        (B) LOCATION: 5
        (D) OTHER INFORMATION: /note= "Xaa = (Y-OMe); C-terminal          amino (xi) SEQUENCE DESCRIPTION: SEQ ID NO:17:

Xaa Arg Gly Asp Xaa Arg Cys
1               5

(2) INFORMATION FOR SEQ ID NO:18:

(i) SEQUENCE CHARACTERISTICS:
        (A) LENGTH: 7 amino acids
        (B) TYPE: amino acid
        (D) TOPOLOGY: circular

```
    (ix) FEATURE:
          (A) NAME/KEY: Peptide
          (B) LOCATION: 5
          (D) OTHER INFORMATION: /note= "N-terminal is acetylated;        Xaa =

(ix) FEATURE:
          (A) NAME/KEY: Modified-site
          (B) LOCATION: 7
          (D) OTHER INFORMATION: /note= "Xaa = Cys-OH"

(xi) SEQUENCE DESCRIPTION: SEQ ID NO:18:

Cys Arg Gly Asp Xaa Arg Xaa
1               5

(2) INFORMATION FOR SEQ ID NO:19:

(i) SEQUENCE CHARACTERISTICS:
          (A) LENGTH: 7 amino acids
          (B) TYPE: amino acid
          (D) TOPOLOGY: circular (ix) FEATURE:
          (A) NAME/KEY: Peptide
          (B) LOCATION: 5
          (D) OTHER INFORMATION: /note= "N-terminal amino acid is         acetyla (ix) FEATURE:
          (A) NAME/KEY: Peptide
          (B) LOCATION: 7
          (D) OTHER INFORMATION: /note= "Xaa = (Pen); C-terminal          amino ac (xi) SEQUENCE DESCRIPTION: SEQ ID NO:19:

Cys Arg Gly Asp Xaa Arg Xaa
1               5

(2) INFORMATION FOR SEQ ID NO:20:

(i) SEQUENCE CHARACTERISTICS:
          (A) LENGTH: 7 amino acids
          (B) TYPE: amino acid
          (D) TOPOLOGY: circular (ix) FEATURE:
          (A) NAME/KEY: Peptide
          (B) LOCATION: 1
          (D) OTHER INFORMATION: /note= "N-terminal amino acid is         acetyla (ix) FEATURE:
          (A) NAME/KEY: Peptide
          (B) LOCATION: 5
          (D) OTHER INFORMATION: /note= "Xaa = (Y-OMe); C-terminal        amino (xi) SEQUENCE DESCRIPTION: SEQ ID NO:20:

Xaa Arg Gly Asp Xaa Arg Cys
1               5

(2) INFORMATION FOR SEQ ID NO:21:

(i) SEQUENCE CHARACTERISTICS:
          (A) LENGTH: 7 amino acids
          (B) TYPE: amino acid
          (D) TOPOLOGY: circular (ix) FEATURE:
          (A) NAME/KEY: Peptide
          (B) LOCATION: 5
          (D) OTHER INFORMATION: /note= "N-terminal amino acid is         acetyla (xi) SEQUENCE DESCRIPTION: SEQ ID NO:21:

Cys Lys Gly Asp Xaa Arg Cys
1               5
```

(2) INFORMATION FOR SEQ ID NO:22:

(i) SEQUENCE CHARACTERISTICS:
       (A) LENGTH: 7 amino acids
       (B) TYPE: amino acid
       (D) TOPOLOGY: circular (ix) FEATURE:
       (A) NAME/KEY: Peptide
       (B) LOCATION: 5
       (D) OTHER INFORMATION: /note= "N-terminal amino acid is            acetyla (ix) FEATURE:
       (A) NAME/KEY: Peptide
       (B) LOCATION: 7
       (D) OTHER INFORMATION: /note= "Xaa = (dPen); C-terminal            amino a (xi) SEQUENCE DESCRIPTION: SEQ ID NO:22:

Cys Arg Gly Asp Xaa Arg Xaa
1               5

(2) INFORMATION FOR SEQ ID NO:23:

(i) SEQUENCE CHARACTERISTICS:
       (A) LENGTH: 7 amino acids
       (B) TYPE: amino acid
       (D) TOPOLOGY: circular (ix) FEATURE:
       (A) NAME/KEY: Peptide
       (B) LOCATION: 5
       (D) OTHER INFORMATION: /note= "N-terminal amino acid is            acetyla (xi) SEQUENCE DESCRIPTION: SEQ ID NO:23:

Cys Arg Gly Asp Xaa Arg Cys
1               5

(2) INFORMATION FOR SEQ ID NO:24:

(i) SEQUENCE CHARACTERISTICS:
       (A) LENGTH: 8 amino acids
       (B) TYPE: amino acid
       (D) TOPOLOGY: circular (ix) FEATURE:
       (A) NAME/KEY: Peptide
       (B) LOCATION: 5
       (D) OTHER INFORMATION: /note= "N-terminal amino acid is            acetyla (xi) SEQUENCE DESCRIPTION: SEQ ID NO:24:

Cys Arg Gly Asp Xaa Arg Cys Arg
1               5

(2) INFORMATION FOR SEQ ID NO:25:

(i) SEQUENCE CHARACTERISTICS:
       (A) LENGTH: 7 amino acids
       (B) TYPE: amino acid
       (D) TOPOLOGY: circular (ix) FEATURE:
       (A) NAME/KEY: Peptide
       (B) LOCATION: 1
       (D) OTHER INFORMATION: /note= "Xaa = (Mpr)"

(ix) FEATURE:
       (A) NAME/KEY: Peptide
       (B) LOCATION: 5
       (D) OTHER INFORMATION: /note= "Xaa = (O-n-Butyl-Y);            C-terminal (xi) SEQUENCE DESCRIPTION: SEQ ID NO:25:

```
Xaa Arg Gly Asp Xaa Arg Cys
1               5

(2) INFORMATION FOR SEQ ID NO:26:

(i) SEQUENCE CHARACTERISTICS:
        (A) LENGTH: 7 amino acids
        (B) TYPE: amino acid
        (D) TOPOLOGY: circular (ix) FEATURE:
        (A) NAME/KEY: Peptide
        (B) LOCATION: 1
        (D) OTHER INFORMATION: /note= "Xaa = (Mpr)"

(ix) FEATURE:
        (A) NAME/KEY: Peptide
        (B) LOCATION: 5
        (D) OTHER INFORMATION: /note= "Xaa = (Y-OMe); C-terminal        amino (xi) SEQUENCE DESCRIPTION: SEQ ID NO:26:

Xaa Lys Gly Asp Xaa Arg Cys
1               5

(2) INFORMATION FOR SEQ ID NO:27:

(i) SEQUENCE CHARACTERISTICS:
        (A) LENGTH: 7 amino acids
        (B) TYPE: amino acid
        (D) TOPOLOGY: circular (ix) FEATURE:
        (A) NAME/KEY: Peptide
        (B) LOCATION: 1
        (D) OTHER INFORMATION: /note= "Xaa = (Pmp)"

(ix) FEATURE:
        (A) NAME/KEY: Peptide
        (B) LOCATION: 5
        (D) OTHER INFORMATION: /note= "Xaa = (Y-OMe); C-terminal        amino (xi) SEQUENCE DESCRIPTION: SEQ ID NO:27:

Xaa Arg Gly Asp Xaa Arg Cys
1               5

(2) INFORMATION FOR SEQ ID NO:28:

(i) SEQUENCE CHARACTERISTICS:
        (A) LENGTH: 7 amino acids
        (B) TYPE: amino acid
        (D) TOPOLOGY: circular (ix) FEATURE:
        (A) NAME/KEY: Peptide
        (B) LOCATION: 5
        (D) OTHER INFORMATION: /note= "N-terminal amino acid is          acetyla (xi) SEQUENCE DESCRIPTION: SEQ ID NO:28:

Cys Arg Gly Asp Xaa Arg Cys
1               5

(2) INFORMATION FOR SEQ ID NO:29:

(i) SEQUENCE CHARACTERISTICS:
        (A) LENGTH: 7 amino acids
        (B) TYPE: amino acid
        (D) TOPOLOGY: circular (ix) FEATURE:
        (A) NAME/KEY: Peptide
        (B) LOCATION: 5
```

(D) OTHER INFORMATION: /note= "N-terminal amino acid is        acetyla (xi) SEQUENCE DESCRIPTION: SEQ ID NO:29:

Cys Arg Gly Asp Xaa Arg Cys
1               5

(2) INFORMATION FOR SEQ ID NO:30:

(i) SEQUENCE CHARACTERISTICS:
        (A) LENGTH: 8 amino acids
        (B) TYPE: amino acid
        (D) TOPOLOGY: circular (ix) FEATURE:
        (A) NAME/KEY: Peptide
        (B) LOCATION: 1
        (D) OTHER INFORMATION: /note= "N-terminal amino acid is        acetyla (ix) FEATURE:
        (A) NAME/KEY: Peptide
        (B) LOCATION: 6
        (D) OTHER INFORMATION: /note= "Xaa = (Y-OMe); C-terminal          amino (xi) SEQUENCE DESCRIPTION: SEQ ID NO:30:

Xaa His Arg Gly Asp Xaa Arg Cys
1               5

(2) INFORMATION FOR SEQ ID NO:31:

(i) SEQUENCE CHARACTERISTICS:
        (A) LENGTH: 9 amino acids
        (B) TYPE: amino acid
        (D) TOPOLOGY: circular (ix) FEATURE:
        (A) NAME/KEY: Peptide
        (B) LOCATION: 7
        (D) OTHER INFORMATION: /note= "Xaa = (O-n-Butyl-Y);         C-terminal (xi) SEQUENCE DESCRIPTION: SEQ ID NO:31:

Gly Asn Pro Arg Gly Asp Xaa Arg Glu
1               5

(2) INFORMATION FOR SEQ ID NO:32:

(i) SEQUENCE CHARACTERISTICS:
        (A) LENGTH: 6 amino acids
        (B) TYPE: amino acid
        (D) TOPOLOGY: circular (ix) FEATURE:
        (A) NAME/KEY: Peptide
        (B) LOCATION: 4
        (D) OTHER INFORMATION: /note= "Xaa = (Y-OMe); C-terminal          amino (xi) SEQUENCE DESCRIPTION: SEQ ID NO:32:

Arg Gly Asp Xaa Arg Glu
1               5

(2) INFORMATION FOR SEQ ID NO:33:

(i) SEQUENCE CHARACTERISTICS:
        (A) LENGTH: 7 amino acids
        (B) TYPE: amino acid
        (D) TOPOLOGY: circular (ix) FEATURE:
        (A) NAME/KEY: Peptide
        (B) LOCATION: 5
        (D) OTHER INFORMATION: /note= "Xaa = (Y-OMe); C-terminal          amino (xi) SEQUENCE DESCRIPTION: SEQ ID NO:33:

Gly Arg Gly Asp Xaa Arg Glu
1               5

(2) INFORMATION FOR SEQ ID NO:34:

(i) SEQUENCE CHARACTERISTICS:
        (A) LENGTH: 9 amino acids
        (B) TYPE: amino acid
        (D) TOPOLOGY: circular (ix) FEATURE:
        (A) NAME/KEY: Peptide
        (B) LOCATION: 7
        (D) OTHER INFORMATION: /note= "Xaa = (Y-OMe); C-terminal          amino (xi) SEQUENCE DESCRIPTION: SEQ ID NO:34:

Gly Asn Pro Arg Gly Asp Xaa Arg Glu
1               5

(2) INFORMATION FOR SEQ ID NO:35:

(i) SEQUENCE CHARACTERISTICS:
        (A) LENGTH: 9 amino acids
        (B) TYPE: amino acid
        (D) TOPOLOGY: circular (ix) FEATURE:
        (A) NAME/KEY: Peptide
        (B) LOCATION: 7
        (D) OTHER INFORMATION: /note= "Xaa = (Y-OMe); C-terminal          amino (xi) SEQUENCE DESCRIPTION: SEQ ID NO:35:

Gly Asn Pro Arg Gly Asp Xaa Arg Asp
1               5

(2) INFORMATION FOR SEQ ID NO:36:

(i) SEQUENCE CHARACTERISTICS:
        (A) LENGTH: 7 amino acids
        (B) TYPE: amino acid
        (D) TOPOLOGY: circular (ix) FEATURE:
        (A) NAME/KEY: Peptide
        (B) LOCATION: 1
        (D) OTHER INFORMATION: /note= "Xaa = (beta-Ala)"

(ix) FEATURE:
        (A) NAME/KEY: Peptide
        (B) LOCATION: 5
        (D) OTHER INFORMATION: /note= "Xaa = (Y-OMe); C-terminal          amino (xi) SEQUENCE DESCRIPTION: SEQ ID NO:36:

Xaa Arg Gly Asp Xaa Arg Asp
1               5

(2) INFORMATION FOR SEQ ID NO:37:

(i) SEQUENCE CHARACTERISTICS:
        (A) LENGTH: 9 amino acids
        (B) TYPE: amino acid
        (D) TOPOLOGY: circular (ix) FEATURE:
        (A) NAME/KEY: Peptide
        (B) LOCATION: 1
        (D) OTHER INFORMATION: /note= "Xaa = (beta-Ala)"

(ix) FEATURE:
        (A) NAME/KEY: Peptide (B) LOCATION: 7
        (D) OTHER INFORMATION: /note= "Xaa = (Y-OMe); C-terminal amino (xi) SEQUENCE DESCRIPTION: SEQ ID NO:37:

Xaa Asn Pro Arg Gly Asp Xaa Arg Asp
1               5

(2) INFORMATION FOR SEQ ID NO:38:

(i) SEQUENCE CHARACTERISTICS:
        (A) LENGTH: 7 amino acids
        (B) TYPE: amino acid
        (D) TOPOLOGY: circular (ix) FEATURE:
        (A) NAME/KEY: Peptide
        (B) LOCATION: 5
        (D) OTHER INFORMATION: /note= "Xaa = (O-n-Butyl-Y); C-terminal (xi) SEQUENCE DESCRIPTION: SEQ ID NO:38:

Gly Arg Gly Asp Xaa Arg Glu
1               5

(2) INFORMATION FOR SEQ ID NO:39:

(i) SEQUENCE CHARACTERISTICS:
        (A) LENGTH: 8 amino acids
        (B) TYPE: amino acid
        (D) TOPOLOGY: circular (ix) FEATURE:
        (A) NAME/KEY: Peptide
        (B) LOCATION: 5
        (D) OTHER INFORMATION: /note= "N-terminal amino acid is acetyla (ix) FEATURE:
        (A) NAME/KEY: Peptide
        (B) LOCATION: 7
        (D) OTHER INFORMATION: /note= "Xaa = (Pen); C-terminal amino ac (xi) SEQUENCE DESCRIPTION: SEQ ID NO:39:

Cys Arg Gly Asp Xaa Pro Xaa Arg
1               5

(2) INFORMATION FOR SEQ ID NO:40:

(i) SEQUENCE CHARACTERISTICS:
        (A) LENGTH: 6 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "N-terminal amino acid is acetyla (ix) FEATURE:
        (A) NAME/KEY: Peptide
        (B) LOCATION: 5
        (D) OTHER INFORMATION: /note= "Xaa = (Pen); C-terminal amino ac (xi) SEQUENCE DESCRIPTION: SEQ ID NO:40:

Cys Xaa Gly Asp Xaa Arg
1               5

(2) INFORMATION FOR SEQ ID NO:41:

(i) SEQUENCE CHARACTERISTICS:
        (A) LENGTH: 5 amino acids
        (B) TYPE: amino acid
        (D) TOPOLOGY: linear

```
    (ix) FEATURE:
         (A) NAME/KEY: Peptide
         (B) LOCATION: 4
         (D) OTHER INFORMATION: /note= "N-terminal amino acid is          acetyla (xi) SEQUENCE DESCRIPTION: SEQ ID NO:41:

Arg Gly Asp Xaa Arg
1               5

(2) INFORMATION FOR SEQ ID NO:42:

(i) SEQUENCE CHARACTERISTICS:
        (A) LENGTH: 10 amino acids
        (B) TYPE: amino acid
        (D) TOPOLOGY: circular (ix) FEATURE:
         (A) NAME/KEY: Peptide
         (B) LOCATION: 2
         (D) OTHER INFORMATION: /note= "Xaa = Pen"

(ix) FEATURE:
         (A) NAME/KEY: Peptide
         (B) LOCATION: 7
         (D) OTHER INFORMATION: /note= "Xaa = F or W"

(xi) SEQUENCE DESCRIPTION: SEQ ID NO:42:

Gly Xaa Gly Arg Gly Asp Xaa Pro Cys Ala
1               5                   10

(2) INFORMATION FOR SEQ ID NO:43:

(i) SEQUENCE CHARACTERISTICS:
        (A) LENGTH: 11 amino acids
        (B) TYPE: amino acid
        (D) TOPOLOGY: circular (ix) FEATURE:
         (A) NAME/KEY: Peptide
         (B) LOCATION: 2
         (D) OTHER INFORMATION: /note= "Xaa = Pen"

(ix) FEATURE:
         (A) NAME/KEY: Peptide
         (B) LOCATION: 8
         (D) OTHER INFORMATION: /note= "Xaa = F or W"

(xi) SEQUENCE DESCRIPTION: SEQ ID NO:43:

Gly Xaa Gly His Arg Gly Asp Xaa Arg Cys Ala
1               5                   10

(2) INFORMATION FOR SEQ ID NO:44:

(i) SEQUENCE CHARACTERISTICS:
        (A) LENGTH: 10 amino acids
        (B) TYPE: amino acid
        (D) TOPOLOGY: circular (ix) FEATURE:
         (A) NAME/KEY: Peptide
         (B) LOCATION: 2
         (D) OTHER INFORMATION: /note= "Xaa = Pen"

(xi) SEQUENCE DESCRIPTION: SEQ ID NO:44:

Gly Xaa Gly Arg Gly Asp Ser Pro Cys Ala
1               5                   10

(2) INFORMATION FOR SEQ ID NO:45:

(i) SEQUENCE CHARACTERISTICS:
```

(A) LENGTH: 10 amino acids
            (B) TYPE: amino acid
            (D) TOPOLOGY: circular (ix) FEATURE:
            (A) NAME/KEY: Peptide
            (B) LOCATION: 1
            (D) OTHER INFORMATION: /note= "Xaa = R or K"

(ix) FEATURE:
            (A) NAME/KEY: Peptide
            (B) LOCATION: 2
            (D) OTHER INFORMATION: /note= "Xaa = Pen"

(xi) SEQUENCE DESCRIPTION: SEQ ID NO:45:

Xaa Xaa Gly Arg Gly Asp Ser Pro Cys Ala
1               5                   10

(2) INFORMATION FOR SEQ ID NO:46:

(i) SEQUENCE CHARACTERISTICS:
            (A) LENGTH: 11 amino acids
            (B) TYPE: amino acid
            (D) TOPOLOGY: circular (ix) FEATURE:
            (A) NAME/KEY: Peptide
            (B) LOCATION: 1
            (D) OTHER INFORMATION: /note= "Xaa = R or K"

(ix) FEATURE:
            (A) NAME/KEY: Peptide
            (B) LOCATION: 2
            (D) OTHER INFORMATION: /note= "Xaa = Pen"

(xi) SEQUENCE DESCRIPTION: SEQ ID NO:46:

Xaa Xaa Gly His Arg Gly Asp Leu Arg Cys Ala
1               5                   10

(2) INFORMATION FOR SEQ ID NO:47:

(i) SEQUENCE CHARACTERISTICS:
            (A) LENGTH: 11 amino acids
            (B) TYPE: amino acid
            (D) TOPOLOGY: circular (ix) FEATURE:
            (A) NAME/KEY: Peptide
            (B) LOCATION: 2
            (D) OTHER INFORMATION: /note= "Xaa = organic mimic       bridging str (xi) SEQUENCE DESCRIPTION: SEQ ID NO:47:

Gly Xaa Gly His Arg Gly Asp Leu Arg Cys Ala
1               5                   10

(2) INFORMATION FOR SEQ ID NO:48:

(i) SEQUENCE CHARACTERISTICS:
            (A) LENGTH: 11 amino acids
            (B) TYPE: amino acid
            (D) TOPOLOGY: circular (ix) FEATURE:
            (A) NAME/KEY: Peptide
            (B) LOCATION: 2
            (D) OTHER INFORMATION: /note= "Xaa = (1-Pen)"

(xi) SEQUENCE DESCRIPTION: SEQ ID NO:48:

Gly Xaa Gly His Arg Gly Asp Leu Arg Cys Ala
1               5                   10

(2) INFORMATION FOR SEQ ID NO:49:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:49:

Gly Arg Gly Asp Ser Pro
1               5

(2) INFORMATION FOR SEQ ID NO:50:

(i) SEQUENCE CHARACTERISTICS:
        (A) LENGTH: 10 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pen)"

(xi) SEQUENCE DESCRIPTION: SEQ ID NO:50:

Gly Xaa Gly Arg Gly Asp Thr Pro Cys Ala
1               5                   10

(2) INFORMATION FOR SEQ ID NO:51:

(i) SEQUENCE CHARACTERISTICS:
        (A) LENGTH: 10 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pen)"

(xi) SEQUENCE DESCRIPTION: SEQ ID NO:51:

Gly Xaa Gly Arg Gly Asp Thr Pro Cys Ala
1               5                   10

(2) INFORMATION FOR SEQ ID NO:52:

(i) SEQUENCE CHARACTERISTICS:
        (A) LENGTH: 10 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pen)"

(xi) SEQUENCE DESCRIPTION: SEQ ID NO:52:

Arg Xaa Gly Arg Gly Asp Trp Pro Cys Arg
1               5                   10

(2) INFORMATION FOR SEQ ID NO:53:

(i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pen)"

(xi) SEQUENCE DESCRIPTION: SEQ ID NO:53:

Arg Xaa Gly His Arg Gly Asp Leu Arg Cys Arg
1               5                  10

(2) INFORMATION FOR SEQ ID NO:54:

(i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pen)"

(ix) FEATURE:
        (A) NAME/KEY: Peptide
        (B) LOCATION: 8
        (D) OTHER INFORMATION: /note= "Xaa = (1-Nal)"

(xi) SEQUENCE DESCRIPTION: SEQ ID NO:54:

Arg Xaa Gly His Arg Gly Asp Xaa Arg Cys Arg
1               5                  10

(2) INFORMATION FOR SEQ ID NO:55:

(i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (am-Pmp)"

(xi) SEQUENCE DESCRIPTION: SEQ ID NO:55:

Gly Xaa Gly His Arg Gly Asp Leu Arg Cys Ala
1               5                  10

(2) INFORMATION FOR SEQ ID NO:56:

(i) SEQUENCE CHARACTERISTICS:
        (A) LENGTH: 10 amino acids
        (B) TYPE: amino acid
        (D) TOPOLOGY: circular (ix) FEATURE:
        (A) NAME/KEY: Peptide
        (B) LOCATION: 1
        (D) OTHER INFORMATION: /note= "Xaa = (t-but-am-Pmp)"

(ix) FEATURE:
        (A) NAME/KEY: Peptide
        (B) LOCATION: 9
        (D) OTHER INFORMATION: /note= "Xaa = (Pen)"

(xi) SEQUENCE DESCRIPTION: SEQ ID NO:56:

Xaa Gly His Arg Gly Asp Leu Arg Xaa Ala
1               5                  10

(2) INFORMATION FOR SEQ ID NO:57:

(i) SEQUENCE CHARACTERISTICS:
        (A) LENGTH: 8 amino acids
        (B) TYPE: amino acid
        (D) TOPOLOGY: circular (ix) FEATURE:
        (A) NAME/KEY: Peptide (B) LOCATION: 2
        (D) OTHER INFORMATION: /note= "Xaa = (am-Pmp)"

(ix) FEATURE:
        (A) NAME/KEY: Peptide
        (B) LOCATION: 6
        (D) OTHER INFORMATION: /note= "Xaa = (Cha)"

(xi) SEQUENCE DESCRIPTION: SEQ ID NO:57:

Arg Xaa Arg Gly Asp Xaa Cys Arg
1               5

(2) INFORMATION FOR SEQ ID NO:58:

(i) SEQUENCE CHARACTERISTICS:
        (A) LENGTH: 10 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (am-Pmp)"

(xi) SEQUENCE DESCRIPTION: SEQ ID NO:58:

Arg Xaa Gly Arg Gly Asp Trp Pro Cys Arg
1               5                  10

(2) INFORMATION FOR SEQ ID NO:59:

(i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pmc)"

(ix) FEATURE:
        (A) NAME/KEY: Peptide
        (B) LOCATION: 8
        (D) OTHER INFORMATION: /note= "Xaa = (O-n-hexyl-Y)"

(xi) SEQUENCE DESCRIPTION: SEQ ID NO:59:

Arg Xaa Gly His Arg Gly Asp Xaa Arg Cys Arg
1               5                  10

(2) INFORMATION FOR SEQ ID NO:60:

(i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pmc)"

(ix) FEATURE:
        (A) NAME/KEY: Peptide
        (B) LOCATION: 8
        (D) OTHER INFORMATION: /note= "Xaa = (3,5-diiodo-Y)"

(xi) SEQUENCE DESCRIPTION: SEQ ID NO:60:

Arg Xaa Gly His Arg Gly Asp Xaa Arg Cys Arg
1               5                  10

(2) INFORMATION FOR SEQ ID NO:61:

(i) SEQUENCE CHARACTERISTICS:
            (A) LENGTH: 11 amino acids
            (B) TYPE: amino acid
            (D) TOPOLOGY: circular (ix) FEATURE:
            (A) NAME/KEY: Peptide
            (B) LOCATION: 2
            (D) OTHER INFORMATION: /note= "Xaa = (Pmc)"

(ix) FEATURE:
            (A) NAME/KEY: Peptide
            (B) LOCATION: 8
            (D) OTHER INFORMATION: /note= "Xaa = (Hpa)"

(xi) SEQUENCE DESCRIPTION: SEQ ID NO:61:

Arg Xaa Gly His Arg Gly Asp Xaa Arg Cys Arg
1               5                   10

(2) INFORMATION FOR SEQ ID NO:62:

(i) SEQUENCE CHARACTERISTICS:
            (A) LENGTH: 11 amino acids
            (B) TYPE: amino acid
            (D) TOPOLOGY: circular (ix) FEATURE:
            (A) NAME/KEY: Peptide
            (B) LOCATION: 2
            (D) OTHER INFORMATION: /note= "Xaa = (Pmc)"

(ix) FEATURE:
            (A) NAME/KEY: Peptide
            (B) LOCATION: 8
            (D) OTHER INFORMATION: /note= "Xaa = (2-Nal)"

(xi) SEQUENCE DESCRIPTION: SEQ ID NO:62:

Arg Xaa Gly His Arg Gly Asp Xaa Arg Cys Arg
1               5                   10

(2) INFORMATION FOR SEQ ID NO:63:

(i) SEQUENCE CHARACTERISTICS:
            (A) LENGTH: 11 amino acids
            (B) TYPE: amino acid
            (D) TOPOLOGY: circular (ix) FEATURE:
            (A) NAME/KEY: Peptide
            (B) LOCATION: 2
            (D) OTHER INFORMATION: /note= "Xaa = (Pmc)"

(ix) FEATURE:
            (A) NAME/KEY: Peptide
            (B) LOCATION: 8
            (D) OTHER INFORMATION: /note= "Xaa = (O-n-butyl-Y)"

(xi) SEQUENCE DESCRIPTION: SEQ ID NO:63:

Arg Xaa Gly His Arg Gly Asp Xaa Arg Cys Arg
1               5                   10

(2) INFORMATION FOR SEQ ID NO:64:

(i) SEQUENCE CHARACTERISTICS:
            (A) LENGTH: 11 amino acids
            (B) TYPE: amino acid
            (D) TOPOLOGY: circular (ix) FEATURE:
            (A) NAME/KEY: Peptide
            (B) LOCATION: 2
            (D) OTHER INFORMATION: /note= "Xaa = (Pmc)"

```
       (ix) FEATURE:
            (A) NAME/KEY: Peptide
            (B) LOCATION: 8
            (D) OTHER INFORMATION: /note= "Xaa = (p-nitro-F)"

(xi) SEQUENCE DESCRIPTION: SEQ ID NO:64:

Arg Xaa Gly His Arg Gly Asp Xaa Arg Cys Arg
1               5                   10

(2) INFORMATION FOR SEQ ID NO:65:

(i) SEQUENCE CHARACTERISTICS:
            (A) LENGTH: 11 amino acids
            (B) TYPE: amino acid
            (D) TOPOLOGY: circular (ix) FEATURE:
            (A) NAME/KEY: Peptide
            (B) LOCATION: 2
            (D) OTHER INFORMATION: /note= "Xaa = (Pmc)"

(xi) SEQUENCE DESCRIPTION: SEQ ID NO:65:

Arg Xaa Gly His Arg Gly Asp Val Arg Cys Arg
1               5                   10

(2) INFORMATION FOR SEQ ID NO:66:

(i) SEQUENCE CHARACTERISTICS:
            (A) LENGTH: 11 amino acids
            (B) TYPE: amino acid
            (D) TOPOLOGY: circular (ix) FEATURE:
            (A) NAME/KEY: Peptide
            (B) LOCATION: 2
            (D) OTHER INFORMATION: /note= "Xaa = (Pmc)"

(xi) SEQUENCE DESCRIPTION: SEQ ID NO:66:

Arg Xaa Gly His Arg Gly Asp Phe Arg Cys Arg
1               5                   10

(2) INFORMATION FOR SEQ ID NO:67:

(i) SEQUENCE CHARACTERISTICS:
            (A) LENGTH: 11 amino acids
            (B) TYPE: amino acid
            (D) TOPOLOGY: circular (ix) FEATURE:
            (A) NAME/KEY: Peptide
            (B) LOCATION: 2
            (D) OTHER INFORMATION: /note= "Xaa = (Pmc)"

(xi) SEQUENCE DESCRIPTION: SEQ ID NO:67:

Arg Xaa Gly His Arg Gly Asp Tyr Arg Cys Arg
1               5                   10

(2) INFORMATION FOR SEQ ID NO:68:

(i) SEQUENCE CHARACTERISTICS:
            (A) LENGTH: 11 amino acids
            (B) TYPE: amino acid
            (D) TOPOLOGY: circular (ix) FEATURE:
            (A) NAME/KEY: Peptide
            (B) LOCATION: 2
            (D) OTHER INFORMATION: /note= "Xaa = (Pmc)"

(ix) FEATURE:
```

```
            (A) NAME/KEY: Peptide
            (B) LOCATION: 8
            (D) OTHER INFORMATION: /note= "Xaa = (Y-OMe)"

(xi) SEQUENCE DESCRIPTION: SEQ ID NO:68:

Arg Xaa Arg His Arg Gly Asp Xaa Arg Cys Arg
1               5                   10

(2) INFORMATION FOR SEQ ID NO:69:

(i) SEQUENCE CHARACTERISTICS:
        (A) LENGTH: 11 amino acids
        (B) TYPE: amino acid
        (D) TOPOLOGY: circular (ix) FEATURE:
         (A) NAME/KEY: Peptide
         (B) LOCATION: 2
         (D) OTHER INFORMATION: /note= "Xaa = (Pmc)"

(ix) FEATURE:
         (A) NAME/KEY: Peptide
         (B) LOCATION: 8
         (D) OTHER INFORMATION: /note= "Xaa = (Phg)"

(xi) SEQUENCE DESCRIPTION: SEQ ID NO:69:

Arg Xaa Gly His Arg Gly Asp Xaa Arg Cys Arg
1               5                   10

(2) INFORMATION FOR SEQ ID NO:70:

(i) SEQUENCE CHARACTERISTICS:
        (A) LENGTH: 11 amino acids
        (B) TYPE: amino acid
        (D) TOPOLOGY: circular (ix) FEATURE:
         (A) NAME/KEY: Peptide
         (B) LOCATION: 2
         (D) OTHER INFORMATION: /note= "Xaa = (Pmc)"

(ix) FEATURE:
         (A) NAME/KEY: Peptide
         (B) LOCATION: 8
         (D) OTHER INFORMATION: /note= "Xaa = (Y-OMe)"

(xi) SEQUENCE DESCRIPTION: SEQ ID NO:70:

Phe Xaa Gly His Arg Gly Asp Xaa Arg Cys Arg
1               5                   10

(2) INFORMATION FOR SEQ ID NO:71:

(i) SEQUENCE CHARACTERISTICS:
        (A) LENGTH: 11 amino acids
        (B) TYPE: amino acid
        (D) TOPOLOGY: circular (ix) FEATURE:
         (A) NAME/KEY: Peptide
         (B) LOCATION: 2
         (D) OTHER INFORMATION: /note= "Xaa = (dPen)"

(ix) FEATURE:
         (A) NAME/KEY: Peptide
         (B) LOCATION: 8
         (D) OTHER INFORMATION: /note= "Xaa = (p-iodo-F)"

(xi) SEQUENCE DESCRIPTION: SEQ ID NO:71:

Arg Xaa Gly His Arg Gly Asp Xaa Arg Cys Arg
1               5                   10
```

(2) INFORMATION FOR SEQ ID NO:72:

(i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pmc)"

(ix) FEATURE:
        (A) NAME/KEY: Peptide
        (B) LOCATION: 8
        (D) OTHER INFORMATION: /note= "Xaa = (Y-OMe)"

(xi) SEQUENCE DESCRIPTION: SEQ ID NO:72:

Lys Xaa Gly His Arg Gly Asp Xaa Arg Cys Lys
1               5                   10

(2) INFORMATION FOR SEQ ID NO:73:

(i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pmc)"

(ix) FEATURE:
        (A) NAME/KEY: Peptide
        (B) LOCATION: 8
        (D) OTHER INFORMATION: /note= "Xaa = (Y-OMe)"

(ix) FEATURE:
        (A) NAME/KEY: Peptide
        (B) LOCATION: 9
        (D) OTHER INFORMATION: /note= "Xaa = Orn"

(xi) SEQUENCE DESCRIPTION: SEQ ID NO:73:

Arg Xaa Gly His Arg Gly Asp Xaa Xaa Cys Arg
1               5                   10

(2) INFORMATION FOR SEQ ID NO:74:

(i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pmc)"

(ix) FEATURE:
        (A) NAME/KEY: Peptide
        (B) LOCATION: 8
        (D) OTHER INFORMATION: /note= "Xaa = (Y-OMe)"

(xi) SEQUENCE DESCRIPTION: SEQ ID NO:74:

His Xaa Gly His Arg Gly Asp Xaa Arg Cys Arg
1               5                   10

(2) INFORMATION FOR SEQ ID NO:75:

(i) SEQUENCE CHARACTERISTICS:
        (A) LENGTH: 11 amino acids
        (B) TYPE: amino acid (D) TOPOLOGY: circular (ix) FEATURE:
        (A) NAME/KEY: Peptide
        (B) LOCATION: 2
        (D) OTHER INFORMATION: /note= "Xaa = (Pmc)"

(ix) FEATURE:
        (A) NAME/KEY: Peptide
        (B) LOCATION: 8
        (D) OTHER INFORMATION: /note= "Xaa = (p-amino-F)"

(xi) SEQUENCE DESCRIPTION: SEQ ID NO:75:

Arg Xaa Gly His Arg Gly Asp Xaa Arg Cys Arg
1               5                   10

(2) INFORMATION FOR SEQ ID NO:76:

(i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pmc)"

(ix) FEATURE:
        (A) NAME/KEY: Peptide
        (B) LOCATION: 8
        (D) OTHER INFORMATION: /note= "Xaa = (Y-OMe)"

(xi) SEQUENCE DESCRIPTION: SEQ ID NO:76:

Arg Xaa Asn His Arg Gly Asp Xaa Arg Cys Arg
1               5                   10

(2) INFORMATION FOR SEQ ID NO:77:

(i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pmc)"

(ix) FEATURE:
        (A) NAME/KEY: Peptide
        (B) LOCATION: 8
        (D) OTHER INFORMATION: /note= "Xaa = (Y-OMe)"

(xi) SEQUENCE DESCRIPTION: SEQ ID NO:77:

Gly Xaa Gly His Arg Gly Asp Xaa Arg Cys Arg
1               5                   10

(2) INFORMATION FOR SEQ ID NO:78:

(i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pmc)"

(ix) FEATURE:
        (A) NAME/KEY: Peptide
        (B) LOCATION: 8

(D) OTHER INFORMATION: /note= "Xaa = (Y-OMe)"

(xi) SEQUENCE DESCRIPTION: SEQ ID NO:78:

Arg Xaa Gly His Arg Gly Asp Xaa Lys Cys Arg
1               5                   10

(2) INFORMATION FOR SEQ ID NO:79:

(i) SEQUENCE CHARACTERISTICS:
            (A) LENGTH: 11 amino acids
            (B) TYPE: amino acid
            (D) TOPOLOGY: circular (ix) FEATURE:
            (A) NAME/KEY: Peptide
            (B) LOCATION: 2
            (D) OTHER INFORMATION: /note= "Xaa = (Pen)"

(xi) SEQUENCE DESCRIPTION: SEQ ID NO:79:

Gly Xaa Ile Ala Arg Gly Asp Trp Asn Cys Ala
1               5                   10

(2) INFORMATION FOR SEQ ID NO:80:

(i) SEQUENCE CHARACTERISTICS:
            (A) LENGTH: 11 amino acids
            (B) TYPE: amino acid
            (D) TOPOLOGY: circular (ix) FEATURE:
            (A) NAME/KEY: Peptide
            (B) LOCATION: 2
            (D) OTHER INFORMATION: /note= "Xaa = (Pmc)"

(ix) FEATURE:
            (A) NAME/KEY: Peptide
            (B) LOCATION: 8
            (D) OTHER INFORMATION: /note= "Xaa = (Y-OMe)"

(xi) SEQUENCE DESCRIPTION: SEQ ID NO:80:

Thr Xaa Gly His Arg Gly Asp Xaa Arg Cys Arg
1               5                   10

(2) INFORMATION FOR SEQ ID NO:81:

(i) SEQUENCE CHARACTERISTICS:
            (A) LENGTH: 11 amino acids
            (B) TYPE: amino acid
            (D) TOPOLOGY: circular (ix) FEATURE:
            (A) NAME/KEY: Peptide
            (B) LOCATION: 2
            (D) OTHER INFORMATION: /note= "Xaa = (Pmc)"

(ix) FEATURE:
            (A) NAME/KEY: Peptide
            (B) LOCATION: 8
            (D) OTHER INFORMATION: /note= "Xaa = (p-nitro-F)"

(xi) SEQUENCE DESCRIPTION: SEQ ID NO:81:

Arg Xaa Gly His Arg Gly Asp Xaa Lys Cys Arg
1               5                   10

(2) INFORMATION FOR SEQ ID NO:82:

(i) SEQUENCE CHARACTERISTICS:
            (A) LENGTH: 11 amino acids
            (B) TYPE: amino acid
            (D) TOPOLOGY: circular

```
    (ix) FEATURE:
        (A) NAME/KEY: Peptide
        (B) LOCATION: 2
        (D) OTHER INFORMATION: /note= "Xaa = (Pmc)"

(ix) FEATURE:
        (A) NAME/KEY: Peptide
        (B) LOCATION: 8
        (D) OTHER INFORMATION: /note= "Xaa = (p-iodo-F)"

(xi) SEQUENCE DESCRIPTION: SEQ ID NO:82:

Arg Xaa Gly His Arg Gly Asp Xaa Lys Cys Arg
 1               5                  10

(2) INFORMATION FOR SEQ ID NO:83:

(i) SEQUENCE CHARACTERISTICS:
        (A) LENGTH: 9 amino acids
        (B) TYPE: amino acid
        (D) TOPOLOGY: circular (ix) FEATURE:
        (A) NAME/KEY: Peptide
        (B) LOCATION: 1
        (D) OTHER INFORMATION: /note= "N-terminal amino acid is        acetyla (ix) FEATURE:
        (A) NAME/KEY: Peptide
        (B) LOCATION: 7
        (D) OTHER INFORMATION: /note= "Xaa = (Y-OMe); C-terminal        amino (xi) SEQUENCE DESCRIPTION: SEQ ID NO:83:

Xaa Gly His Arg Gly Asp Xaa Arg Cys
 1               5

(2) INFORMATION FOR SEQ ID NO:84:

(i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pmc)"

(ix) FEATURE:
        (A) NAME/KEY: Peptide
        (B) LOCATION: 8
        (D) OTHER INFORMATION: /note= "Xaa = (Y-OMe)"

(xi) SEQUENCE DESCRIPTION: SEQ ID NO:84:

Asp Xaa Gly His Arg Gly Asp Xaa Arg Cys Arg
 1               5                  10

(2) INFORMATION FOR SEQ ID NO:85:

(i) SEQUENCE CHARACTERISTICS:
        (A) LENGTH: 9 amino acids
        (B) TYPE: amino acid
        (D) TOPOLOGY: circular (ix) FEATURE:
        (A) NAME/KEY: Peptide
        (B) LOCATION: 1
        (D) OTHER INFORMATION: /note= "N-terminal amino acid is        acetyla (ix) FEATURE:
        (A) NAME/KEY: Peptide
        (B) LOCATION: 7
        (D) OTHER INFORMATION: /note= "Xaa = (Y-OMe); C-terminal        amino
```

(xi) SEQUENCE DESCRIPTION: SEQ ID NO:85:

Xaa Ile Pro Arg Gly Asp Xaa Arg Cys
1               5

(2) INFORMATION FOR SEQ ID NO:86:

(i) SEQUENCE CHARACTERISTICS:
       (A) LENGTH: 9 amino acids
       (B) TYPE: amino acid
       (D) TOPOLOGY: circular (ix) FEATURE:
       (A) NAME/KEY: Peptide
       (B) LOCATION: 1
       (D) OTHER INFORMATION: /note= "N-terminal amino acid is         acetyla (ix) FEATURE:
       (A) NAME/KEY: Peptide
       (B) LOCATION: 7
       (D) OTHER INFORMATION: /note= "Xaa = (Y-OMe); C-terminal        amino (xi) SEQUENCE DESCRIPTION: SEQ ID NO:86:

Xaa Asn Pro Arg Gly Asp Xaa Arg Cys
1               5

(2) INFORMATION FOR SEQ ID NO:87:

(i) SEQUENCE CHARACTERISTICS:
       (A) LENGTH: 11 amino acids
       (B) TYPE: amino acid
       (D) TOPOLOGY: circular (ix) FEATURE:
       (A) NAME/KEY: Peptide
       (B) LOCATION: 2
       (D) OTHER INFORMATION: /note= "Xaa = (dPen)"

(ix) FEATURE:
       (A) NAME/KEY: Peptide
       (B) LOCATION: 8
       (D) OTHER INFORMATION: /note= "Xaa = (Y-OMe)"

(xi) SEQUENCE DESCRIPTION: SEQ ID NO:87:

Arg Xaa Asn Pro Arg Gly Asp Xaa Arg Cys Arg
1               5                   10

(2) INFORMATION FOR SEQ ID NO:88:

(i) SEQUENCE CHARACTERISTICS:
       (A) LENGTH: 8 amino acids
       (B) TYPE: amino acid
       (D) TOPOLOGY: circular (xi) SEQUENCE DESCRIPTION: SEQ ID NO:88:

Gly Arg Gly Asp Ser Pro Asp Gly
1               5

(2) INFORMATION FOR SEQ ID NO:89:

(i) SEQUENCE CHARACTERISTICS:
       (A) LENGTH: 8 amino acids
       (B) TYPE: amino acid
       (D) TOPOLOGY: circular (xi) SEQUENCE DESCRIPTION: SEQ ID NO:89:

Phe Arg Gly Asp Ser Pro Asp Gly
1               5

(2) INFORMATION FOR SEQ ID NO:90:

```
    (i) SEQUENCE CHARACTERISTICS:
        (A) LENGTH: 8 amino acids
        (B) TYPE: amino acid
        (D) TOPOLOGY: circular (xi) SEQUENCE DESCRIPTION: SEQ ID NO:90:

Tyr Arg Gly Asp Ser Pro Asp Gly
1               5

(2) INFORMATION FOR SEQ ID NO:91:

(i) SEQUENCE CHARACTERISTICS:
        (A) LENGTH: 8 amino acids
        (B) TYPE: amino acid
        (D) TOPOLOGY: circular (xi) SEQUENCE DESCRIPTION: SEQ ID NO:91:

Leu Arg Gly Asp Ser Pro Asp Gly
1               5

(2) INFORMATION FOR SEQ ID NO:92:

(i) SEQUENCE CHARACTERISTICS:
        (A) LENGTH: 8 amino acids
        (B) TYPE: amino acid
        (D) TOPOLOGY: circular (ix) FEATURE:
        (A) NAME/KEY: Peptide
        (B) LOCATION: 1
        (D) OTHER INFORMATION: /note= "Xaa = dSer"

(xi) SEQUENCE DESCRIPTION: SEQ ID NO:92:

Xaa Arg Gly Asp Ser Pro Asp Gly
1               5

(2) INFORMATION FOR SEQ ID NO:93:

(i) SEQUENCE CHARACTERISTICS:
        (A) LENGTH: 8 amino acids
        (B) TYPE: amino acid
        (D) TOPOLOGY: circular (xi) SEQUENCE DESCRIPTION: SEQ ID NO:93:

Val Arg Gly Asp Ser Pro Asp Gly
1               5

(2) INFORMATION FOR SEQ ID NO:94:

(i) SEQUENCE CHARACTERISTICS:
        (A) LENGTH: 10 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pen)"

(xi) SEQUENCE DESCRIPTION: SEQ ID NO:94:

Gly Xaa Gly Arg Gly Asp Arg Pro Cys Ala
1               5                   10

(2) INFORMATION FOR SEQ ID NO:95:

(i) SEQUENCE CHARACTERISTICS:
        (A) LENGTH: 10 amino acids
        (B) TYPE: amino acid
```

```
        (D) TOPOLOGY: circular (ix) FEATURE:
        (A) NAME/KEY: Peptide
        (B) LOCATION: 2
        (D) OTHER INFORMATION: /note= "Xaa = (Pen)"

(xi) SEQUENCE DESCRIPTION: SEQ ID NO:95:

Gly Xaa Leu Arg Gly Asp Thr Pro Cys Ala
1               5                   10

(2) INFORMATION FOR SEQ ID NO:96:

(i) SEQUENCE CHARACTERISTICS:
        (A) LENGTH: 10 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pen)"

(xi) SEQUENCE DESCRIPTION: SEQ ID NO:96:

Gly Xaa Val Arg Gly Asp Ser Pro Cys Ala
1               5                   10

(2) INFORMATION FOR SEQ ID NO:97:

(i) SEQUENCE CHARACTERISTICS:
        (A) LENGTH: 10 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pen)"

(xi) SEQUENCE DESCRIPTION: SEQ ID NO:97:

Gly Xaa Tyr Arg Gly Asp Ser Pro Cys Ala
1               5                   10

(2) INFORMATION FOR SEQ ID NO:98:

(i) SEQUENCE CHARACTERISTICS:
        (A) LENGTH: 10 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pen)"

(xi) SEQUENCE DESCRIPTION: SEQ ID NO:98:

Gly Xaa Leu Arg Gly Asp Ser Pro Cys Ala
1               5                   10

(2) INFORMATION FOR SEQ ID NO:99:

(i) SEQUENCE CHARACTERISTICS:
        (A) LENGTH: 10 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pen)"
```

(xi) SEQUENCE DESCRIPTION: SEQ ID NO:99:

Gly Xaa Leu Arg Gly Asp Ser Arg Cys Ala
1               5                   10

(2) INFORMATION FOR SEQ ID NO:100:

(i) SEQUENCE CHARACTERISTICS:
        (A) LENGTH: 10 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pen)"

(xi) SEQUENCE DESCRIPTION: SEQ ID NO:100:

Gly Xaa Gly Arg Gly Asp Ser Phe Cys Ala
1               5                   10

(2) INFORMATION FOR SEQ ID NO:101:

(i) SEQUENCE CHARACTERISTICS:
        (A) LENGTH: 10 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pen)"

(xi) SEQUENCE DESCRIPTION: SEQ ID NO:101:

Gly Xaa Phe Arg Gly Asp Ser Phe Cys Ala
1               5                   10

(2) INFORMATION FOR SEQ ID NO:102:

(i) SEQUENCE CHARACTERISTICS:
        (A) LENGTH: 10 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pen)"

(xi) SEQUENCE DESCRIPTION: SEQ ID NO:102:

Gly Xaa Gly Arg Gly Asp Thr Pro Cys Arg
1               5                   10

(2) INFORMATION FOR SEQ ID NO:103:

(i) SEQUENCE CHARACTERISTICS:
        (A) LENGTH: 10 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pen)"

(xi) SEQUENCE DESCRIPTION: SEQ ID NO:103:

Arg Xaa Gly Arg Gly Asp Thr Pro Cys Ala
1               5                   10

(2) INFORMATION FOR SEQ ID NO:104:

(i) SEQUENCE CHARACTERISTICS:
    (A) LENGTH: 10 amino acids
    (B) TYPE: amino acid
    (D) TOPOLOGY: circular (ix) FEATURE:
    (A) NAME/KEY: Peptide
    (B) LOCATION: 2
    (D) OTHER INFORMATION: /note= "Xaa = (Pen)"

(xi) SEQUENCE DESCRIPTION: SEQ ID NO:104:

Lys Xaa Gly Arg Gly Asp Thr Pro Cys Ala
 1               5                  10

(2) INFORMATION FOR SEQ ID NO:105:

(i) SEQUENCE CHARACTERISTICS:
        (A) LENGTH: 10 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pen)"

(xi) SEQUENCE DESCRIPTION: SEQ ID NO:105:

Arg Xaa Gly Arg Gly Asp Thr Pro Cys Arg
 1               5                  10

(2) INFORMATION FOR SEQ ID NO:106:

(i) SEQUENCE CHARACTERISTICS:
        (A) LENGTH: 10 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pen)"

(xi) SEQUENCE DESCRIPTION: SEQ ID NO:106:

Arg Xaa Gly Arg Gly Asp Thr Pro Cys Lys
 1               5                  10

(2) INFORMATION FOR SEQ ID NO:107:

(i) SEQUENCE CHARACTERISTICS:
        (A) LENGTH: 10 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pen)"

(xi) SEQUENCE DESCRIPTION: SEQ ID NO:107:

Arg Xaa Gly Arg Gly Asp Ser Arg Cys Ala
 1               5                  10

(2) INFORMATION FOR SEQ ID NO:108:

(i) SEQUENCE CHARACTERISTICS:
        (A) LENGTH: 10 amino acids
        (B) TYPE: amino acid
        (D) TOPOLOGY: circular (ix) FEATURE:

(A) NAME/KEY: Peptide
        (B) LOCATION: 2
        (D) OTHER INFORMATION: /note= "Xaa = (Pen)"

(xi) SEQUENCE DESCRIPTION: SEQ ID NO:108:

Arg Xaa Gly Arg Gly Asp Leu Arg Cys Ala
1               5                   10

(2) INFORMATION FOR SEQ ID NO:109:

(i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pen)"

(xi) SEQUENCE DESCRIPTION: SEQ ID NO:109:

Gly Xaa Gly His Arg Gly Asp Thr Arg Cys Ala
1               5                   10

(2) INFORMATION FOR SEQ ID NO:110:

(i) SEQUENCE CHARACTERISTICS:
        (A) LENGTH: 10 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pen)"

(xi) SEQUENCE DESCRIPTION: SEQ ID NO:110:

Arg Xaa Gly Arg Gly Asp Thr Pro Cys Ala
1               5                   10

(2) INFORMATION FOR SEQ ID NO:111:

(i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pen)"

(xi) SEQUENCE DESCRIPTION: SEQ ID NO:111:

Arg Xaa Gly His Arg Gly Asp Thr Arg Cys Arg
1               5                   10

(2) INFORMATION FOR SEQ ID NO:112:

(i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pen)"

(xi) SEQUENCE DESCRIPTION: SEQ ID NO:112:

Leu Xaa Gly His Arg Gly Asp Leu Arg Cys Ala (2) INFORMATION FOR SEQ ID NO:113:

(i) SEQUENCE CHARACTERISTICS:
        (A) LENGTH: 9 amino acids
        (B) TYPE: amino acid
        (D) TOPOLOGY: circular (ix) FEATURE:
        (A) NAME/KEY: Peptide
        (B) LOCATION: 1
        (D) OTHER INFORMATION: /note= "Xaa = (Pmp)"

(xi) SEQUENCE DESCRIPTION: SEQ ID NO:113:

Xaa Gly Arg Gly Asp Ser Pro Cys Ala
1          5

(2) INFORMATION FOR SEQ ID NO:114:

(i) SEQUENCE CHARACTERISTICS:
        (A) LENGTH: 9 amino acids
        (B) TYPE: amino acid
        (D) TOPOLOGY: circular (ix) FEATURE:
        (A) NAME/KEY: Peptide
        (B) LOCATION: 1
        (D) OTHER INFORMATION: /note= "Xaa = (Pmp)"

(xi) SEQUENCE DESCRIPTION: SEQ ID NO:114:

Xaa Gly Arg Gly Asp Thr Pro Cys Ala
1          5

(2) INFORMATION FOR SEQ ID NO:115:

(i) SEQUENCE CHARACTERISTICS:
        (A) LENGTH: 10 amino acids
        (B) TYPE: amino acid
        (D) TOPOLOGY: circular (ix) FEATURE:
        (A) NAME/KEY: Peptide
        (B) LOCATION: 1
        (D) OTHER INFORMATION: /note= "Xaa = (Pmp)"

(ix) FEATURE:
        (A) NAME/KEY: Peptide
        (B) LOCATION: 9
        (D) OTHER INFORMATION: /note= "Xaa = (Pen)"

(xi) SEQUENCE DESCRIPTION: SEQ ID NO:115:

Xaa Gly His Arg Gly Asp Leu Arg Xaa Ala
1          5               10

(2) INFORMATION FOR SEQ ID NO:116:

(i) SEQUENCE CHARACTERISTICS:
        (A) LENGTH: 10 amino acids
        (B) TYPE: amino acid
        (D) TOPOLOGY: circular (ix) FEATURE:
        (A) NAME/KEY: Peptide
        (B) LOCATION: 1
        (D) OTHER INFORMATION: /note= "Xaa = (t-butyl-amino-Pmp)"

(xi) SEQUENCE DESCRIPTION: SEQ ID NO:116:

Xaa Gly His Arg Gly Asp Leu Arg Cys Ala
1          5               10

(2) INFORMATION FOR SEQ ID NO:117:

(i) SEQUENCE CHARACTERISTICS:
        (A) LENGTH: 10 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (amino-Pmp)"

(xi) SEQUENCE DESCRIPTION: SEQ ID NO:117:

```
Arg Xaa Gly Arg Gly Asp Thr Pro Cys Ala
1               5                   10
```

(2) INFORMATION FOR SEQ ID NO:118:

(i) SEQUENCE CHARACTERISTICS:
        (A) LENGTH: 11 amino acids
        (B) TYPE: amino acid
        (D) TOPOLOGY: circular (xi) SEQUENCE DESCRIPTION: SEQ ID NO:118:

```
Gly His Arg Gly Asp Leu Arg Asp Ala Ser Gly
1               5                   10
```

(2) INFORMATION FOR SEQ ID NO:119:

(i) SEQUENCE CHARACTERISTICS:
        (A) LENGTH: 11 amino acids
        (B) TYPE: amino acid
        (D) TOPOLOGY: circular (xi) SEQUENCE DESCRIPTION: SEQ ID NO:119:

```
Arg Lys Gly His Arg Gly Asp Leu Arg Asp Arg
1               5                   10
```

(2) INFORMATION FOR SEQ ID NO:120:

(i) SEQUENCE CHARACTERISTICS:
        (A) LENGTH: 14 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (orn)"

(xi) SEQUENCE DESCRIPTION: SEQ ID NO:120:

```
Arg Xaa Gly His Arg Gly Asp Leu Arg Asp Arg Ala Ser Gly
1               5                   10
```

(2) INFORMATION FOR SEQ ID NO:121:

(i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (orn)"

(xi) SEQUENCE DESCRIPTION: SEQ ID NO:121:

```
Arg Xaa Gly His Arg Gly Asp Leu Arg Asp Arg
1               5                   10
```

(2) INFORMATION FOR SEQ ID NO:122:

(i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (orn)"

(xi) SEQUENCE DESCRIPTION: SEQ ID NO:122:

Arg Xaa Gly His Arg Gly Asp Leu Arg Glu Arg
1             5                10

(2) INFORMATION FOR SEQ ID NO:123:

(i) SEQUENCE CHARACTERISTICS:
        (A) LENGTH: 9 amino acids
        (B) TYPE: amino acid
        (D) TOPOLOGY: circular (ix) FEATURE:
        (A) NAME/KEY: Peptide
        (B) LOCATION: 8
        (D) OTHER INFORMATION: /note= "Xaa = (Pas); C-terminal         amino ac (xi) SEQUENCE DESCRIPTION: SEQ ID NO:123:

Gly His Arg Gly Asp Leu Arg Xaa Ala
1             5

(2) INFORMATION FOR SEQ ID NO:124:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO:124:

Arg Arg Arg Arg Arg Arg Arg Arg Arg Gly Asp Ser
1             5                10

(2) INFORMATION FOR SEQ ID NO:125:

(i) SEQUENCE CHARACTERISTICS:
        (A) LENGTH: 9 amino acids
        (B) TYPE: amino acid
        (D) TOPOLOGY: circular (ix) FEATURE:
        (A) NAME/KEY: Peptide
        (B) LOCATION: 7
        (D) OTHER INFORMATION: /note= "N-terminal amino acid is         acetyla (xi) SEQUENCE DESCRIPTION: SEQ ID NO:125:

Cys Asn Pro Arg Gly Asp Xaa Glu Cys
1             5

(2) INFORMATION FOR SEQ ID NO:126:

(i) SEQUENCE CHARACTERISTICS:
        (A) LENGTH: 9 amino acids
        (B) TYPE: amino acid
        (D) TOPOLOGY: circular (ix) FEATURE:
        (A) NAME/KEY: Peptide
        (B) LOCATION: 7

(D) OTHER INFORMATION: /note= "N-terminal amino acid is          acetyla (xi) SEQUENCE DESCRIPTION: SEQ ID NO:126:

Cys Asn Pro Arg Gly Asp Xaa Ala Cys
1               5

(2) INFORMATION FOR SEQ ID NO:127:

(i) SEQUENCE CHARACTERISTICS:
        (A) LENGTH: 9 amino acids
        (B) TYPE: amino acid
        (D) TOPOLOGY: circular (ix) FEATURE:
        (A) NAME/KEY: Peptide
        (B) LOCATION: 7
        (D) OTHER INFORMATION: /note= "N-terminal amino acid is          acetyla (ix) FEATURE:
        (A) NAME/KEY: Peptide
        (B) LOCATION: 8
        (D) OTHER INFORMATION: /note= "Xaa = (dR); C-terminal             amino aci (xi) SEQUENCE DESCRIPTION: SEQ ID NO:127:

Cys Asn Pro Arg Gly Asp Xaa Xaa Cys
1               5

(2) INFORMATION FOR SEQ ID NO:128:

(i) SEQUENCE CHARACTERISTICS:
        (A) LENGTH: 9 amino acids
        (B) TYPE: amino acid
        (D) TOPOLOGY: circular (ix) FEATURE:
        (A) NAME/KEY: Peptide
        (B) LOCATION: 7
        (D) OTHER INFORMATION: /note= "N-terminal amino acid is          acetyla (ix) FEATURE:
        (A) NAME/KEY: Peptide
        (B) LOCATION: 8
        (D) OTHER INFORMATION: /note= "Xaa = Orn; C-terminal amino              acid (xi) SEQUENCE DESCRIPTION: SEQ ID NO:128:

Cys Asn Pro Arg Gly Asp Xaa Xaa Cys
1               5

(2) INFORMATION FOR SEQ ID NO:129:

(i) SEQUENCE CHARACTERISTICS:
        (A) LENGTH: 9 amino acids
        (B) TYPE: amino acid
        (D) TOPOLOGY: circular (ix) FEATURE:
        (A) NAME/KEY: Peptide
        (B) LOCATION: 7
        (D) OTHER INFORMATION: /note= "N-terminal amino acid is          acetyla (xi) SEQUENCE DESCRIPTION: SEQ ID NO:129:

Cys Asn Pro Arg Gly Asp Xaa Lys Cys
1               5

(2) INFORMATION FOR SEQ ID NO:130:

(i) SEQUENCE CHARACTERISTICS:
        (A) LENGTH: 9 amino acids
        (B) TYPE: amino acid
        (D) TOPOLOGY: circular

```
    (ix) FEATURE:
        (A) NAME/KEY: Peptide
        (B) LOCATION: 7
        (D) OTHER INFORMATION: /note= "N-terminal amino acid is          acetyla (ix) FEATURE:
        (A) NAME/KEY: Peptide
        (B) LOCATION: 8
        (D) OTHER INFORMATION: /note= "Xaa = (Cit); C-terminal            amino ac (xi) SEQUENCE DESCRIPTION: SEQ ID NO:130:

Cys Asn Pro Arg Gly Asp Xaa Xaa Cys
1               5

(2) INFORMATION FOR SEQ ID NO:131:

(i) SEQUENCE CHARACTERISTICS:
        (A) LENGTH: 9 amino acids
        (B) TYPE: amino acid
        (D) TOPOLOGY: circular (ix) FEATURE:
        (A) NAME/KEY: Peptide
        (B) LOCATION: 7
        (D) OTHER INFORMATION: /note= "N-terminal amino acid is          acetyla (ix) FEATURE:
        (A) NAME/KEY: Peptide
        (B) LOCATION: 8
        (D) OTHER INFORMATION: /note= "Xaa = (Nle); C-terminal            amino ac (xi) SEQUENCE DESCRIPTION: SEQ ID NO:131:

Cys Asn Pro Arg Gly Asp Xaa Xaa Cys
1               5

(2) INFORMATION FOR SEQ ID NO:132:

(i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pen)"

(xi) SEQUENCE DESCRIPTION: SEQ ID NO:132:

Gly Xaa Arg Ala Arg Gly Asp Asn Pro Cys Ala
1               5                   10

(2) INFORMATION FOR SEQ ID NO:133:

(i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pmc)"

(ix) FEATURE:
        (A) NAME/KEY: Peptide
        (B) LOCATION: 8
        (D) OTHER INFORMATION: /note= "Xaa = (p-iodo-F)"

(xi) SEQUENCE DESCRIPTION: SEQ ID NO:133:

Arg Xaa Gly His Arg Gly Asp Xaa Arg Cys Arg
1               5                   10
```

(2) INFORMATION FOR SEQ ID NO:134:

(i) SEQUENCE CHARACTERISTICS:
        (A) LENGTH: 9 amino acids
        (B) TYPE: amino acid
        (D) TOPOLOGY: circular (ix) FEATURE:
        (A) NAME/KEY: Peptide
        (B) LOCATION: 7
        (D) OTHER INFORMATION: /note= "N-terminal amino acid is acetyla (xi) SEQUENCE DESCRIPTION: SEQ ID NO:134:

Cys Ser Pro Arg Gly Asp Xaa Arg Cys
1            5

(2) INFORMATION FOR SEQ ID NO:135:

(i) SEQUENCE CHARACTERISTICS:
        (A) LENGTH: 9 amino acids
        (B) TYPE: amino acid
        (D) TOPOLOGY: circular (ix) FEATURE:
        (A) NAME/KEY: Peptide
        (B) LOCATION: 7
        (D) OTHER INFORMATION: /note= "N-terminal amino acid is acetyla (xi) SEQUENCE DESCRIPTION: SEQ ID NO:135:

Cys Ala Pro Arg Gly Asp Xaa Arg Cys
1            5

(2) INFORMATION FOR SEQ ID NO:136:

(i) SEQUENCE CHARACTERISTICS:
        (A) LENGTH: 9 amino acids
        (B) TYPE: amino acid
        (D) TOPOLOGY: circular (ix) FEATURE:
        (A) NAME/KEY: Peptide
        (B) LOCATION: 7
        (D) OTHER INFORMATION: /note= "N-terminal amino acid is acetyla (xi) SEQUENCE DESCRIPTION: SEQ ID NO:136:

Cys Leu Pro Arg Gly Asp Xaa Arg Cys
1            5

(2) INFORMATION FOR SEQ ID NO:137:

(i) SEQUENCE CHARACTERISTICS:
        (A) LENGTH: 9 amino acids
        (B) TYPE: amino acid
        (D) TOPOLOGY: circular (ix) FEATURE:
        (A) NAME/KEY: Peptide
        (B) LOCATION: 7
        (D) OTHER INFORMATION: /note= "N-terminal amino acid is acetyla (xi) SEQUENCE DESCRIPTION: SEQ ID NO:137:

Cys Asp Pro Arg Gly Asp Xaa Arg Cys
1            5

(2) INFORMATION FOR SEQ ID NO:138:

(i) SEQUENCE CHARACTERISTICS:
        (A) LENGTH: 9 amino acids
        (B) TYPE: amino acid
        (D) TOPOLOGY: circular

```
    (ix) FEATURE:
         (A) NAME/KEY: Peptide
         (B) LOCATION: 7
         (D) OTHER INFORMATION: /note= "N-terminal amino acid is          acetyla (xi) SEQUENCE DESCRIPTION: SEQ ID NO:138:

Cys Tyr Pro Arg Gly Asp Xaa Arg Cys
1               5

(2) INFORMATION FOR SEQ ID NO:139:

(i) SEQUENCE CHARACTERISTICS:
        (A) LENGTH: 9 amino acids
        (B) TYPE: amino acid
        (D) TOPOLOGY: circular (ix) FEATURE:
         (A) NAME/KEY: Peptide
         (B) LOCATION: 7
         (D) OTHER INFORMATION: /note= "N-terminal amino acid is          acetyla (xi) SEQUENCE DESCRIPTION: SEQ ID NO:139:

Cys Arg Pro Arg Gly Asp Xaa Arg Cys
1               5

(2) INFORMATION FOR SEQ ID NO:140:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO:140:

Gly Arg Gly Asp Ser Pro Lys
1               5

(2) INFORMATION FOR SEQ ID NO:141:

(i) SEQUENCE CHARACTERISTICS:
        (A) LENGTH: 11 amino acids
        (B) TYPE: amino acid
        (D) TOPOLOGY: circular (ix) FEATURE:
         (A) NAME/KEY: Peptide
         (B) LOCATION: 2
         (D) OTHER INFORMATION: /note= "Xaa = (Pen)"

(xi) SEQUENCE DESCRIPTION: SEQ ID NO:141:

Arg Xaa Gly His Arg Gly Asp Leu Arg Cys Arg
1               5                   10

(2) INFORMATION FOR SEQ ID NO:142:

(i) SEQUENCE CHARACTERISTICS:
        (A) LENGTH: 11 amino acids
        (B) TYPE: amino acid
        (D) TOPOLOGY: circular (ix) FEATURE:
         (A) NAME/KEY: Peptide
         (B) LOCATION: 2
         (D) OTHER INFORMATION: /note= "Xaa = (D-Pen)"

(xi) SEQUENCE DESCRIPTION: SEQ ID NO:142:

Arg Xaa Gly His Arg Gly Asp Leu Arg Cys Arg
1               5                   10
```

(2) INFORMATION FOR SEQ ID NO:143:

(i) SEQUENCE CHARACTERISTICS:
        (A) LENGTH: 10 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pmc)"

(xi) SEQUENCE DESCRIPTION: SEQ ID NO:143:

Arg Xaa Gly His Arg Gly Asp Arg Cys Arg
1               5                   10

(2) INFORMATION FOR SEQ ID NO:144:

(i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Tmc)"

(xi) SEQUENCE DESCRIPTION: SEQ ID NO:144:

Arg Xaa Gly His Arg Gly Asp Leu Arg Cys Arg
1               5                   10

(2) INFORMATION FOR SEQ ID NO:145:

(i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pmc)"

(xi) SEQUENCE DESCRIPTION: SEQ ID NO:145:

Arg Xaa Gly His Arg Gly Asp Leu Arg Cys Arg
1               5                   10

(2) INFORMATION FOR SEQ ID NO:146:

(i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pmc)"

(ix) FEATURE:
        (A) NAME/KEY: Peptide
        (B) LOCATION: 8
        (D) OTHER INFORMATION: /note= "Xaa = (p-Cl-F)"

(xi) SEQUENCE DESCRIPTION: SEQ ID NO:146:

Arg Xaa Gly His Arg Gly Asp Xaa Arg Cys Arg
1               5                   10

(2) INFORMATION FOR SEQ ID NO:147:

```
    (i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pmc)"

(ix) FEATURE:
        (A) NAME/KEY: Peptide
        (B) LOCATION: 8
        (D) OTHER INFORMATION: /note= "Xaa = (Y-OMe)"

(xi) SEQUENCE DESCRIPTION: SEQ ID NO:147:

Arg Xaa Asp His Arg Gly Asp Xaa Arg Cys Arg
1               5                   10

(2) INFORMATION FOR SEQ ID NO:148:

(i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pmc)"

(ix) FEATURE:
        (A) NAME/KEY: Peptide
        (B) LOCATION: 8
        (D) OTHER INFORMATION: /note= "Xaa = (Y-OMe)"

(xi) SEQUENCE DESCRIPTION: SEQ ID NO:148:

Arg Xaa Ser His Arg Gly Asp Xaa Arg Cys Arg
1               5                   10

(2) INFORMATION FOR SEQ ID NO:149:

(i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pmc)"

(ix) FEATURE:
        (A) NAME/KEY: Peptide
        (B) LOCATION: 8
        (D) OTHER INFORMATION: /note= "Xaa = (Y-OMe)"

(xi) SEQUENCE DESCRIPTION: SEQ ID NO:149:

Arg Xaa Ile His Arg Gly Asp Xaa Arg Cys Arg
1               5                   10

(2) INFORMATION FOR SEQ ID NO:150:

(i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa = (Pmc)"
```

(ix) FEATURE:
            (A) NAME/KEY: Peptide
            (B) LOCATION: 4
            (D) OTHER INFORMATION: /note= "Xaa = (dHis)"

(ix) FEATURE:
            (A) NAME/KEY: Peptide
            (B) LOCATION: 8
            (D) OTHER INFORMATION: /note= "Xaa = (Y-OMe)"

(xi) SEQUENCE DESCRIPTION: SEQ ID NO:150:

Arg Xaa Gly Xaa Arg Gly Asp Xaa Arg Cys Arg
1               5                   10

(2) INFORMATION FOR SEQ ID NO:151:

(i) SEQUENCE CHARACTERISTICS:
            (A) LENGTH: 11 amino acids
            (B) TYPE: amino acid
            (D) TOPOLOGY: circular (ix) FEATURE:
            (A) NAME/KEY: Peptide
            (B) LOCATION: 2
            (D) OTHER INFORMATION: /note= "Xaa = (Pmc)"

(ix) FEATURE:
            (A) NAME/KEY: Peptide
            (B) LOCATION: 8
            (D) OTHER INFORMATION: /note= "Xaa = (Y-OMe)"

(xi) SEQUENCE DESCRIPTION: SEQ ID NO:151:

Arg Xaa Gly Tyr Arg Gly Asp Xaa Arg Cys Arg
1               5                   10

(2) INFORMATION FOR SEQ ID NO:152:

(i) SEQUENCE CHARACTERISTICS:
            (A) LENGTH: 11 amino acids
            (B) TYPE: amino acid
            (D) TOPOLOGY: circular (ix) FEATURE:
            (A) NAME/KEY: Peptide
            (B) LOCATION: 2
            (D) OTHER INFORMATION: /note= "Xaa = (Pmc)"

(ix) FEATURE:
            (A) NAME/KEY: Peptide
            (B) LOCATION: 4
            (D) OTHER INFORMATION: /note= "Xaa = (dTyr)"

(ix) FEATURE:
            (A) NAME/KEY: Peptide
            (B) LOCATION: 8
            (D) OTHER INFORMATION: /note= "Xaa = (Y-OMe)"

(xi) SEQUENCE DESCRIPTION: SEQ ID NO:152:

Arg Xaa Gly Xaa Arg Gly Asp Xaa Arg Cys Arg
1               5                   10

(2) INFORMATION FOR SEQ ID NO:153:

(i) SEQUENCE CHARACTERISTICS:
            (A) LENGTH: 11 amino acids
            (B) TYPE: amino acid
            (D) TOPOLOGY: circular (ix) FEATURE:
            (A) NAME/KEY: Peptide
            (B) LOCATION: 2
            (D) OTHER INFORMATION: /note= "Xaa = (Pmc)"

```
    (ix) FEATURE:
          (A) NAME/KEY: Peptide
          (B) LOCATION: 8
          (D) OTHER INFORMATION: /note= "Xaa = (Y-OMe)"

(xi) SEQUENCE DESCRIPTION: SEQ ID NO:153:

Arg Xaa Gly Pro Arg Gly Asp Xaa Arg Cys Arg
1               5                   10

(2) INFORMATION FOR SEQ ID NO:154:

(i) SEQUENCE CHARACTERISTICS:
          (A) LENGTH: 9 amino acids
          (B) TYPE: amino acid
          (D) TOPOLOGY: circular (ix) FEATURE:
          (A) NAME/KEY: Peptide
          (B) LOCATION: 1
          (D) OTHER INFORMATION: /note= "N-terminal amino acid is          acetyla (ix) FEATURE:
          (A) NAME/KEY: Peptide
          (B) LOCATION: 9
          (D) OTHER INFORMATION: /note= "C-terminal amino acid is          amidate (xi) SEQUENCE DESCRIPTION: SEQ ID NO:154:

Cys Ile Pro Arg Gly Asp Tyr Arg Cys
1               5

(2) INFORMATION FOR SEQ ID NO:155:

(i) SEQUENCE CHARACTERISTICS:
          (A) LENGTH: 9 amino acids
          (B) TYPE: amino acid
          (D) TOPOLOGY: circular (ix) FEATURE:
          (A) NAME/KEY: Peptide
          (B) LOCATION: 1
          (D) OTHER INFORMATION: /note= "N-terminal amino acid is          acetyla (ix) FEATURE:
          (A) NAME/KEY: Peptide
          (B) LOCATION: 9
          (D) OTHER INFORMATION: /note= "C-terminal amino acid is          amidate (xi) SEQUENCE DESCRIPTION: SEQ ID NO:155:

Cys Ile Pro Arg Gly Asp Phe Arg Cys
1               5

(2) INFORMATION FOR SEQ ID NO:156:

(i) SEQUENCE CHARACTERISTICS:
          (A) LENGTH: 9 amino acids
          (B) TYPE: amino acid
          (D) TOPOLOGY: circular (ix) FEATURE:
          (A) NAME/KEY: Peptide
          (B) LOCATION: 7
          (D) OTHER INFORMATION: /note= "N-terminal amino acid is          acetyla (xi) SEQUENCE DESCRIPTION: SEQ ID NO:156:

Cys Ile Pro Arg Gly Asp Xaa Arg Cys
1               5

(2) INFORMATION FOR SEQ ID NO:157:

(i) SEQUENCE CHARACTERISTICS:
          (A) LENGTH: 9 amino acids
```

```
            (B) TYPE: amino acid
            (D) TOPOLOGY: circular (ix) FEATURE:
            (A) NAME/KEY: Peptide
            (B) LOCATION: 7
            (D) OTHER INFORMATION: /note= "N-terminal amino acid is         acetyla (xi) SEQUENCE DESCRIPTION: SEQ ID NO:157:

Cys Ile Pro Arg Gly Asp Xaa Arg Cys
1               5

(2) INFORMATION FOR SEQ ID NO:158:

(i) SEQUENCE CHARACTERISTICS:
            (A) LENGTH: 9 amino acids
            (B) TYPE: amino acid
            (D) TOPOLOGY: circular (ix) FEATURE:
            (A) NAME/KEY: Peptide
            (B) LOCATION: 7
            (D) OTHER INFORMATION: /note= "N-terminal amino acid is         acetyla (xi) SEQUENCE DESCRIPTION: SEQ ID NO:158:

Cys Asn Pro Arg Gly Asp Xaa Arg Cys
1               5

(2) INFORMATION FOR SEQ ID NO:159:

(i) SEQUENCE CHARACTERISTICS:
            (A) LENGTH: 9 amino acids
            (B) TYPE: amino acid
            (D) TOPOLOGY: circular (ix) FEATURE:
            (A) NAME/KEY: Peptide
            (B) LOCATION: 7
            (D) OTHER INFORMATION: /note= "N-terminal amino acid is         acetyla (xi) SEQUENCE DESCRIPTION: SEQ ID NO:159:

Cys Asn Pro Arg Gly Asp Xaa Arg Cys
1               5

(2) INFORMATION FOR SEQ ID NO:160:

(i) SEQUENCE CHARACTERISTICS:
            (A) LENGTH: 9 amino acids
            (B) TYPE: amino acid
            (D) TOPOLOGY: circular (ix) FEATURE:
            (A) NAME/KEY: Peptide
            (B) LOCATION: 1
            (D) OTHER INFORMATION: /note= "N-terminal amino acid is         acetyla (ix) FEATURE:
            (A) NAME/KEY: Peptide
            (B) LOCATION: 7
            (D) OTHER INFORMATION: /note= "Xaa = (Y-OMe); C-terminal         amino (xi) SEQUENCE DESCRIPTION: SEQ ID NO:160:

Xaa Asn Pro Arg Gly Asp Xaa Arg Cys
1               5

(2) INFORMATION FOR SEQ ID NO:161:

(i) SEQUENCE CHARACTERISTICS:
            (A) LENGTH: 9 amino acids
            (B) TYPE: amino acid
            (D) TOPOLOGY: circular
```

```
    (ix) FEATURE:
         (A) NAME/KEY: Peptide
         (B) LOCATION: 1
         (D) OTHER INFORMATION: /note= "N-terminal amino acid is          acetyla (ix) FEATURE:
         (A) NAME/KEY: Peptide
         (B) LOCATION: 7
         (D) OTHER INFORMATION: /note= "Xaa = (Y-OMe); C-terminal         amino (xi) SEQUENCE DESCRIPTION: SEQ ID NO:161:

Xaa Asn Pro Arg Gly Asp Xaa Arg Cys
1               5

(2) INFORMATION FOR SEQ ID NO:162:

(i) SEQUENCE CHARACTERISTICS:
        (A) LENGTH: 9 amino acids
        (B) TYPE: amino acid
        (D) TOPOLOGY: circular (ix) FEATURE:
         (A) NAME/KEY: Peptide
         (B) LOCATION: 1
         (D) OTHER INFORMATION: /note= "N-terminal amino acid is          acetyla (ix) FEATURE:
         (A) NAME/KEY: Peptide
         (B) LOCATION: 7
         (D) OTHER INFORMATION: /note= "Xaa = (Y-OMe); C-terminal         amino (xi) SEQUENCE DESCRIPTION: SEQ ID NO:162:

Xaa Asn Pro Arg Gly Asp Xaa Arg Cys
1               5

(2) INFORMATION FOR SEQ ID NO:163:

(i) SEQUENCE CHARACTERISTICS:
        (A) LENGTH: 9 amino acids
        (B) TYPE: amino acid
        (D) TOPOLOGY: circular (ix) FEATURE:
         (A) NAME/KEY: Peptide
         (B) LOCATION: 1
         (D) OTHER INFORMATION: /note= "N-terminal amino acid is          acetyla (ix) FEATURE:
         (A) NAME/KEY: Peptide
         (B) LOCATION: 7
         (D) OTHER INFORMATION: /note= "Xaa = (Y-OMe); C-terminal         amino (xi) SEQUENCE DESCRIPTION: SEQ ID NO:163:

Xaa Asn Pro Arg Gly Asp Xaa Arg Cys
1               5

(2) INFORMATION FOR SEQ ID NO:164:

(i) SEQUENCE CHARACTERISTICS:
        (A) LENGTH: 9 amino acids
        (B) TYPE: amino acid
        (D) TOPOLOGY: circular (ix) FEATURE:
         (A) NAME/KEY: Peptide
         (B) LOCATION: 1
         (D) OTHER INFORMATION: /note= "N-terminal amino acid is          acetyla (ix) FEATURE:
         (A) NAME/KEY: Peptide
         (B) LOCATION: 7
         (D) OTHER INFORMATION: /note= "Xaa = (Y-OMe); C-terminal         amino
```

(xi) SEQUENCE DESCRIPTION: SEQ ID NO:164:

Xaa Ile Pro Arg Gly Asp Xaa Arg Cys
1               5

(2) INFORMATION FOR SEQ ID NO:165:

(i) SEQUENCE CHARACTERISTICS:
       (A) LENGTH: 9 amino acids
       (B) TYPE: amino acid
       (D) TOPOLOGY: circular (ix) FEATURE:
       (A) NAME/KEY: Peptide
       (B) LOCATION: 7
       (D) OTHER INFORMATION: /note= "N-terminal amino acid is      acetyla (xi) SEQUENCE DESCRIPTION: SEQ ID NO:165:

Cys Asn Pro Arg Gly Asp Xaa Leu Cys
1               5

(2) INFORMATION FOR SEQ ID NO:166:

(i) SEQUENCE CHARACTERISTICS:
       (A) LENGTH: 5 amino acids
       (B) TYPE: amino acid
       (D) TOPOLOGY: circular (ix) FEATURE:
       (A) NAME/KEY: Peptide
       (B) LOCATION: 1
       (D) OTHER INFORMATION: /note= "Xaa = a positively charged      amino (ix) FEATURE:
       (A) NAME/KEY: Peptide
       (B) LOCATION: 4
       (D) OTHER INFORMATION: /note= "Xaa = hydrophobic amino       acid."

(ix) FEATURE:
       (A) NAME/KEY: Peptide
       (B) LOCATION: 5
       (D) OTHER INFORMATION: /note= "Xaa = positively charged       amino a (xi) SEQUENCE DESCRIPTION: SEQ ID NO:166:

Xaa Gly Asp Xaa Xaa
1               5

(2) INFORMATION FOR SEQ ID NO:167:

(i) SEQUENCE CHARACTERISTICS:
       (A) LENGTH: 10 amino acids
       (B) TYPE: amino acid
       (D) TOPOLOGY: circular (ix) FEATURE:
       (A) NAME/KEY: Peptide
       (B) LOCATION: 1
       (D) OTHER INFORMATION: /note= "Xaa = (t-but-Pmp)"

(xi) SEQUENCE DESCRIPTION: SEQ ID NO:167:

Xaa Gly His Arg Gly Asp Leu Arg Cys Ala
1               5                   10

(2) INFORMATION FOR SEQ ID NO:168:

(i) SEQUENCE CHARACTERISTICS:
       (A) LENGTH: 5 amino acids
       (B) TYPE: amino acid
       (D) TOPOLOGY: linear (ix) FEATURE:

```
    (A) NAME/KEY: Peptide
    (B) LOCATION: 4
    (D) OTHER INFORMATION: /note= "Xaa = hydrophobic residue"

(xi) SEQUENCE DESCRIPTION: SEQ ID NO:168:

Arg Gly Asp Xaa Arg
1               5
```